US011027024B2

(12) United States Patent
Davidson et al.

(10) Patent No.: US 11,027,024 B2
(45) Date of Patent: Jun. 8, 2021

(54) METHODS OF DELIVERY OF TRANSGENES FOR TREATING BRAIN DISEASES

(71) Applicant: UNIVERSITY OF IOWA RESEARCH FOUNDATION, Iowa City, IA (US)

(72) Inventors: Beverly L. Davidson, Iowa City, IA (US); Megan S. Keiser, Iowa City, IA (US)

(73) Assignee: UNIVERSITY OF IOWA RESEARCH FOUNDATION, Iowa City, IA (US)

(*) Notice: Subject to any disclaimer, the term of this patent is extended or adjusted under 35 U.S.C. 154(b) by 180 days.

(21) Appl. No.: 15/578,170

(22) PCT Filed: May 31, 2016

(86) PCT No.: PCT/US2016/035087
§ 371 (c)(1),
(2) Date: Nov. 29, 2017

(87) PCT Pub. No.: WO2016/196507
PCT Pub. Date: Dec. 8, 2016

(65) Prior Publication Data
US 2018/0169269 A1 Jun. 21, 2018

Related U.S. Application Data

(60) Provisional application No. 62/168,618, filed on May 29, 2015.

(51) Int. Cl.
C12N 15/113 (2010.01)
A61K 48/00 (2006.01)
C07K 14/47 (2006.01)
A61P 25/00 (2006.01)
C12N 15/79 (2006.01)

(52) U.S. Cl.
CPC .......... *A61K 48/0058* (2013.01); *A61P 25/00* (2018.01); *C07K 14/47* (2013.01); *C12N 15/113* (2013.01); *C12N 15/79* (2013.01); *C12N 2310/141* (2013.01); *C12N 2310/531* (2013.01); *C12N 2320/32* (2013.01); *C12N 2330/51* (2013.01); *C12N 2750/14143* (2013.01)

(58) Field of Classification Search
None
See application file for complete search history.

(56) References Cited

U.S. PATENT DOCUMENTS

| 4,962,091 | A | 10/1990 | Eppstein et al. |
| 5,350,674 | A | 9/1994 | Boenisch et al. |
| 5,585,362 | A | 12/1996 | Schwarz et al. |
| 6,855,314 | B1* | 2/2005 | Chiorini ................. C12N 15/86 424/93.1 |
| 8,258,286 | B2 | 9/2012 | Davidson et al. |
| 8,299,215 | B2 | 10/2012 | Davidson et al. |
| 8,329,890 | B2 | 12/2012 | Davidson et al. |
| 8,481,710 | B2 | 7/2013 | Davidson et al. |
| 8,487,088 | B2 | 7/2013 | Davidson et al. |
| 8,524,879 | B2 | 9/2013 | Davidson et al. |
| 8,524,881 | B2 | 9/2013 | Davidson et al. |
| 8,691,948 | B2 | 4/2014 | Davidson et al. |
| 8,779,116 | B2 | 7/2014 | Davidson et al. |
| 2002/0037281 | A1 | 3/2002 | Davidson et al. |
| 2014/0356327 | A9 | 12/2014 | Passini et al. |

FOREIGN PATENT DOCUMENTS

| WO | 1994007529 A1 | 4/1994 |
| WO | 2012109667 A1 | 8/2012 |
| WO | 2013172964 A1 | 11/2013 |
| WO | 2014186579 A1 | 11/2014 |

OTHER PUBLICATIONS

Lentz et al. (Neurobiol Dis. Nov. 2012;48(2):179-88 (Year: 2012).*
Bouard et al. (Br J Pharmacol. May 2009; 157(2): 153-65.) (Year: 2009).*
Chen et al. (J Neurosurg. Aug. 2005;103(2):311-9 (Year: 2005).*
Torashima et al (Brain Research, 1082, 11-12, 2006 (Year: 2006).*
Krauss (Journal of Molecular Biology, (2019) 431: 1729-1742) (Year: 2019).*
Dong (Frontiers in Molecular Neuroscience, 12: 1-11, 2019) (Year: 2019).*
Murmann (Trends Cancer, 4(10): 684-700, 2018) (Year: 2018).*
Koscianska (Cerebellum & Ataxias, 1(7); 1-10, 2014) (Year: 2014).*
Basu, et al., "Silencing of end-joining repair for efficient site-specific gene insertion after TALEN/CRISPR mutagenesis in Aedes aegypti", Proc Natl Acad Sci U S A 112(13), 4038-4043 (2015).
Davidson, et al., "Viral Vectors for Gene Delivery to the Nervous System", Nat Rev. 4(5), 353-364 (2003).
Donato, et al., "Spinocerebellar ataxia type 1", Handb Clin Neurol 103, 399-421 (2012).
Keiser, et al., "Broad Therapeutic Beneit After RNAi Expression Vector Delivery to Deep Cerebellar Nuclei: Implications for Spinocerebellar Ataxia Type 1 Therapy", The American Society of Gene and Cell Therapy 22(3), 588-595 (2014).
Keiser, et al., "RNAi or overexpression: Alternative therapies for Spinocerebellar Ataxia Type 1", Neurobiol Dis 56, 6-13 (2013).

(Continued)

Primary Examiner — Anoop K Singh
Assistant Examiner — Magdalene K Sgagias
(74) Attorney, Agent, or Firm — Viksnins Harris Padys Malen LLP

(57) ABSTRACT

The present disclosure provides methods of treating a disease or delivering a therapeutic agent to a mammal comprising administering to the mammal's deep cerebella nuclei a recombinant adeno-associated virus (rAAV) particle comprising an AAV capsid protein and a vector comprising a nucleic acid encoding a therapeutic agent inserted between a pair of AAV inverted terminal repeats in a manner effective to infect the CNS cell of the non-rodent mammal such that the CNS cell expresses the therapeutic agent in the non-rodent mammal.

12 Claims, 23 Drawing Sheets
Specification includes a Sequence Listing.

(56) References Cited

OTHER PUBLICATIONS

Kole, et al., "RNA therapeutics: Beyond RNA interference and antisense oligonucleotides", Nat Rev Drug Discov 11(2), 125-140 (2011).
McBride, et al., "Artificial miRNAs mitigate shRNA-mediated toxicity in the brain: Implications for the therapeutic development of RNAi", Proc Natl Acad Sci U S A 105, 5868-5873 (2008).
McBride, et al., "Preclinical Safety of RNAi-Mediated HTT Suppression in the Rhesus Macaque as a Potential Therapy for Huntington's Disease", Molecular Therapy 19 (12), 2152-2162 (2011).
Monteys, et al., "Single nucleotide seed modification restores in vivo tolerability of a toxic artificial miRNA sequence in the mouse brain", Nucleic Acids Res 42 (21), 13315-13327 (2014).
Ousterout, et al., "Multiplex CRISPR/Cas9-Based Genome Editing for Correction of Dystrophin Mutations that Cause Duchenne Muscular Dystrophy", Nat Commun 6, 6244 (2015).
Oz, et al., "Neurochemical Alterations in Spinocerebellar Ataxia Type 1 and Their Correlations With Clinical Status", Mov Disord 25(9), 1253-1261 (2010).
Oz, et al., "Noninvasive Detection of Pre-Symptomatic and Progressive Neurodegeneration in a Mouse Model of Spinocerebellar Ataxia Type 1", J Neurosci 30(10), 3831-3838 (2010).
Patent Cooperation Treaty, International Searching Authority, Search Report and Written Opinion for PCT/US2016/035087, 10 pages, dated Sep. 13, 2016.
Robitaille, et al., "Structural and immunocytochemical features of olivopontocerebellar atrophy caused by the spinocerebellar ataxia type 1 (SCA-1) mutation define a unique phenotype", Acta Neuropathol 90(6), 572-581 (1995).
Rub, et al., "Clinical features, neurogenetics and neuropathology of the polyglutamine spinocerebellar ataxias type 1, 2, 3, 6 and 7", Prog Neurobiol 104, 38-66 (2013).
Rub, et al., "Spinocerebellar ataxia type 1 (SCA1): new pathoanatomical and clinico-pathological insights", Neuropathol Appl Neurobiol 38(7), 665-680 (2012).
Watson, et al., "Intrathecal Administration of AAV Vectors for the Treatment of Lysosomal Storage in the Brains of MPS I Mice", Gene Therapy 13, 917-925 (2006).
Wood, et al., "Targeted Genome Editing Across Species Using ZFNs and TALENs", Science 333(6040), 307 (2011).
Xia, et al., "RNAi suppresses polyglutamine-induced neurodegeneration in a model of spinocerebellar ataxia", Nature Medicine 10(8), 816-820 (2004).
Xia, et al., "siRNA-mediated gene silencing in vitro and in vivo", Nat Biotechnol 20(10), 1006-1010 (2002).
Zu, et al., "Recovery from Polyglutamine-Induced Neurodegeneration in Conditional SCA1 Transgenic Mice", J Neurosci 24(40), 8853-8861 (2004).

\* cited by examiner

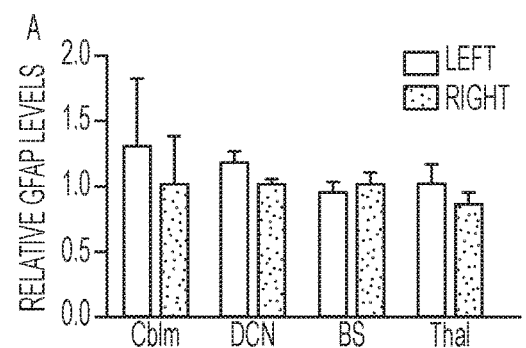
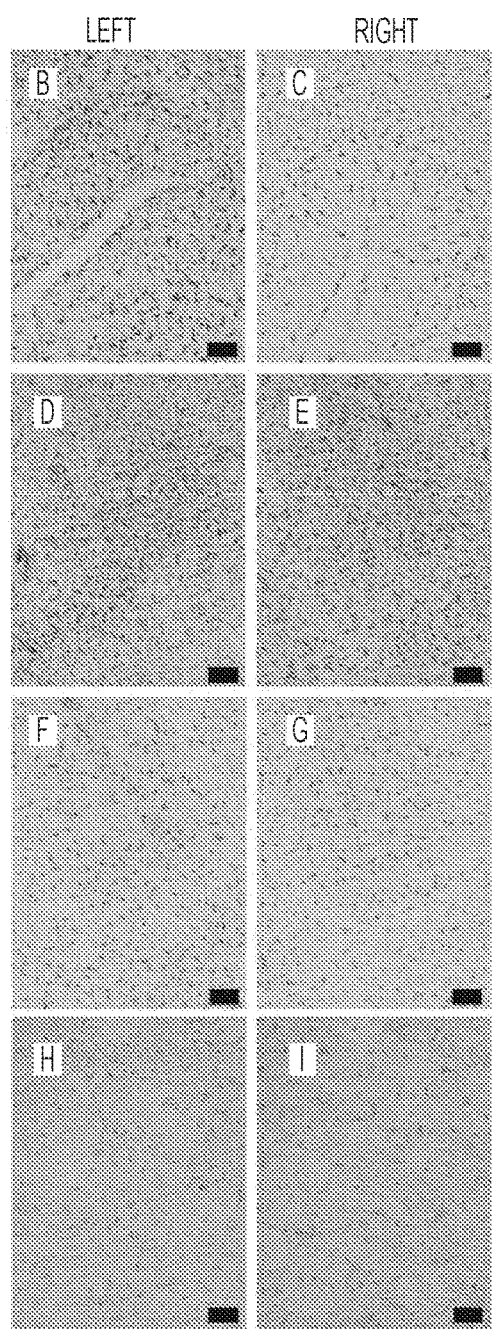
FIG. 6A-6I

5'-
GCTATCCCAGGTTGCCTTGGTTCTTGGCAATTGGGAAATTAAGAGGGCAGAGAGAATTTGAACAGAAACTGTTCT
AATATTGGTCTTTTTATTGTGTAAGTATTGTTCTTTGGTAAACCTCCTTCTTTTGGTTTCCAGGAATTGCTGGACACA
GTGGCTTGGTGTGTGTCTGAGGACTGTAGGCCTTGGCCCTAGGTTGTGGTTTTAGGTCTCAGGTGCTCTTCCTG
GCTGTCTCCTTGCTTCTTTCCCTTGTCCTCTTCTTTGTTTCCAGCCTTTTCTCCCTTTTGCTTAAGTTGGTGCAGC
AGGGTTTGGCTGCTCTCAGATTCCTGCTTCCTCAGTTGCTGTAGTTGTCAGGCCCAGAAGGCTGGCAGAAGGAT
CAGGATCTGGCTAGGTTTGCTCTCACTGTGGCAGAGTAGGGGGAGGAGGAGAGCAAAAGTGACCCCAGGCCAG
CTGTAGGGAGCTTAGGCTTGGTCAACCAGCCTTCAGGTCCTAGACTTTGTCTTCTCTTGAGTTTGGCTGTGTGTG
TTTGGTGGGAACTAGGTTCTACTTAGCCCAAGAAATTGGGCACTTTTTGCTTGTGGTTTCTGTAGAGAATTGCACT
GGGTATCTGACTTAGCCTGGCAGCTTGCCTCCCTCAGGTAGGTTAGTCTCAGGAAGTGAAGCAAAGTCCAGCAA
GAACTTCTTTTGTGGCTTAAAGTCTCAATTCTGTGAGGTGCTGGCAAATCACCACCACAATCAAGAGGCTGAAGT
GATTTTTGTCTAGGGAGGCAGGAAAGGCTTCCTGGAGTCAGCAGCCAGTAGGTGAAAGAGTAGATTGGAGACCT
TCTTAATCTTCACAACCTCTTGTCTCAAGGGGTGCCAGGAAGCTGTGGAGGCTGAACCCTTCTTTTGCTGCCAGA
GAGTGGGACACCTTGAGGGTCAGGTCAAGGGGTTGTACCTTGTTTGGTAGAGAATTAGGGGCTCTTGAAGACTT
TGGTTGTGGTCAGGGGAGTGTATCTTTTAGGAAGAGTGACCAAGTGAGGAAGGGTAGAGGAGGACAGGTGGGA
GGGAGTCCAGGTGGGAGTGAGTAGACCCAGCAGGAGTGCAGGGCCTAAAGCCAGGTTGGTGGCAGGGCTGTG
AGGAGAGGCAGCCACCTGTGTGTCTGAAGAAGCAGGGGCAAGAGGGAAGAGGCCAGCAGACTGCCTTCACCC
AGAAACTGGAATAGATTGTGAGAGACCTTTCCCTGCTCTTAGGAGGGCTGAGTTCCAGTCCTCTCTTGTTATAC
AAGGGGCTTGGTATTTGTTTACAAAAGGGGTGTAAAGCTAGGGCAAGGTTTGATAAGGCTTCTAGGGGTATTTAA
GAAGTATTGTTGGGGTAATTGTTTGTCCAATTAACTTTGCTCTTGGAAGGACTTTCAGTACAAACTGCAACAACAG
GATTAGGAAGGGAAAATTTCTGAGTTGGGGTTACTCCTCAGAATTTCCCAGATTGTGATCTGGTTTTGATTTTCAA
GCTTGCTGACCCAATAGGTTAACCCACAAGTTTTAACCAGACCTTCTCAGTCCACTTACTTCAACTGCCCTTGCC
AAAGTCCAAGAGATCTTAAACTGTTGTTTGGCACAGCTTCCTCCCTCTTGGGTGGGCAAGCTTTTGGAAGAGAAG
GCTCCTTTGGGTGAGAGTGGGCACCAAAGTCTTCCCTGTCCCTTCCCCTAGCTTGAGAAGCCCTTCTCTATTGT
GGACTTTGTGCAATTAGCTTAATTACTAGCTTGAAGTTGACCTTCTGGAAATACTTTCTGGTTTAGCCTCACAAGT
GAGCAAGGAGGGTTGAGAGTTGTGCTGTGAGGATTGTGGGGCCCCAGCTGGCAGCAGGCTCTGGGTCAGGGG
GGCAGGGACCAAAGGCTTACCTGACAGTGAGGAGGGGTCTAGTAGGGGATCAGTTCCCCTGTTGTTCTTTAGAA
CCTTCTGGATATTCTTCTTCCCTGATTGGGGTTGTGAACAATAGAATCAACTTCTACTTGTAGATTGATTTAGGG
AGAACTTATACCTCAGTTGTTAAGTCACCCTGTCCAGATTGTGGGTTGCTTTCCTATTTGTTCAGAACTTTCCCAA
TTACCTCAGAAGCACTTGAAATTTAAAGGATTTTAACCCCAACTTAGGGATTATTTCACTTAGCTCTTGCACTTTTC
TTGATAATTGAATCCTCAGGTATTCCTCTGTTTGGGTTACTAATAGTTACTTCTTTTGGGGGGTTTTCCCCTGAA
AATCTTTTATCCCCAATTTGTGGCTTACCCTCTGAAGGTTGTTTGATAATTTTGGAAGATTTGAAAGTCTTCTTATT
TTACAAGGTTTGGGGTCTCTTTAAGCTGCTTGGTTCTCTTGTCAGCTCCCAAAGCAGAAGAAAGCTAGCTGAAAA
TTGCAATAGAGAAGATACTTCTTTTCCACCTGTTTTCAACTCTTATCTTCTTGAATTTCAGGGCACCTTTTCCTTGCT
CCTAGTGCTTGCTATCTGTTTATTATTTTCCTTCCTGAATACCCTGAACTCCAGCTTGTTCTGCTGTAATTCTGGC
CTCCCTGGCTTCTTGGACTCCTGTTTCCTTTGCTCTGTCTTCCCCCAAGTCAGCTCCTGCTGAACAGCTTCTCAG
CTGAAGTGAACCTGGAGTGCCTGGATCTTGCTGGATCTTTGAGTATTGCCTCTGGGGTCCTTGGTTCCTTCTGCT
GAGTTGCTCAGAATCTCCACTCCCCAACCTTGTGTGGCCCTTCCTGCACTCCTCTGATTCCCCTTGTCTTCCCT
GGTTTCTTGCTTTGGTTTAAAGTCTCCACAGAACTTTTGCAGCTCTTCTGAAGACCTGGAAGCTTTTTCTTCTTAAT
TCTCTTCTCTTGACCTCTTTTCCCTTCTTTGAGAGCTAGAACTTCCCTTGGTGAACTTCTCTTTCCAGAATTACTTG
CCTTCTTTTCCCTCCCACTTACCTGTTGTCCAGGAGAGGTCAGATTGCTGTGCTTATTGGAGGAGAACCCTTTCT
TCCCTGGGCTCTTCTTCTCACTTGACTTCACCACTTCACCTAATTCCTTGGACCCTCAGTGGTGTCACTGCTGGA
TTTTTCTTTCCTTTGGCTGGCCTTAGGGCACACCCAGGTTGACTAGAATAGTCTTGGTATTTAGATCCACTCACTT
TTTCAGTTTCTGTGTCTGTCTCTTGCCTGCTTCTGACTTAACCCAGAGAAAGCTTCTCTTTCACAAGGGTTCTTAG
ATTTTTGTTCACTGAGCACCTTCTTTTCTGAGGCAGTGTTTTACCAATAGGGGTTTTCCTAGTCAGTCTAACCTTA
CCTTTCTTGTTGGGCTTGTCTTTGGTCCTGACCCTTTCTCTGAGTCTGTAACCCAGAATTGCTGTATAACCCAATT
ACTTGAAATCCTTTAGAATCTTAACACTTCTTACACCTGATTTCCCCTTTTATTGTATCCAAATTGAACCAACCCTT
TGTGAATTTGACAGTGATTTCTCCCAGGGATCCTAGTGTATAAGGAATAGGACTTAGTATTTTCTATTGGGGATA
TACCACTTACCAGATACTGATTTTGTTGGACTTTTAACCCTTTTTTCTCTTTTTGAAAGAAAGTTAGGAATTATTTCT
TCCAGTAGAACCAGTGTAACCTGAAAGCCTTTGAAAGAGTAGTTTGGGTATAGCTATCTGAAAGGAATTTCTTTC
CAAGGGATTTCCCCAGTGCTGACAACAAACAAACAGACACACCCTGCAAGGTGAGTGTAAAGAACACTAGAGCA
AGGC-3' (SEQ ID NO: 13)

FIG. 21

| | |
|---|---|
| pKFBextmU6miS1newStfr | 11591 bp DNA circular |
| T7n Right | 2466..2690 |
| Gentamicin Resistance | complement 2757..3290 |
| ITR 119bp | 3858..3976 |
| ITR 130bp | 8327..8456 |
| Z zuvgt phage genes | 8632..9617 |
| H phage gene H | 9618..11058 |
| SV40snip | 11081..11215 |
| Tn7 Left | 11244..11398 |
| KanR (9333-10145) | complement(587..1399) |
| New stuffer sequence | 4513..8286 |
| SnaBI | 8287..8292 |
| RNAi expression cassette | 4030..4512 |
| mouse U6 promoter | 4036..4346 |
| 5-end Pri-miRNA | 4346..4379 |
| 3-end Pri-miRNA | 4466..4512 |
| miS1 | 4380..4465 |
| pKFBextmU6miS1newStfr | 1..11591 |

```
   1 GACGCGCCCT GTAGCGGCGC ATTAAGCGCG GCGGGTGTGG TGGTTACGCG CAGCGTGACC
  61 GCTACACTTG CCAGCGCCCT AGCGCCCGCT CCTTTCGCTT TCTTCCCTTC CTTTCTCGCC
 121 ACGTTCGCCG GCTTTCCCCG TCAAGCTCTA AATCGGGGGC TCCCTTTAGG GTTCCGATTT
 181 AGTGCTTTAC GGCACCTCGA CCCCAAAAAA CTTGATTAGG GTGATGGTTC ACGTAGTGGG
 241 CCATCGCCCT GATAGACGGT TTTTCGCCCT TTGACGTTGG AGTCCACGTT CTTAATAGTG
 301 GACTCTTGTT CCAAACTGGA ACAACACTCA ACCCTATCTC GGTCTATTCT TTTGATTTAT
 361 AAGGGATTTT GCCGATTTCG GCCTATTGGT TAAAAAATGA GCTGATTTAA CAAAAATTTA
 421 ACGCGAATTT TAACAAAATA TTAACGCTTA CAATTTAGGT GGCACTTTTC GGGGAAATGT
 481 GCGCGGAACC CCTATTTGTT TATTTTTCTA AATACATTCA AATATGTATC CGCTCATGAG
 541 ACAATAACCC TGATAAATGC TTCAATAATA TTGAAAAAGG AAGAGTatga gccatattca
 601 acgggaaacg tcttgctcga agccgcgatt aaattccaac atggatgctg atttatatgg
 661 gtataaatgg gctcgcgata atgtcgggca atcaggtgcg acaatctatc gattgtatgg
 721 gaagcccgat gcgccagagt tgtttctgaa acatggcaaa ggtagcgttg ccaatgatgt
 781 tacagatgag atggtcagac taaactggct gacggaattt atgcctcttc cgaccatcaa
 841 gcattttatc cgtactcctg atgatgcatg ttactcacc actgcgatcc ccgggaaaac
 901 agcattccag gtattagaag aatatcctga ttcaggtgaa atattgttg atgcgctggc
 961 agtgttcctg cgccggttgc attcgattcc tgtttgtaat tgtcctttta acagcgatcg
1021 cgtatttcgt ctcgctcagg cgcaatcacg aatgaataac ggtttggttg atgcgagtga
1081 ttttgatgac gagcgtaatg gctggcctgt tgaacaagtc tggaaagaaa tgcataagct
1141 tttgccattc tcaccggatt cagtcgtcac tcatggtgat ttctcacttg ataaccttat
1201 tttgacgag gggaaattaa taggttgtat tgatgttgga cgagtcggaa tcgcagaccg
1261 ataccaggat cttgccatcc tatggaactg cctcggtgag ttttctcctt cattacagaa
1321 acggcttttt caaaaatatg gtattgataa tcctgatatg aataaattgc agtttcattt
1381 gatgctcgat gagttttct aaCTGTCAGA CCAAGTTTAC TCATATATAC TTTAGATTGA
1441 TTTAAAACTT CATTTTTAAT TTAAAAGGAT CTAGGTGAAG ATCCTTTTTG ATAATCTCAT
1501 GACCAAAATC CCTTAACGTG AGTTTTCGTT CCACTGAGCG TCAGACCCCG TAGAAAAGAT
1561 CAAAGGATCT TCTTGAGATC CTTTTTTTCT GCGCGTAATC TGCTGCTTGC AAACAAAAAA
1621 ACCACCGCTA CCAGCGGTGG TTTGTTTGCC GGATCAAGAG CTACCAACTC TTTTTCCGAA
1681 GGTAACTGGC TTCAGCAGAG CGCAGATACC AAATACTGTT CTTCTAGTGT AGCCGTAGTT
1741 AGGCCACCAC TTCAAGAACT CTGTAGCACC GCCTACATAC CTCGCTCTGC TAATCCTGTT
1801 ACCAGTGGCT GCTGCCAGTG GCGATAAGTC GTGTCTTACC GGGTTGGACT CAAGACGATA
1861 GTTACCGGAT AAGGCGCAGC GGTCGGGCTG AACGGGGGGT TCGTGCACAC AGCCCAGCTT
1921 GGAGCGAACG ACCTACACCG AACTGAGATA CCTACAGCGT GAGCTATGAG AAAGCGCCAC
1981 GCTTCCCGAA GGGAGAAAGG CGGACAGGTA TCCGGTAAGC GGCAGGGTCG GAACAGGAGA
```

FIG. 22A

```
2041 GCGCACGAGG GAGCTTCCAG GGGGAAACGC CTGGTATCTT TATAGTCCTG TCGGGTTTCG
2101 CCACCTCTGA CTTGAGCGTC GATTTTTGTG ATGCTCGTCA GGGGGGCGGA GCCTATGGAA
2161 AAACGCCAGC AACGCGGCCT TTTTACGGTT CCTGGCCTTT TGCTGGCCTT TTGCTCACAT
2221 GTTCTTTCCT GCGTTATCCC CTGATTCTGT GGATAACCGT ATTACCGCCT TTGAGTGAGC
2281 TGATACCGCT CGCCGCAGCC GAACGACCGA GCGCAGCGAG TCAGTGAGCG AGGAAGCGGA
2341 AGAGCGCCTG ATGCGGTATT TTCTCCTTAC GCATCTGTGC GGTATTTCAC ACCGCATAGA
2401 CCAGCCGCGT AACCTGGCAA AATCGGTTAC GGTTGAGTAA TAAATGGATG CCCTGCGTAA
2461 GCGGGTGTGG GCGGACAATA AAGTCTTAAA CTGAACAAAA TAGATCTAAA CTATGACAAT
2521 AAAGTCTTAA ACTAGACAGA ATAGTTGTAA ACTGAAATCA GTCCAGTTAT GCTGTGAAAA
2581 AGCATACTGG ACTTTTGTTA TGGCTAAAGC AAACTCTTCA TTTTCTGAAG TGCAAATTGC
2641 CCGTCGTATT AAAGAGGGGC GTGGCCAAGG GCATGGTAAA GACTATATTC GCGGCGTTGT
2701 GACAATTTAC CGAACAACTC CGCGGCCGGG AAGCCGATCT CGGCTTGAAC GAATTGTTAG
2761 GTGGCGGTAC TTGGGTCGAT ATCAAAGTGC ATCACTTCTT CCCGTATGCC CAACTTTGTA
2821 TAGAGAGCCA CTGCGGGATC GTCACCGTAA TCTGCTTCA CGTAGATCAC ATAAGCACCA
2881 AGCGCGTTGG CCTCATGCTT GAGGAGATTG ATGAGCGCGG TGGCAATGCC CTGCCTCCGG
2941 TGCTCGCCGG AGACTGCGAG ATCATAGATA TAGATCTCAC TACGCGGCTG CTCAAACTTG
3001 GGCAGAACGT AAGCCGCGAG AGCGCCAACA ACCGCTTCTT GGTCGAAGGC AGCAAGCGCG
3061 ATGAATGTCT TACTACGGAG CAAGTTCCCG AGGTAATCGG AGTCCGGCTG ATGTTGGGAG
3121 TAGGTGGCTA CGTCTCCGAA CTCACGACCG AAAAGATCAA GAGCAGCCCG CATGGATTTG
3181 ACTTGGTCAG GGCCGAGCCT ACATGTGCGA ATGATGCCCA TACTTGAGCC ACCTAACTTT
3241 GTTTTAGGGC GACTGCCCTG CTGCGTAACA TCGTTGCTGC TGCGTAACAT CGTTGCTGCT
3301 CCATAACATC AAACATCGAC CCACGGCGTA ACGCGCTTGC TGCTTGGATG CCCGAGGCAT
3361 AGACTGTACA AAAAAACAGT CATAACAAGC CATGAAAACC GCCACTGCGC CGTTACCACC
3421 GCTGCGTTCG GTCAAGGTTC TGGACCAGTT GCGTGAGCGC ATACGCTACT TGCATTACAG
3481 TTTACGAACC GAACAGGCTT ATGTCAACTG GGTTCGTGCC TTCATCCGTT TCCACGGTGT
3541 GCGTCACCCG GCAACCTTGG GCAGCAGCGA AGTCGAGGCA TTTCTGTCCT GGCTGGCGAA
3601 CGAGCGCAAG GTTTCGGTCT CCACGCATCG TCAGGCATTG GCGGCCTTGC TGTTCTTCTA
3661 CGGCAAGGTG CTGTGCACGG ATCTGCCCTG GCTTCAGGAG ATCGGAAGAC CTCGGCCGTC
3721 GCGGCGCTTG CCGGTGGTGC TGACCCCGGA TGAAGTGGTT CGCATCCTCG GTTTTCTGGA
3781 AGGCGAGCAT CGTTTGTTCG CCCAGGACTC TAGCTATAGT TCTAGTGGTT GGCTACAGCT
3841 TGCATGCCTG CAGGCAGCTG CGCGCTCGCT CGCTCACTGA GGCCGCCCGG GCGTCGGGCG
3901 ACCTTTGGTC GCCCGGCCTC AGTGAGCGAG CGAGCGCGCA GAGAGGGAGT GGCCAACTCC
3961 ATCACTAGGG GTTCCTTGTA GTTAATGATT AACCCGCCAT GCTACTTATC TACGTAGCCA
4021 TGCTCTAGTG AATTCGACGC CGCCATCTCT AGGCCCGCGC CGGCCCCCTC GCACAGACTT
4081 GTGGGAGAAG CTCGGCTACT CCCCTGCCCC GGTTAATTTG CATATAATAT TTCCTAGTAA
4141 CTATAGAGGC TTAATGTGCG ATAAAAGACA GATAATCTGT TCTTTTTAAT ACTAGCTACA
4201 TTTTACATGA TAGGCTTGGA TTTCTATAAG AGATACAAAT ACTAAATTAT TATTTTAAAA
4261 AACAGCACAA AAGGAAACTC ACCCTAACTG TAAAGTAATT GTGTGTTTTG AGACTATAAA
4321 TATCCCTTGG AGAAAAGCCT TGTTTGCGTT TAGTGAACCG TCAGATGGTA CCGTTTAAAC
4381 TCGAGTGAGC GCAGCAACGA CCTGAAGATC GATCCGTAAA GCCACAGATG GGGTCGATCT
4441 TCAGGTCGTT GCTTCGCCTA CTAGAGCGGC CGCCACAGCG GGAGATCCA GACATGATAA
4501 GATACATTTT TTGAATTCAG GCTATCCCAG GTGCCTTGG TTCTTGGCAA TTGGGAAATT
4561 AAGAGGGCAG AGAGAATTTG AACAGAAACT GTTCTAATAT TGGTCTTTTA TTGTGTAAGT
4621 ATTGTTCTTT ggTAAACCTC CTTCTTTTgg TTTCCAGGAA TTGCTGGACA CAGTGGCTTG
4681 GTGTGTGTCT GAGGACTGTA GGCCTTGGCC CTAGGTTGTG GTTTTAGGTC TCAGGTGCTC
4741 TTCCTGGCTG TCTCCTTGCT TCTTTCCCTT GTCCTCTTCT TTGTTTCCAG CCTTTTCTCC
4801 CTTTTGCTTA AGTTTGGTGC AGCAGGGTTT GGCTGCTCTC AGATTCCTGC TTCCTCAGTT
4861 GCTGTAGTTG TCAGGCCCAG AAGGCTGGCA GAAGGATCAG GATCTGGCTA GGTTTGCTCT
4921 CACTGTGGCA GAGTAGGGGG AGGAGGAGAG CAAAAGTGAC CCCAGGCCAG CTGTAGGGAG
4981 CTTAGGCTTG GTCAAccAGC CTTCAGGTCC TAGACTTTGT CTTCTCTTGA GTTTGGCTGT
5041 GTGTGTTTGG TGggAACTAG GTTCTACTTA GCCCAAGAAA TTGGGCACTT TTTGCTTGTG
5101 GTTTCTGTAG AGAATTGCAC TGGGTATCTG ACTTAGCCTG GCAGCTTGCC TCCCTCAGGT
5161 AGGTTAGTCT CAGGAAGTGA AGCAAAGTCC AGCAAGAACT TCTTTTGTGT CTTAAAGTCT
5221 CAATTCTGTG AGGTGCTGGC AAATCACCAC CACAATCAAG AGGCTGAAGT GATTTTTGTC
5281 TAGGGAGGCA GGAAAGGCTT CCTGGAGTCA GCAGCCAGTA GGTGAAAGAG TAGATTGGAG
5341 ACCTTCTTAA TCTTCACAAC CTCTTGTCTC AAGGGGTGCC AGGAAGCTGT GGAGGCTGAA
5401 CCCTTCTTTT GCTGCCAGAG AGTGGGACAC CTTGAGGGTC AGGTCAAGGG GTTGTACCTT
```

FIG. 22B

```
5461 GTTTGGTAGA GAATTAGGGG CTCTTGAAGA CTTTGGTTGT GGTCAGGGGA GTGTATCTTT
5521 TAGGAAGAGT GACCAAGTGA GGAAGGGTAG AGGAGGACAG GTGGGAGGGA GTCCAGGTGG
5581 GAGTGAGTAG ACCCAGCAGG AGTGCAGGGC CTAAAGCCAG GTTGGTGGCA GGGCTGTGAG
5641 GAGAGGCAGC CACCTGTGTG TCTGAAGAAG CAGGGGCAAG AGGGAAGAGG CCAGCAGACT
5701 GCCTTCACCC AGAAACTGGA ATAGATTGTG AGAGACCTTT CCCTGCTCTT AGGAGGGGCT
5761 GAGTTccAGT ccTCTCTTGT TATACAAggg GCTTGGTATT TGTTTACAAA AgggGTGTAA
5821 AGCTAgggCA AGGTTTGATA AGGCTTCTAG gggTATTTAA GAAGTATTGT TGgggTAATT
5881 GTTTGTCCAA TTAACTTTGC TCTTggAAGG ACTTTCAGTA CAAACTGCAA CAACAGGATT
5941 AGGAAgggAA AATTTCTGAG TTGgggTTAC TCCTCAGAAT TTCCCAGATT GTGATCTGGT
6001 TTTGATTTTC AAGCTTGCTG ACCCAATAGG TTAACCACA AGTTTTAAcc AGACCTTCTC
6061 AGTCCACTTA CTTCAACTGC CCTTGCCAAA GTccAAGAGA TCTTAAACTG TTGTTTGGCA
6121 CAGCTTCCTC CCTCTTGGGT GGGCAAGCTT TTGGAAGAGA AGGCTCCTTT GGGTGAGAGT
6181 GGGGCACCAA AGTCTTCCCT GTCCCTTCCC CTAGCTTGAG AAGCCCTTCT CTATTGTGGA
6241 CTTTGTGCAA TTAGCTTAAT TACTAGCTTG AAGTTGACCT TCTGGAAATA CTTTCTGGTT
6301 TAGCCTCACA AGTGAGCAAG GAGGGTTGAG AGTTGTGCTG TGAGGATTGT GGGGCCCCAG
6361 CTGGCAGCAG GCTCTGGGTC AGGGGGGCAG GGACCAAAGG CTTACCTGAC AGTGAGGAGG
6421 GGTCTAGTAG GGGATCAGTT CCCCTGTTGT TCTTTAGAAc cTTCTGGATA TTCTTCTTcc
6481 cTGATTggGG GTTGTGAACA ATAGAATCAA CTTCTACTTG TAGATTGATT TAGGGAGAAC
6541 TTATACCTCA GTTGTTAAGT CACCCTGTCC AGATTGTGGG TTGCTTTCCT ATTTGTTCAG
6601 AACTTTccCA ATTACCTCAG AAGCACTTGA AATTTAAAGG ATTTTAAccc cAACTTAggG
6661 ATTATTTCAC TTAGCTCTTG CACTTTTCTT GATAATTGAA TCCTCAGGTA TTCCTCTGTT
6721 TggGTTACTA ATAGTTACTT CTTTTGGGgg ggTTTTCCCC TGAAAATCTT TTATCcccAA
6781 TTTGTGGCTT AcccTCTGAA GGTTGTTTGA TAATTTTGGA AGATTTGAAA GTCTTCTTAT
6841 TTTACAAGGT TTGGGGTCTC TTTAAGCTGC TTGGTTCTCT TGTCAGCTCC CAAAGCAGAA
6901 GAAAGCTAGC TGAAAATTGC AATAGAGAAG ATACTTCTTT TCCACCTGTT TTCAACTCTT
6961 ATCTTCTTGA ATTTCAGGGC ACCTTTCCTT GCTCCTAGTG CTTGCTATCT GTTTATTATT
7021 TTCCTTCCTG AATACCCTGA ACTCCAGCTT GTTCTGCTGT AATTCTGGCC TCCCTGGCTT
7081 CTTGGACTCC TGTTTCCTTT GCTCTGTCTT CCCccAAGTC AGCTCCTGCT GAACAGCTTC
7141 TCAGCTGAAG TGAAccTGGA GTGCCTGGAT CTTGCTGGAT CTTTGAGTAT TGCCTCTGGg
7201 gTCCTTGGTT CCTTCTGCTG AGTTGCTCAG AATCTCCACT CCCCcaacCT TGTGTGGCCC
7261 TTCCTGCACT CCTCTGATTC CccTTGTCTT CCCTGGTTTC TTGCTTTGGT TTAAAGTCTC
7321 CACAGAACTT TTGCAGCTCT TCTGAAGACC TGGAAGCTTT TTCTTCTTAA TTCTCTTCTC
7381 TTGACCTCTT TTCCCTTCTT TGAGAGCTAG AACTTCCCTT GGTGAACTTC TCTTTCCAGA
7441 ATTACTTGCC TTCTTTTCCC TCCCACTTAC CTGTTGTCCA GGAGAGGTCA GATTGCTGTG
7501 CTTATTGGAG GAGAACCCTT TCTTCCCTGG GCTCTTCTTC TCACTTGACT TCACCACTTC
7561 ACCTAATTCC TTGGACCCTC AGTGGTGTCA CTGCTGGATT TTTCTTTCCT TTGGCTGGCC
7621 TTAGGGCACA CCCAGGTTGA CTAGAATAGT CTTGGTATTT AGATCCACTC ACTTTTTCAG
7681 TTTCTGTGTC TGTCTCTTGC CTGCTTCTGA CTTAACCCAG AGAAAGCTTC TCTTTCACAA
7741 GGGTTCTTAG ATTTTTGTTC ACTGAGCACC TTCTTTTCTG AGGCAGTGTT TTACCAATAg
7801 gggTTTTCCT AGTCAGTCTA ACCTTACCTT TCTTGTTggG CTTGTCTTTG GTCCTGACCC
7861 TTTCTCTGAG TCTGTAAccc AGAATTGCTG TATAAccCAA TTACTTGAAA TCCTTTAGAA
7921 TCTTAACACT TCTTACACCT GATTccccT TTTATTGTAT CCAAATTGAA CCAACCCTTT
7981 GTGAATTTGA CAGTGATTTC TCCCAGGGAT CCTAGTGTAT AAGGAATAGG ACTTAGTATT
8041 TTCTATTggg gGATATACCA CTTACCAGAT ACTGATTTTG TTGGACTTTT AACCCTTTTT
8101 TCTCTTTTTTG AAAGAAAGTT AGGAATTATT TCTTCCAGTA GAACCAGTGT AACCTGAAAG
8161 CCTTTGAAAG AGTAGTTTgg GTATAGCTAT CTGAAAGGAA TTTCTTTCCA AgggATTTcc
8221 CCAGTGCTGA CAACAAACAA ACAGACACAC CCTGCAAGGT GAGTGTAAAG AACacTAGaG
8281 CAAGGCTACG TAGATAAGTA GCATGGCGGG TTAATCATTA ACTACAAGGA ACCCCTAGTG
8341 ATGGAGTTGG CCACTCCCTC TCTGCGCGCT GCTCGCTCA CTGAGGCCGG GCGACCAAAG
8401 GTCGCCCGAC GCCCGGGCTT TGCCCGGGCG GCCTCAGTGA GCGAGCGAGC GCGCAGCTGC
8461 CTGCAGGTCT GAGACAATAA CCCTGATAAA TGCTTCAATA ATGTAAGCTT GTCGAGAAGT
8521 ACTAGAGGAT CATAATCAGC CATACCACAT TTGTAGAGGT TTTACTTGCT TTAAAAAACC
8581 TCCCACACCT CCCCCTGAAC CTGAAACATA AAATGAATGC AATTGAGGCC TTAATTCTAG
8641 CCATAAAAGG TCTTGAGCAG GCCGTTGAAA ACCTCAGCCG TATCAGCAAA ACGGCGGTGC
8701 CTGGTGCCGC CGCAATGACC ATTAACCGCG TTGCTTCATC CGCGATAGCG CAGTCGGCGT
8761 CACAGGTTGC CCGTGAGACA AAGGTACGCC GGAAACTGGT AAAGGAAAGG GCCAGGCTGA
8821 AAAGGGCCAC GGTCAAAAAT CCGCAGGCCA GAATCAAAGT TAGCCGGGGG GATTTGCCCG
```

FIG. 22C

```
 8881 TAATCAAGCT GGGTAATGCG CGGGTTGTCC TTTCGCGCCG CAGGCGTCGT AAAAAGGGGC
 8941 AGCGTTCATC CCTGAAAGGT GGCGGCAGCG TGCTTGTGGT GGGTAACCGT CGTATTCCCG
 9001 GCGCGTTTAT TCAGCAACTG AAAAATGGCC GGTGGCATGT CATGCAGCGT GTGGCTGGGA
 9061 AAAACCGTTA CCCCATTGAT GTGGTGAAAA TCCCGATGGC GGTGCCGCTG ACCACGGCGT
 9121 TGAAACAAAA TAGTGAGCGG ATACGGCGTG AACGTCTTCC GAAAGAGCTG GGCTATGCGC
 9181 TGAAGCATCA ACTCACACTG GTAATAAAGC GTAGAAACAT ACTGAACCTC CGTGCAGCCG
 9241 TACTGGATGC ACTGGAGAAG CATGACACCG GGCGACGTT TTTTGATGGT CGCCCCGCTG
 9301 TTTTTGATGA GGCGGATTTT CCGGCAGTT CCGTTTATCT CACCGGCGCT GAATACACGG
 9361 GCGAAGAGCT GGACAGCGAT ACCTGGCAGG CGGAGCTGCA TATCGAAGTT TTCCTGCCTG
 9421 CTCAGGTGCC GGATTCAGAG CTGGATGCGT GGATGGAGTC CCGGATTTAT CCGGTGATGA
 9481 GCGATAGCCC GGCACTGTCA GATTTGATCA CCAGTATGGT GACCAGCGGC TATGACTACC
 9541 GGCGCGACGA TGATGCGGGC TTGTGGAGTT CAGCCGATCT GACTTATGTC ATTACCTATG
 9601 AAATGTCTCC ACGCTTATGA GCAGCAGACT CAACAGGACA AAAATCCGCA GCAGCAGAGC
 9661 GATACCGAAG CGTCACGGCT GAAATATACC GAAGAGGCGC AGAAGGCTTA CGAACGGCTG
 9721 AAGACGCCGC TGGAGAAATA TACCGCCCGT CAGGAAGAAC TGAACAAGGC ACTGAAAGAC
 9781 GGGAAAATCC TGAAGGCGGA TTACAACACG CTGATGGCGG CGGCGAAAAA GGATTATGAA
 9841 GCGACGCTGA AAAAGCCGAA ACAGTCCAGC GTGAAGGTGT CTGCGGGCGA TAGTCAGGAA
 9901 GACAGTGCTC ATGCTGCCCT GCTGACGCTT CAGGCAGAAC TCCTGACGCT GGAGAAGCAA
 9961 GCCGGAGCAA ATGAGAAAAT CAGCCAGCAG CGCCGGGATT TGTGGAAGGC GGAGAGTCAG
10021 TTCGCGGTAC TGGAGGAGGC GGCGCAACGT CGCCAGGTGT CTGCACAGGA GAAATCCCTG
10081 CTGGCGCATA AAGATGAGAC GCTGGAGTAC AAACGCCAGG TGGCTGCACT TGGCGACAAG
10141 GTTAGGTATC AGGAGCGCCT GAACGCGCTG GCGCAGCAGG CGGATAAATT CGCACAGCAG
10201 CAACGGGCAA AACGGGCCGC CATTGATGCG AAAAGCCGGG GGCTGACTGA CCGGCAGGCA
10261 GAACGGGAAG CCACGGAACA GCGCCTGAAG GAACAGTATG GCGATAATCC GCTGGCGCTG
10321 AATAACGTCA TGTCAGAGCA GAAAAAGACC TGGCGGCTG AAGACCAGCT TCGCGGGAAC
10381 TGGATGGCAG ACCTGAAGTC CGGCTGGAGT GAGTGGGAAG AGAGCGCCAC GGACAGTATG
10441 TCGCAGGTAA AAAGTGCAGC CACGCAGACC TTTGATGGTA TTGCACAGAA TATGGCGGCG
10501 ATGCTGACCG GCAGTGAGCA GAACTGGCGC AGCTTCACCC GTTCCGTGCT GTCCATGATG
10561 ACAGAAATTC TGCTTTAGCA GGCAATGGTG GGGATTGTCG GGAGTATCGG CAGCGCCATT
10621 GGCGGGGCTG TTGGTGGCGG CGCATCCGCG TCAGGCGGTA CAGCCATTCA GGCCGCTGCG
10681 GCGAAATTCC ATTTTGCAAC CGGAGGATTT ACGGGAACCG GCGGCAAATA TGAGCCAGCG
10741 GGGATTGTTC ACCGTGGTGA GTTTGTCTTC ACGAAGGAGG CAACCAGCCG GATTGGCGTG
10801 GGGAATCTTT ACCGGCTGAT GCGCGGCTAT GCCACCGGCG GTTATGTCGG TACACCGGGC
10861 AGCATGGCAG ACAGCCGGTC GCAGGCGTCC GGGACGTTTG AGCAGAATAA CCATGTGGTG
10921 ATTAACAACG ACGGCACGAA CGGGCAGATA GGTCCGGCTG CTCTGAAGGC GGTGTATGAC
10981 ATGGCCCGCA AGGGTGCCCG TGATGAAATT CAGACACAGA TGCGTGATGG TGGCCTGTTC
11041 TCCTGACCTC CACGATGAGG CGCGCCCAAT TGTTGTTGTT AACTTGTTTA TTGCAGCTTA
11101 TAATGGTTAC AAATAAAGCA ATAGCATCAC AAATTTCACA AATAAAGCAT TTTTTTCACT
11161 GCATTCTAGT TGTGGTTTGT CCAAACTCAT CAATGTATCT TATCATGTCT GGATCTGATC
11221 ACTGATATCG CCTAGGAGAT CCGAACCAGA TAAGTGAAAT CTAGTTCCAA ACTATTTTGT
11281 CATTTTTAAT TTTCGTATTA GCTTACGACG CTACACCCAG TTCCCATCTA TTTTGTCACT
11341 CTTCCCTAAA TAATCCTTAA AAACTCCATT TCCACCCCTC CCAGTTCCCA ACTATTTTGT
11401 CCGCCCACAG CGGGGCATTT TTCTTCCTGT TATGTTTTTA ATCAAACATC CTGCCAACTC
11461 CATGTGACAA ACCGTCATCT TCGGCTACTT TTTCTCTGTC ACAGAATGAA AATTTTTCTG
11521 TCATCTCTTC GTTATTAATG TTTGTAATTG ACTGAATATC AACGCTTATT TGCAGCCTGA
11581 ATGGCGAATG G(SEQ ID NO: 14)
```

FIG. 22D

METHODS OF DELIVERY OF TRANSGENES FOR TREATING BRAIN DISEASES

RELATED APPLICATION

This application claims the benefit of priority of U.S. Provisional Application Ser. No. 62/168,618 filed on May 29, 2015, which application is incorporated by reference herein.

FEDERAL GRANT SUPPORT

This invention was made with government support under R01NS045667 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 24, 2016, is named 17023_173WO1_SL.txt and is 23,720 bytes in size.

BACKGROUND

RNAi directs sequence-specific gene silencing by double-stranded RNA (dsRNA) which is processed into functional small inhibitory RNAs (~21 nt). In nature, RNAi for regulation of gene expression occurs primarily via small RNAs known as microRNAs (miRNAs). Mature microRNAs (~19-25 nucleotides) are processed from larger primary miRNA transcripts (pri-miRNAs) which contain stem-loop regions. Via a series of processing events catalyzed by the ribonucleases, Drosha and Dicer, the miRNA duplex region is liberated and a single strand (the antisense "guide" strand) is then incorporated into the RNA Induced Silencing Complex (RISC), thus generating a functional complex capable of base-pairing with and silencing target transcripts. The mode of target repression primarily depends upon the degree of complementarity; transcript cleavage typically requires a high-degree of base-pairing, whereas translational repression and mRNA destabilization occurs when small RNAs bind imperfectly to target transcripts (most often in the 3' UTR). Indeed for the latter, short stretches of complementarity—as little as 6 bp—may be sufficient to cause gene silencing.

Gene transfer is now widely recognized as a powerful tool for analysis of biological events and disease processes at both the cellular and molecular level. More recently, the application of gene therapy for the treatment of human diseases, either inherited (e.g., ADA deficiency) or acquired (e.g., cancer or infectious disease), has received considerable attention. With the advent of improved gene transfer techniques and the identification of an ever expanding library of defective gene-related diseases, gene therapy has rapidly evolved from a treatment theory to a practical reality.

Traditionally, gene therapy has been defined as a procedure in which an exogenous gene is introduced into the cells of a patient in order to correct an inborn genetic error. Although more than 4500 human diseases are currently classified as genetic, specific mutations in the human genome have been identified for relatively few of these diseases. Until recently, these rare genetic diseases represented the exclusive targets of gene therapy efforts. Accordingly, most of the NIH approved gene therapy protocols to date have been directed toward the introduction of a functional copy of a defective gene into the somatic cells of an individual having a known inborn genetic error. Only recently, have researchers and clinicians begun to appreciate that most human cancers, certain forms of cardiovascular disease, and many degenerative diseases also have important genetic components, and for the purposes of designing novel gene therapies, should be considered "genetic disorders." Therefore, gene therapy has more recently been broadly defined as the correction of a disease phenotype through the introduction of new genetic information into the affected organism.

In in vivo gene therapy, a transferred gene is introduced into cells of the recipient organism in situ that is, within the recipient. In vivo gene therapy has been examined in several animal models. Several recent publications have reported the feasibility of direct gene transfer in situ into organs and tissues such as muscle, hematopoietic stem cells, the arterial wall, the nervous system, and lung. Direct injection of DNA into skeletal muscle, heart muscle and injection of DNA-lipid complexes into the vasculature also has been reported to yield a detectable expression level of the inserted gene product(s) in vivo. Treatment of diseases of the central nervous system, e.g., inherited genetic diseases of the brain, remains an intractable problem. Examples of such are neurodegenerative diseases such as Spinocerebellar Ataxia Type 1 (SCAT, which is also called Ataxin-1). Thus, therapies for the CNS deficits need to be developed.

SUMMARY

The present invention provides in certain embodiments, a method of delivering a therapeutic agent to a central nervous system (CNS) cell of a non-rodent mammal, comprising administering to the mammal's deep cerebella nuclei a recombinant adeno-associated virus (rAAV) particle comprising an AAV capsid protein and a vector comprising a nucleic acid encoding a therapeutic agent inserted between a pair of AAV inverted terminal repeats in a manner effective to infect the CNS cell of the non-rodent mammal such that the CNS cell expresses the therapeutic agent in the non-rodent mammal.

The present invention provides in certain embodiments, a method of treating a disease in a non-rodent mammal comprising administering to the non-rodent mammal's deep cerebella nuclei a recombinant adeno-associated virus (rAAV) particle comprising an AAV capsid protein and a vector comprising a nucleic acid encoding a therapeutic agent inserted between a pair of AAV inverted terminal repeats in a manner effective to infect a central nervous system (CNS) cell of the non-rodent mammal, wherein the cell expresses the therapeutic agent so as to treat the disease.

The present invention provides in certain embodiments, a method of delivering a therapeutic agent to a central nervous system (CNS) cell of a non-rodent mammal, comprising administering to the non-rodent mammal's deep cerebella nuclei a recombinant adeno-associated virus (rAAV) particle comprising an AAV capsid protein and a vector comprising a nucleic acid encoding a therapeutic agent inserted between a pair of AAV inverted terminal repeats in a manner effective to infect the CNS cell of the non-rodent mammal such that the cell expresses the therapeutic agent in the non-rodent mammal.

The present invention provides in certain embodiments, a method of treating a disease in a mammal comprising administering to the non-rodent mammal's deep cerebella nuclei a recombinant adeno-associated virus (rAAV) particle comprising an AAV capsid protein and a vector comprising a nucleic acid encoding a therapeutic agent inserted between a pair of AAV inverted terminal repeats in a manner effective to infect a central nervous system (CNS) cell of the non-rodent mammal, wherein the cell expresses the therapeutic agent so as to treat the disease.

In certain embodiments, in a method described above, the CNS cell is a cerebellar Purkinje cell (PC), brainstem neuron, or thalamus cell.

In certain embodiments, in a method described above, the non-rodent mammal is a primate, horse, sheep, goat, pig, or dog. In certain embodiments, non-rodent mammal is a primate. In certain embodiments, the primate is human.

In certain embodiments, in a method described above, the therapeutic agent is a therapeutic nucleic acid. In certain embodiments, the therapeutic nucleic acid is an miRNA. In certain embodiments, the miRNA is an miSCA1. In certain embodiments, the miSCA1 encodes SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

In certain embodiments, in a method described above, the miRNA encodes a sequence that binds to SEQ ID NO:9, or encodes SEQ ID NO:11 or SEQ ID NO:12.

In certain embodiments, the therapeutic nucleic acid is a nucleic acid encoding an artificial miRNA comprising an AAV2/1 vector, a miRNA segment and a safe stuffer sequence.

In certain embodiments, the therapeutic nucleic acid is a nucleic acid encoding an artificial miRNA comprising at least 90% identity to SEQ ID NO:11 or SEQ ID NO:12 (miS1).

In certain embodiments, the artificial miRNA comprises at least 90%, 91%, 92%, 93%, 94%, 95%, 96%, 97%, 98%, 99% or 100% identity to SEQ ID NO: 14. In certain embodiments, the therapeutic nucleic acid is a nucleic acid encoding an artificial miRNA consisting of SEQ ID NO:14 (AAV2/1.miS1).

In certain embodiments, in a method described above, the disease is neurodegenerative disease. In certain embodiments, the neurodegenerative disease is Alzheimer's disease, Huntington's disease, ALS, hereditary spastic hemiplegia, primary lateral sclerosis, spinal muscular atrophy, Kennedy's disease, a polyglutamine repeat disease, or Parkinson's disease. In certain embodiments, the neurodegenerative disease is polyglutamine repeat disease. In certain embodiments, the polyglutamine repeat disease is a spinocerebellar ataxia (SCA1, SCA2, SCA3, SCA6, SCAT, or SCA17). In certain embodiments, the polyglutamine repeat disease is SCA1.

The present invention provides in certain embodiments, a method of using a vector containing an expression cassette described herein. In certain embodiments, the vector is an adeno-associated virus (AAV) vector. In certain embodiments, the AAV is AAV1, AAV2, AAV5, AAV6 and/or AAV9. In certain embodiments, the AAV is AAV2. In certain embodiments, the AAV is AAV2/1. Examples of such AAVs are found in Davidson et al., PNAS (2000) 97:3428-3432. In certain embodiments, the AAV is AAV2/1. In certain embodiments, the AAV is AAV2/5. As used herein, the term AAV2/1 is used to mean an AAV2 ITR and AAV1 capsid, the term AAV2/2 is an AAV2 ITR and AAV2 capsid, the term AAV2/4 is an AAV2 ITR and AAV4 capsid, etc. In certain embodiments, the AAV is AAV1, AAV2, AAV5, AAV6 and/or AAV9. In certain embodiments, the AAV is AAV1. In certain embodiments, the AAV is AAV2. In certain embodiments, the AAV is AAV5. In certain embodiments, the AAV is AAV6. In certain embodiments, the AAV is AAV8.

In certain embodiments, the AAV is an AAV9. In certain embodiments, the AAV is an AAVrh10.

In certain embodiments, the AAV capsid has at least 80% homology to any reference AAV serotype capsid protein VP1, VP2, and/or VP3, e.g., to a AAV1 capsid protein VP1, VP2, and/or VP3, or e.g., to a AAV2 capsid protein VP1, VP2, and/or VP3, or e.g., a AAV3 capsid protein VP1, VP2, and/or VP3, or e.g., a AAV4 capsid protein VP1, VP2, and/or VP3, or e.g., a AAV5 capsid protein VP1, VP2, and/or VP3, or e.g., a AAV6 capsid protein VP1, VP2, and/or VP3, or e.g., a AAV7 capsid protein VP1, VP2, and/or VP3, or e.g., a AAV8 capsid protein VP1, VP2, and/or VP3, or e.g., a AAV9 capsid protein VP1, VP2, and/or VP3, or e.g., a AAVrh10 capsid protein VP1, VP2, and/or VP3, or e.g., a AAVrh74 capsid protein VP1, VP2, and/or VP3.

In certain embodiments, the AAV capsid has 100% homology to any reference AAV serotype capsid protein VP1, VP2, and/or VP3, e.g., to a AAV1 capsid protein VP1, VP2, and/or VP3, or e.g., to a AAV2 capsid protein VP1, VP2, and/or VP3, or e.g., a AAV3 capsid protein VP1, VP2, and/or VP3, or e.g., a AAV4 capsid protein VP1, VP2, and/or VP3, or e.g., a AAV5 capsid protein VP1, VP2, and/or VP3, or e.g., a AAV6 capsid protein VP1, VP2, and/or VP3, or e.g., a AAV7 capsid protein VP1, VP2, and/or VP3, or e.g., a AAV8 capsid protein VP1, VP2, and/or VP3, or e.g., a AAV9 capsid protein VP1, VP2, and/or VP3, or e.g., a AAVrh10 capsid protein VP1, VP2, and/or VP3, or e.g., a AAVrh74 capsid protein VP1, VP2, and/or VP3.

In certain embodiments, for in vivo delivery, AAV virions are formulated into pharmaceutical compositions. In one embodiment, pharmaceutical compositions will comprise sufficient genetic material to produce a therapeutically effective amount of the siRNA of interest, i.e., an amount sufficient to reduce or ameliorate symptoms of the disease state in question or an amount sufficient to confer the desired benefit. The pharmaceutical compositions may also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

In certain embodiments, the rAAV is administered at a dose of about 1-5 ml of $1\times10^5$-$1\times10^{16}$ vg/ml. In certain embodiments, the rAAV is administered at a dose of about 1-3 ml of $1×10^7$-$1×10^{14}$ vg/ml. In certain embodiments, the rAAV is administered at a dose of about 1-2 ml of $1×10^8$-$1×10^{13}$ vg/ml.

It should be understood that more than one transgene could be expressed by the delivered viral vector. Alternatively, separate vectors, each expressing one or more different transgenes, can also be delivered to the CNS as described herein. Furthermore, it is also intended that the viral vectors delivered by the methods of the present invention be combined with other suitable compositions and therapies.

In certain embodiments, the therapeutic agent is administered in a single dose to the mammal's deep cerebella nuclei.

In certain embodiments, the cell expresses the therapeutic agent at a level that reduces Atxn1 mRNA level by at least 10% in the cerebellum, deep cerebella nuclei, brain stem (BS), and/or thalamus.

In certain embodiments, the cell expresses the therapeutic agent at a level that reduces Atxn1 mRNA level by at least 10-50% in the cerebellum, deep cerebella nuclei, brain stem (BS), and/or thalamus.

The present invention further provides a method of substantially silencing a target gene of interest or targeted allele for the gene of interest in order to provide a therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effects can be measured quantitatively by a physician or qualitatively by a patient afflicted with the disease state targeted by the siRNA. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect.

BRIEF DESCRIPTION OF THE DRAWINGS

FIGS. 6A-6I. AAVmiS1eGFP is well tolerated in NHP. (A) Expression of GFAP messenger RNA levels from punches taken from the left (white bars) hemisphere relative to the right (black bars) hemisphere for the cerebellar cortex (Cblm), dentate nuclei (DCN), and inferior olivary complex (BS). Expression levels from tissue punches taken from the ventral lateral thalamus (Thal) are shown relative to the left hemisphere. Results are shown as mean±SEM (n=6): Cblm: 1.0±0.03 (right) vs. 1.17±0.10 (left). Paired t-test, P=0.35; DCN: 1.0±0.38 (right) vs. 1.30±0.52 (left; injected side). Paired t-test, P=0.63; BS: 1.0±0.08 (right) vs. 0.94±0.09 (left). Paired t-test, P=0.63; Thal: 1.0±0.15 (left) vs. 0.84±0.11 (right). Paired t-test, P=0.40. (B-I) IBA1 immunostaining in the left and right cerebellar cortex (B, C); left and right DCN (D, E); left and right inferior olivary complex (F, G); and left and right thalamus (H, I). Scale Bar=100 µm.

FIG. 21. Stuffer sequence (SEQ ID NO:13).

FIGS. 22A-22D. Sequence for AAV2/1.miS1 with safe "stuffer" sequence (SEQ ID NO:14).

DETAILED DESCRIPTION

Figure 1:
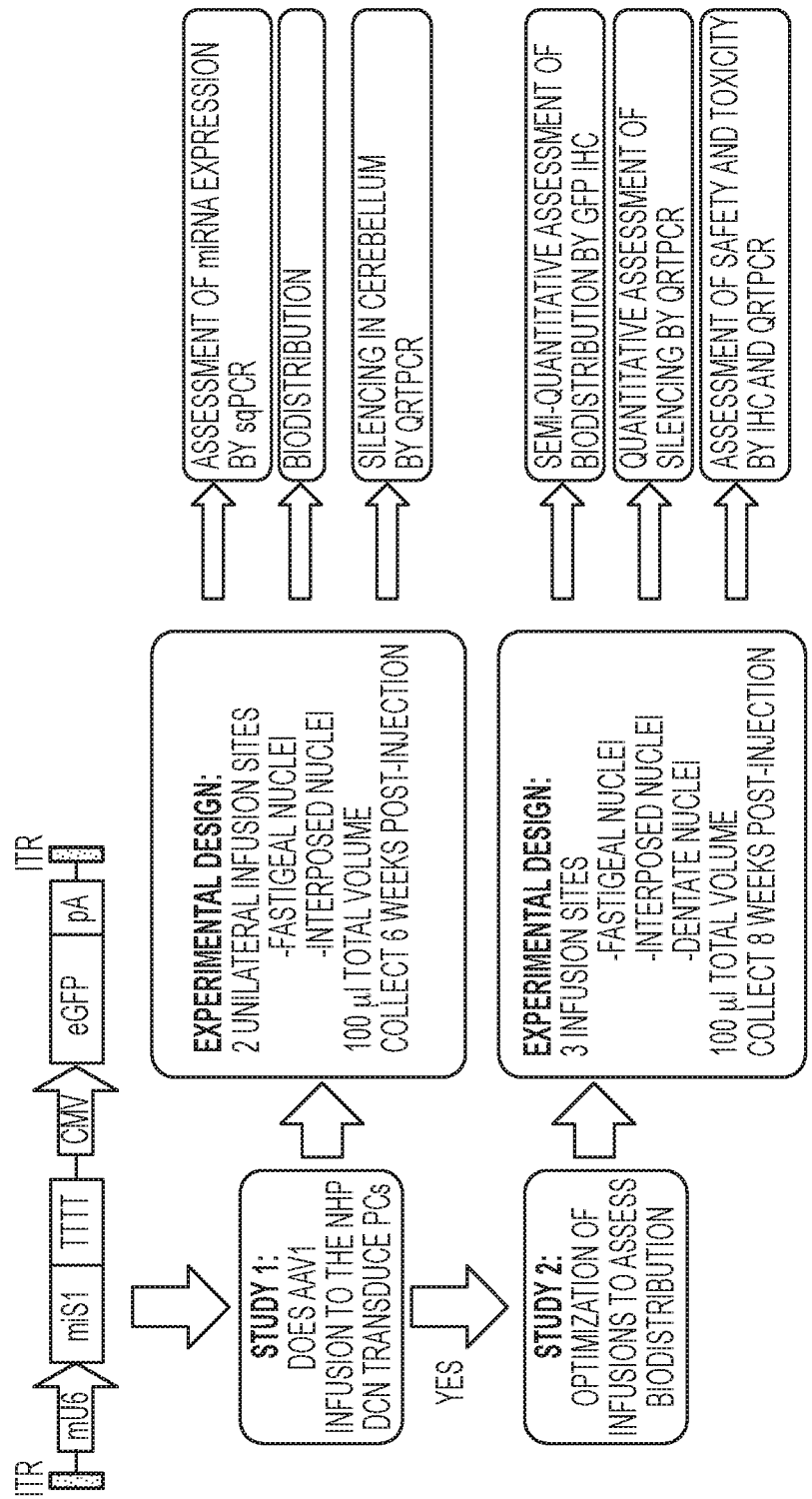
FIG. 1. AAVmiS1eGFP construct and an outline of experiments.

Spinocerebellar ataxia type 1 (SCA1), one of nine polyglutamine (polyQ) repeat diseases, is a dominantly inherited neurodegenerative disorder with no available treatment or cure. The incidence of SCA1 is approximately 1-2 per 100,000 people, indicating that there are 3000-6,000 patients in the US alone. SCA1 is caused by an unstable CAG expansion in the ATXN1 gene, which encodes ataxin-1. Normally, a range of CAG repeats interspersed with 1-3 CATs are found in ATXN1. In SCA1 patients, the ATXN1 CAG repeat is greater than 39, conferring a toxic gain-of-function to ataxin-1.

Although clinical onset of SCA1 may occur from childhood through adulthood, most patients present between 30-40 years of age with progressive wide-based gait, difficulties with balance, speech, swallowing, coordination and spasticity. Extracerebellar dysfunction may also appear with increased deep tendon reflexes and oculomotor abnormalities. Mild cognitive impairment occurs in 10-20% of patients. Neuropathological studies of tissues from SCA1 patients show that the primary sites of degeneration are the dentate nucleus, the inferior olive and cerebellar Purkinje cells (PCs). There is more degeneration in the upper vermis, less severe in the lateral cerebellar cortex, and mild changes in the flocculonodular lobes. There is also involvement of brainstem nuclei and spinocerebellar tracts and variable reports of cerebral involvement. Ataxin-1 is ubiquitously expressed and is prevalent in cerebellar PCs. Tissues from SCA patients also show ataxin-1 positive nuclear inclusions in Purkinje cells and brainstem neurons and in cerebrum.

Animal studies have been pivotal to better define the cellular and molecular mechanisms underlying SCA1 pathogenesis. There is extensive evidence supporting the notion that the disease-causing mutation acts through a toxic gain of function mechanism, and that suppressing its expression would not only arrest disease progression, but may reverse disease phenotypes. Using a doxycycline-inducible transgenic mouse model for SCA1, On and colleagues showed that repressing mutant protein expression 12 weeks after sustained expression significantly improved pathology and behavioral deficits (Zu, T., L. A. Duvick, M. D. Kaytor, M. S. Berlinger, H. Y. Zoghbi, H. B. Clark and H. T. On (2004). "Recovery from polyglutamine-induced neurodegeneration in conditional SCA1 transgenic mice." J Neurosci 24(40): 8853-8861). Thus, a window of opportunity for gene silencing strategies, initiated after disease onset, may exist.

Gene silencing approaches include RNA interference (RNAi) (Xia, H., Q. Mao, S. L. Eliason, S. Q. Harper, I. H. Martins, H. T. Orr, H. L. Paulson, L. Yang, R. M. Kotin and B. L. Davidson (2004). "RNAi suppresses polyglutamine-induced neurodegeneration in a model of spinocerebellar ataxia." Nat Med 10(8): 816-820; Xia, H., Q. Mao, H. L. Paulson and B. L. Davidson (2002). "siRNA-mediated gene silencing in vitro and in vivo." Nat Biotechnol 20(10): 1006-1010), antisense oligonucleotides (Kole, R., A. R. Krainer and S. Altman (2011). "RNA therapeutics: beyond RNA interference and antisense oligonucleotides." Nat Rev Drug Discov 11(2): 125-140), inhibitory antibodies, and more recently DNA editing approaches ((Wood, A. J., T. W. Lo, B. Zeitler, C. S. Pickle, E. J. Ralston, A. H. Lee, R. Amora, J. C. Miller, E. Leung, X. Meng, L. Zhang, E. J. Rebar, P. D. Gregory, F. D. Urnov and B. J. Meyer (2011). "Targeted genome editing across species using ZFNs and TALENs." Science 333(6040): 307; Basu, S., A. Aryan, J. M. Overcash, G. H. Samuel, M. A. Anderson, T. J. Dahlem, K. M. Myles and Z. N. Adelman (2015). "Silencing of end joining repair for efficient site-specific gene insertion after TALEN/CRISPR mutagenesis in *Aedes aegypti*." Proc Natl Acad Sci USA 112(13): 4038-4043; Ousterout, D. G., A. M. Kabadi, P. I. Thakore, W. H. Majoros, T. E. Reddy and C. A. Gersbach (2015). "Multiplex CRISPR/Cas9-based genome editing for correction of dystrophin mutations that cause Duchenne muscular dystrophy." Nat Commun 6: 6244).

In the present work we devised and tested a surgical approach aimed at providing adequate coverage of those brain regions affected in SCA1 patients. We show that directed delivery of rAAV1 to the deep cerebellar nuclei of the rhesus macaque brain results in broad transduction of Purkinje cells and brainstem neurons, achieving widespread gene silencing activity. These data also indicate the safety of ATXN1 silencing in primate brain.

The present invention provides method of inducing RNA interference by administering to a subject a nucleic acid, an expression cassette, a vector, or a composition described herein.

The present invention provides a vector containing a U6 promoter operably linked to a nucleic acid encoding an miRNA. The predicted transcription start sites of constructs of the present invention are different from those used by researchers in the past. In certain embodiments of the present invention, the U6miRNA has an extended 5' end. If the 5' end is truncated to resemble the previous CMV-based strategy, silencing efficacy is severely reduced. The present invention also provides improved flanking sequences that show improved efficacy over natural miR-30 flanking sequences. The use of the present miRNA strategy appears to alleviate toxicity associated with traditional shRNA approaches. The miRNA strategy does not generally generate excessive amounts of RNAi as do U6shRNA approaches.

As used herein the term "stem sequence" is a sequence that is complementary to another sequence in the same molecule, where the two complementary strands anneal to form a duplex (e.g., the first and second siRNA regions). The duplex that is formed maybe fully complementary, or may be less than fully complementary, such as 99%, 98%, 97%, 96%, 95,%, 94%, 93%, 92%, 91%, 90%, 89%, 88%, 87%, 86%, 85%, 84%, 83%, 82%, 81%, 80%, 75%, or 70% complementary to each other. Further, in certain embodiments, one strand may contain more nucleotides than the other strand, allowing the formation of a side loop.

In certain embodiments, the miRNA is an miSCA1, such as miSCA1 (SEQ ID NO:1 gugagcgaggacacaaggcugagcagcagcugugaagc-cacagaugggcugcugcucagccuuguguccugccuac).

In certain embodiments, a first siRNA region consists of 5'-CGGCGAACUGAAGUUUCCAGAA-3' (SEQ ID NO:2) and a second siRNA region consists of 5'-UUCUG-GAAACUUCAGUUCGCCA-3' (SEQ ID NO:3) (miSCA1-2225; SEQ ID NO: 4 ugagcgcggcgaacugaaguuuccagaacu-guaaagccacagaugggguucuggaaacuucaguucgccacgccu).

In certain embodiments, a first siRNA region consists of 5'-CGACCGUGUGAAUCAUU-GUUUACCGGCCAGCAGCAAGCAAUCAU-3' (SEQ ID NO:5) and a second siRNA region consists of 5'-GUGAUUGCUUGCUGCUGGCCGA-3' (SEQ ID NO:6) (miSCA1-1399, SEQ ID NO: 7: ugagcgccggccagcagcaagcaaucauccguaaagccacagauggg-gugauugcuugcugcuggccgacgccu).

In certain embodiments the sequence is 5'-UGAUUGC-UUGCUGCUGGCCGA-3' (SEQ ID NO:8).

In certain embodiments, the miRNA binds to a human target site sequence encoded by 5'-AAGCAACGACCT-GAAGATCGA-3' (SEQ ID NO:9).

In certain embodiments, the miRNA comprises the sequence 5'-TCGATCTTCAGGTCGTTGCTT-3' (SEQ ID NO:10).

In certain embodiments, the miRNA comprises the sequence 5'-UCGAUCUUCAGGUCGUUGCUU-3' (SEQ ID NO:11).

In certain embodiments, the miRNA comprises the sequence 5'-GUCGAUCUUCAGGUCGUUGCUU-3' (SEQ ID NO:12).

In certain embodiments, the RNAi molecule is one disclosed in U.S. Pat. Nos. 8,329,890; 8,779,116; 8,481,710; 8,524,879; 8,487,088; 8,258,286; 8,524,881; 8,299,215; 8,691,948; WO 2012/109667; and WO 2013/172964, which are incorporated by reference herein.

MicroRNA Shuttles for RNAi miRNAs are small cellular RNAs (~22nt) that are processed from precursor stem loop transcripts. Known miRNA stem loops can be modified to contain RNAi sequences specific for genes of interest. miRNA molecules can be preferable over shRNA molecules because miRNAs are endogenously expressed. Therefore, miRNA molecules are unlikely to induce dsRNA-responsive interferon pathways, they are processed more efficiently than shRNAs, and they have been shown to silence 80% more effectively.

Also, the promoter roles are different for miRNA molecules as compared to shRNA molecules. Tissue-specific, inducible expression of shRNAs involves truncation of polII promoters to the transcription start site. In contrast, miRNAs can be expressed from any polII promoter because the transcription start and stop sites can be relatively arbitrary.

Treatment of SCA1 (Ataxia-1)

The dominant polyglutamine expansion diseases, which include Spinocerebellar ataxia type 1 (SCA1) and Huntington's disease (HD), are progressive, untreatable neurodegenerative disorders. The present invention provides methods of using RNAi in vivo to treat SCA1 Disease. "Treating"

as used herein refers to ameliorating at least one symptom of, curing and/or preventing the development of a disease or a condition.

In certain embodiment of the invention, RNAi molecules are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when an RNAi molecule initiates the inhibition or degradation of the mRNA transcribed from a gene of interest in a sequence-specific manner via RNA interference, thereby preventing translation of the gene's product.

The reference to siRNAs herein is meant to include shRNAs and other small RNAs that can or are capable of modulating the expression of a targeted gene, e.g., the HD gene, for example via RNA interference. Such small RNAs include without limitation, shRNAs and microRNAs (miRNAs).

Disclosed herein is a strategy that results in substantial silencing of targeted genes via RNAi. Use of this strategy results in markedly diminished in vitro and in vivo expression of targeted genes. This strategy is useful in reducing expression of targeted genes in order to model biological processes or to provide therapy for human diseases. For example, this strategy can be applied to SCA1. As used herein the term "substantial silencing" means that the mRNA of the targeted gene is inhibited and/or degraded by the presence of the introduced siRNA, such that expression of the targeted gene is reduced by about 10% to 100% as compared to the level of expression seen when the siRNA is not present. Generally, when an gene is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the siRNA is not present. As used herein the term "substantially normal activity" means the level of expression of a gene when an siRNA has not been introduced to a cell.

SCA1 is a strong candidate for siRNA-based therapy. SCA1 is caused by CAG repeat expansions that encode polyQ in the disease protein. PolyQ expansion confers a dominant toxic property on the mutant protein that is associated with aberrant accumulation of the disease protein in neurons. SCA1 is progressive, ultimately fatal disorders that typically begin in adulthood. Expansion of the CAG repeat/polyQ domain confers upon the encoded protein a dominant toxic property. Thus, as a therapeutic strategy, efforts to lower expression of the mutant gene product prior to cell death could be highly beneficial to patients.

RNA Interference (RNAi) Molecules

An "RNA interference," "RNAi," "small interfering RNA" or "short interfering RNA" or "siRNA" or "short hairpin RNA" or "shRNA" molecule, or "miRNA" is a RNA duplex of nucleotides that is targeted to a nucleic acid sequence of interest. As used herein, the term "siRNA" is a generic term that encompasses the subset of shRNAs and miRNAs. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding ataxin-1. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24 or 25 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional siRNAs. "Artificial miRNA" or an "artificial miRNA shuttle vector," as used herein interchangably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (~35 nucleotides upstream and ~40 nucleotides downstream) arise from restriction enzyme sites within the multiple cloning site of the siRNA. As used herein the term "miRNA" encompasses both the naturally occurring miRNA sequences as well as artificially generated miRNA shuttle vectors.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

"Off-target toxicity" refers to deleterious, undesirable, or unintended phenotypic changes of a host cell that expresses or contains an siRNA. Off-target toxicity may result in loss of desirable function, gain of non-desirable function, or even death at the cellular or organismal level. Off-target toxicity may occur immediately upon expression of the siRNA or may occur gradually over time. Off-target toxicity may occur as a direct result of the expression siRNA or may occur as a result of induction of host immune response to the cell expressing the siRNA. Without wishing to be bound by theory, off-target toxicity is postulated to arise from high levels or overabundance of RNAi substrates within the cell. These overabundant or overexpressed RNAi substrates, including without limitation pre- or pri RNAi substrates as well as overabundant mature antisense-RNAs, may compete for endogenous RNAi machinery, thus disrupting natural miRNA biogenesis and function. Off-target toxicity may also arise from an increased likelihood of silencing of unintended mRNAs (i.e., off-target) due to partial complementarity of the sequence. Off target toxicity may also occur from improper strand biasing of a non-guide region such that there is preferential loading of the non-guide region over the targeted or guide region of the RNAi. Off-target toxicity may also arise from stimulation of cellular responses to dsRNAs which include dsRNA (IFN-b, PKR, OAS1). "Decreased off target toxicity" refers to a decrease, reduction, abrogation or attenuation in off target toxicity such that the therapeutic effect is more beneficial to the host than the toxicity is limiting or detrimental as measured by an improved duration or quality of life or an improved sign or symptom of a disease or condition being targeted by the siRNA. "Limited off target toxicity" or "low off target toxicity" is used to refer to unintended undesirable phenotypic changes to a cell or organism, whether detectable or not, that does not preclude or outweigh or limit the therapeutic benefit to the host treated with the siRNA and may be considered a "side effect" of the therapy. Decreased or limited off target toxicity may be determined or inferred by comparing the in vitro analysis such as Northern blot or QPCR for the levels of siRNA substrates or the in vivo effects comparing an equivalent shRNA vector to the miRNA shuttle vector of the present invention.

"Knock-down," "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where siRNA molecules have not been administered). Knock-down of gene expression can be directed by the use of dsRNAs or siRNAs.

"RNA interference (RNAi)" is the process of sequence-specific, post-transcriptional gene silencing initiated by siRNA. During RNAi, siRNA induces degradation of target mRNA with consequent sequence-specific inhibition of gene expression.

According to a method of the present invention, the expression of mRNA encoding SCA1 can be modified via RNAi. For example, the accumulation of mRNA encoding SCA1 can be suppressed in a cell. The term "suppressing" refers to the diminution, reduction or elimination in the number or amount of mRNA molecules present in a particular cell. For example, the accumulation of mRNA can be suppressed in a cell by RNA interference (RNAi), e.g., the gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single-stranded or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid nucleic acid molecules and compositions containing those molecules. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

A "transgene" refers to a gene that has been introduced into the genome by transformation. Transgenes include, for example, DNA that is either heterologous or homologous to the DNA of a particular cell to be transformed. Additionally, transgenes may include native genes inserted into a non-native organism, or chimeric genes.

The term "endogenous gene" refers to a native gene in its natural location in the genome of an organism.

The terms "protein," "peptide" and "polypeptide" are used interchangeably herein.

"Wild-type" refers to the normal gene or organism found in nature.

"Genome" refers to the complete genetic material of an organism.

A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an siRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence," i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The term "open reading frame" (ORF) refers to the sequence between translation initiation and termination codons of a coding sequence. The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell.

"cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted herein, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA—box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated," they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences) can be used. The BLASTN program (for nucleotide sequences) uses as defaults a wordlength (W) of 11, an expectation (E) of 10, a cutoff of 100, M=5, N=−4, and a comparison of both strands. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide matches and an identical percent sequence identity when compared to the corresponding alignment generated by the preferred program.

(c) As used herein, "sequence identity" or "identity" in the context of two nucleic acid sequences makes reference to a specified percentage of nucleotides in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted herein, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The Tm is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the Tm can be approximated from the equation: Tm 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point (Tm) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell 2001, for a description of SSC buffer). Often, a high stringency wash is preceded by a low stringency wash to remove background probe signal. For short nucleic acid sequences (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the Tm for a particular nucleic acid molecule.

Very stringent conditions are selected to be equal to the Tm for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., E. coli) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

The siRNAs of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. The RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double stranded interfering RNA molecules, which are also useful to inhibit expression of a target gene.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from a source by chemical means, e.g., by the use of restriction endonucleases, so that it can be further manipulated, e.g., amplified, for use in the invention, by the methodology of genetic engineering. "Recombinant DNA" includes completely synthetic DNA sequences, semi synthetic DNA sequences, DNA sequences isolated from biological sources, and DNA sequences derived from RNA, as well as mixtures thereof.

Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly Photinus pyralis. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As discussed herein, a "transfected" "or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell," comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into an anti-sense RNA, a siRNA, as well as a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining an regulatable promoter with an endogenous coding sequence via homologous recombination.

The condition amenable to gene inhibition therapy may be a prophylactic process, i.e., a process for preventing disease or an undesired medical condition. Thus, the instant invention embraces a system for delivering siRNA that has a prophylactic function (i.e., a prophylactic agent) to the mammalian recipient.

Adeno Associated Virus (AAV)

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q arm of chromosome 19. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

To date, numerous serologically distinct AAVs have been identified, and more than a dozen have been isolated from humans or primates. The genome of AAV2 is 4680 nucleotides in length and contains two open reading frames (ORFs). The left ORF encodes the non-structural Rep proteins, Rep 40, Rep 52, Rep 68 and Rep 78, which are involved in regulation of replication and transcription in addition to the production of single-stranded progeny genomes. Furthermore, two of the Rep proteins have been associated with the preferential integration of AAV genomes into a region of the q arm of human chromosome 19. Rep68/78 has also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats (ITR) which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The AAV virion is a non-enveloped, icosohedral particle approximately 25 nm in diameter, consisting of three related proteins referred to as VP1, VP2 and VP3. The right ORF encodes the capsid proteins VP1, VP2, and VP3. These proteins are found in a ratio of 1:1:10 respectively and are all derived from the right-hand ORF. The capsid proteins differ from each other by the use of alternative splicing and an unusual start codon. Deletion analysis has shown that removal or alteration of VP1 which is translated from an alternatively spliced message results in a reduced yield of infections particles. Mutations within the VP3 coding region result in the failure to produce any single-stranded progeny DNA or infectious particles. An AAV particle is a viral particle comprising an AAV capsid protein. An AAV capsid polypeptide can encode the entire VP1, VP2 and VP3 polypeptide. The particle can be a particle comprising AAV2 and other AAV capsid proteins (i.e., a chimeric protein, such as AAV1 and AAV2). Variations in the amino acid sequence of the AAV2 capsid protein are contemplated herein, as long as the resulting viral particle comprises the AAV2 capsid remains antigenically or immunologically distinct from AAV1, as can be routinely determined by standard methods. Specifically, for example, ELISA and Western blots can be used to determine whether a viral particle is antigenically or immunologically distinct from AAV1. Furthermore, the AAV2 viral particle preferably retains tissue tropism distinct from AAV1.

An AAV2 particle is a viral particle comprising an AAV2 capsid protein. An AAV2 capsid polypeptide encoding the entire VP1, VP2, and VP3 polypeptide can overall have at least about 63% homology (or identity) to the polypeptide having the amino acid sequence encoded by nucleotides set forth in NC_001401 (nucleotide sequence encoding AAV2 capsid protein). The capsid protein can have about 70% homology, about 75% homology, 80% homology, 85% homology, 90% homology, 95% homology, 98% homology, 99% homology, or even 100% homology to the protein encoded by the nucleotide sequence set forth in NC_001401. The capsid protein can have about 70% identity, about 75% identity, 80% identity, 85% identity, 90% identity, 95% identity, 98% identity, 99% identity, or even 100% identity to the protein encoded by the nucleotide sequence set forth in NC_001401. The particle can be a particle comprising another AAV and AAV2 capsid protein, i.e., a chimeric protein. Variations in the amino acid sequence of the AAV2 capsid protein are contemplated herein, as long as the resulting viral particle comprising the AAV2 capsid remains antigenically or immunologically distinct from AAV4, as can be routinely determined by standard methods. Specifically, for example, ELISA and Western blots can be used to determine whether a viral particle is antigenically or immunologically distinct from AAV1. Furthermore, the AAV2 viral particle preferably retains tissue tropism distinction from AAV1, such as that exemplified in the examples herein, though an AAV2 chimeric particle comprising at least one AAV2 coat protein may have a different tissue tropism from that of an AAV2 particle consisting only of AAV2 coat proteins.

In certain embodiments, the invention further provides an AAV2 particle containing, i.e., encapsidating, a vector comprising a pair of AAV2 inverted terminal repeats. The nucleotide sequence of AAV2 ITRs is known in the art. Furthermore, the particle can be a particle comprising both AAV1 and AAV2 capsid protein, i.e., a chimeric protein. Moreover, the particle can be a particle encapsidating a vector comprising a pair of AAV inverted terminal repeats from other AAVs (e.g., AAV1-AAV9 and AAVrh10). The vector encapsidated in the particle can further comprise an exogenous nucleic acid inserted between the inverted terminal repeats.

The following features of AAV have made it an attractive vector for gene transfer. AAV vectors have been shown in vitro to stably integrate into the cellular genome; possess a broad host range; transduce both dividing and non-dividing cells in vitro and in vivo and maintain high levels of expression of the transduced genes. Viral particles are heat stable, resistant to solvents, detergents, changes in pH, temperature, and can be concentrated on CsCl gradients or by other means. The present invention provides methods of administering AAV particles, recombinant AAV vectors, and recombinant AAV virions. For example, an AAV2 particle is a viral particle comprising an AAV2 capsid protein, or an AAV1 particle is a viral particle comprising an AAV1 capsid protein. A recombinant AAV2 vector is a nucleic acid construct that comprises at least one unique nucleic acid of AAV2. A recombinant AAV2 virion is a particle containing a recombinant AAV2 vector. To be considered within the term "AAV2 ITRs" the nucleotide sequence must retain one or both features described herein that distinguish the AAV2 ITR from the AAV1 ITR: (1) three (rather than four as in AAV1) "GAGC" repeats and (2) in the AAV2 ITR Rep binding site the fourth nucleotide in the first two "GAGC" repeats is a C rather than a T.

The promoter to drive expression of the protein or the sequence encoding another agent to be delivered can be any desired promoter, selected by known considerations, such as the level of expression of a nucleic acid functionally linked to the promoter and the cell type in which the vector is to be used. Promoters can be an exogenous or an endogenous promoter. Promoters can include, for example, known strong promoters such as SV40 or the inducible metallothionein promoter, or an AAV promoter, such as an AAV p5 promoter. Additional examples of promoters include promoters derived from actin genes, immunoglobulin genes, cytomegalovirus (CMV), adenovirus, bovine papilloma virus, adenoviral promoters, such as the adenoviral major late promoter, an inducible heat shock promoter, respiratory syncytial virus, Rous sarcomas virus (RSV), etc. Additional examples include regulated promoters.

The AAV vector can further comprise an exogenous (heterologous) nucleic acid functionally linked to the promoter. By "heterologous nucleic acid" is meant that any heterologous or exogenous nucleic acid can be inserted into the vector for transfer into a cell, tissue or organism. The nucleic acid can encode a polypeptide or protein or an antisense RNA, for example. By "functionally linked" is meant such that the promoter can promote expression of the heterologous nucleic acid, as is known in the art, such as appropriate orientation of the promoter relative to the heterologous nucleic acid. Furthermore, the heterologous nucleic acid preferably has all appropriate sequences for expression of the nucleic acid, as known in the art, to functionally encode, i.e., allow the nucleic acid to be expressed. The nucleic acid can include, for example, expression control sequences, such as an enhancer, and necessary information processing sites, such as ribosome binding sites, RNA splice sites, polyadenylation sites, and transcriptional terminator sequences. The nucleic acid can encode more than one gene product, limited only by the size of nucleic acid that can be packaged.

In certain embodiments of the present invention, the heterologous nucleic acid can encode beneficial proteins that replace missing or defective proteins required by the subject into which the vector in transferred, such as Rheb or Rhes.

An AAV1 particle is a viral particle comprising an AAV1 capsid protein. Variations in the amino acid sequence of the AAV1 capsid protein are contemplated herein, as long as the resulting viral particle comprising the AAV1 capsid remains antigenically or immunologically distinct from other AAV capsids, as can be routinely determined by standard methods. Specifically, for example, ELISA and Western blots can be used to determine whether a viral particle is antigenically or immunologically distinct from other AAV serotypes.

The term "polypeptide" as used herein refers to a polymer of amino acids and includes full-length proteins and fragments thereof. Thus, "protein" and "polypeptide" are often used interchangeably herein. Substitutions can be selected by known parameters to be neutral. As will be appreciated by those skilled in the art, the invention also includes those polypeptides having slight variations in amino acid sequences or other properties. Such variations may arise naturally as allelic variations (e.g. due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. These modifications can result in changes in the amino acid sequence, provide silent mutations, modify a restriction site, or provide other specific mutations.

The present method provides a method of delivering a nucleic acid to a cell comprising administering to the cell an AAV particle containing a vector comprising the nucleic acid inserted between a pair of AAV inverted terminal repeats, thereby delivering the nucleic acid to the cell. Administration to the cell can be accomplished by any means, including simply contacting the particle, optionally contained in a desired liquid such as tissue culture medium, or a buffered saline solution, with the cells. The particle can be allowed to remain in contact with the cells for any desired length of time, and typically the particle is administered and allowed to remain indefinitely. For such in vitro methods, the virus can be administered to the cell by standard viral transduction methods, as known in the art and as exemplified herein. Titers of virus to administer can vary, particularly depending upon the cell type, but will be typical of that used for AAV transduction in general. Additionally the titers used to transduce the particular cells in the present examples can be utilized. The cells can include any desired cell in humans as well as other large (non-rodent) mammals, such as primates, horse, sheep, goat, pig, and dog.

More specifically, the present invention provides a method of delivering a nucleic acid to a cell in the brain, particularly medium spiny neurons, comprising the nucleic acid inserted between a pair of AAV inverted terminal repeats, thereby delivering the nucleic acid to the cell.

The present invention further provides a method of delivering a nucleic acid to a cell in a subject comprising administering to the subject an AAV particle comprising the nucleic acid inserted between a pair of AAV inverted terminal repeats, thereby delivering the nucleic acid to a cell in the subject.

Also provided is a method of delivering a nucleic acid to a brain cell, such as a neuron in the striatum or cortex in a subject comprising administering to the subject an AAV particle comprising the nucleic acid inserted between a pair of AAV inverted terminal repeats, thereby delivering the nucleic acid to the neuron or other cell in the subject.

Certain embodiments of the present disclosure provide a cell comprising a viral vector as described herein.

AAV Vectors

In one embodiment, a viral vector of the disclosure is an AAV vector. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight known serotypes of primate AAVs, AAV-1 to AAV-9 and AAVrh10. For example, serotype AAV2 is used to refer to an AAV which contains capsid proteins encoded from the cap gene of AAV2 and a genome containing 5' and 3' ITR sequences from the same AAV2 serotype. As used herein, for example, rAAV1 may be used to refer an AAV having both capsid proteins and 5'-3' ITRs from the same serotype or it may refer to an AAV having capsid proteins from one serotype and 5'-3' ITRs from a different AAV serotype, e.g., capsid from AAV serotype 2 and ITRs from AAV serotype 5. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

An "AAV virus" or "AAV viral particle" refers to a viral particle composed of at least one AAV capsid protein (preferably by all of the capsid proteins of a wild-type AAV) and an encapsidated polynucleotide. If the particle comprises heterologous polynucleotide (i.e., a polynucleotide other than a wild-type AAV genome such as a transgene to be delivered to a mammalian cell), it is typically referred to as "rAAV".

In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

In one embodiment, AAV ITRs can be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In one embodiment, AAV capsids can be derived from AAV2. Suitable DNA molecules for use in AAV vectors will be less than about 5 kilobases (kb), less than about 4.5 kb, less than about 4 kb, less than about 3.5 kb, less than about 3 kb, less than about 2.5 kb in size and are known in the art.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from non-viral genes, such as the murine metallothionein gene, will also find use herein. Such promoter sequences are commercially available from, e.g., Stratagene (San Diego, Calif.).

In one embodiment, both heterologous promoters and other control elements, such as CNS-specific and inducible promoters, enhancers and the like, will be of particular use. Examples of heterologous promoters include the CMV promoter. Examples of CNS-specific promoters include those isolated from the genes from myelin basic protein (MBP), glial fibrillary acid protein (GFAP), and neuron specific enolase (NSE). Examples of inducible promoters include DNA responsive elements for ecdysone, tetracycline, hypoxia and aufin.

In one embodiment, the AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art.

Alternatively, AAV ITRs can be excised from the viral genome or from an AAV vector containing the same and fused 5' and 3' of a selected nucleic acid construct that is present in another vector using standard ligation techniques. For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs.

Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods.

In order to produce rAAV virions, an AAV expression vector is introduced into a suitable host cell using known techniques, such as by transfection. A number of transfection techniques are generally known in the art. See, e.g., Sambrook et al. (1989) Molecular Cloning, a laboratory manual, Cold Spring Harbor Laboratories, New York. Particularly suitable transfection methods include calcium phosphate co-precipitation, direct microinjection into cultured cells, electroporation, liposome mediated gene transfer, lipid-mediated transduction, and nucleic acid delivery using high-velocity microprojectiles.

In one embodiment, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used in the practice of the present disclosure. Particularly, the human cell line 293 is a human embryonic kidney cell line that has been transformed with adenovirus type-5 DNA fragments, and expresses the adenoviral E1a and E1b genes. The 293 cell line is readily transfected, and provides a particularly convenient platform in which to produce rAAV virions.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Suitable homologues of the AAV rep coding region include the human herpesvirus 6 (HHV-6) rep gene which is also known to mediate AAV-2 DNA replication.

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome.

In one embodiment, AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors have been described which encode Rep and/or Cap expression products.

Methods of delivery of viral vectors include injecting the AAV into the subject. Generally, rAAV virions may be introduced into cells of the CNS using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, pharmaceutical compositions will comprise sufficient genetic material to produce a therapeutically effective amount of the nucleic acid of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991).

It should be understood that more than one transgene could be expressed by the delivered viral vector. Alternatively, separate vectors, each expressing one or more different transgenes, can also be delivered to the subject as described herein. Furthermore, it is also intended that the viral vectors delivered by the methods of the present disclosure be combined with other suitable compositions and therapies.

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

In certain embodiments, the rAAV is administered at a dose of about 0.3-2 ml of $1\times10^5$-$1\times10^{16}$ vg/ml. In certain embodiments, the rAAV is administered at a dose of about 1-3 ml of $1\times10^7$-$1\times10^{14}$ vg/ml. In certain embodiments, the rAAV is administered at a dose of about 1-2 ml of $1\times10^8$-$1\times10^{13}$ vg/ml.

Formulations containing the rAAV particles will contain an effective amount of the rAAV particles in a vehicle, the effective amount being readily determined by one skilled in the art. The rAAV particles may typically range from about 1% to about 95% (w/w) of the composition, or even higher or lower if appropriate. The quantity to be administered depends upon factors such as the age, weight and physical condition of the animal or the human subject considered for treatment. Effective dosages can be established by one of ordinary skill in the art through routine trials establishing dose response curves. The subject is treated by administration of the rAAV particles in one or more doses. Multiple doses may be administered as is required to maintain adequate enzyme activity.

Vehicles, including water, aqueous saline, artificial CSF, or other known substances can be employed with the subject invention. To prepare a formulation, the purified composition can be isolated, lyophilized and stabilized. The composition may then be adjusted to an appropriate concentration, optionally combined with an anti-inflammatory agent, and packaged for use.

The present invention provides a method of increasing the level of a target protein in a cell by introducing a protein, or nucleic acid molecule encoding a protein described above into a cell in an amount sufficient to increase the level of the target protein in the cell. In certain embodiments, the accumulation of target protein is increased by at least 10%. The accumulation of target protein is increased by at least 10%, 20%, 30%, 40%, 50%, 60%, 70%, 80%, 90% 95%, or 99%.

Furthermore, the AAV vector may be selected/designed according to the desired route of administration, for example, and without limitation, for systemic administration, an AAV vector capable of crossing the blood-brain barrier may be used (e.g., AAV9, or a chimeric AAV vector having AAV9 capsid proteins). The present invention also provides a method of administering AAV to the bloodstream since some serotypes are capable of traversing the blood-brain barrier.

Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art. As used herein, the term "therapeutic siRNA" refers to any siRNA that has a beneficial effect on the recipient. Thus, "therapeutic siRNA" embraces both therapeutic and prophylactic siRNA.

Administration of siRNA may be accomplished through the administration of the nucleic acid molecule encoding the siRNA. Pharmaceutical formulations, dosages and routes of administration for nucleic acids are generally known.

The present invention envisions treating mRNA encoding SCAT in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the brain. Alternatively the therapeutic agent may be introduced intrathecally for brain and spinal cord conditions. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0 saline solutions and water.

The invention will now be illustrated by the following non-limiting Example.

EXAMPLE 1

Translating RNAi Therapy for Spinocerebellar Ataxia Type 1

Materials and Methods

Animals and Treatment Groups

Nine adult male and 3 adult female rhesus monkeys (*Macaca mulatta*) were obtained from Abbott, Harlan, Oregon National Primate Research Center, and Tulane National Primate Research Center. Animals were pair-housed on a 12-h light/12-h dark cycle. Nine adult male monkeys 9.9±0.8 years of age and weighed 15.7±0.7 kg. 3 adult female monkeys 7.3±0.9 years old and weighed 8.3±1.0 kg. All procedures were approved by the University of Illinois Chicago Institutional Animal Care and Use Committee and the Rush University Institutional Animal Care and Use Committee and accredited by the Association for Assessment and Accreditation of Laboratory Animal Care. Animal care was supervised by veterinarians skilled in the care and maintenance of non-human primates.

Stereotaxic Surgery

All surgical procedures were conducted under isoflurane anesthesia (1-3% maintenance, inhalation) and sterile field conditions. Using MRI-guided techniques combined with a Stealth Navigation system (generously donated by Medtronics Inc.), a 100 µl Hamilton syringe fitted with a 30 G needle loaded with AAVmiS1eGFP or vehicle was lowered through small burr holes to the individual target deep cerebellar nuclei described in Table 1. Injection volumes shown in Table 1 were infused at 0.5-1.0 µl/min to minimize injectate reflux, inflammation or damage to the parenchyma. After the injection, the needle was left in place 2 min then slowly retracted. The following pre and postoperative analgesics were given: meloxicam (0.1 mg/kg subcutaneously SID×3 days), hydromorphone (0.1 mg/kg intramuscular once pre-operatively), and sustained release buprenorphine (0.2 mg/kg subcutaneously once post-operatively). Animals received cefazolin (25 mg/kg IV once pre-operatively) and post-operatively (25 mg/kg intramuscular BID for 3 days).

TABLE 1

Optimization of surgical sites and doses in NHPs

| Study | Surgical Target | Viral Genomes | Volume | Total VG | Total Vol |
|---|---|---|---|---|---|
| 1 | Fastigial | 1.25E11 | 50 µl | 8E10 or | 100 µl |
|   |           | 4.00E10 | 50 µl | 2.5E11  |        |
|   | Interposed | 1.25E11 | 50 µl |        |        |
|   |           | 4.00E10 | 50 µl |        |        |
| 2 | Fastigial | 5.20E11 | 20 µl | 2.6E12 | 100 µl |
|   | Interposed | 7.90E11 | 30 µl |        |        |
|   | Dentate   | 1.30E12 | 50 µl |        |        |

General Health Assessment

Baseline body weights were obtained before surgery. Post-operatively, animals were monitored for activity, appetite, urine/fecal output, incision healing and general appearance daily ≥6 days by the University of Illinois Chicago veterinary staff for adverse reactions. None of the animals were reported to have any neurologic deficits from the surgeries. All of the animals were reported being bright/alert/responsive within two days of surgery.

Necropsy and Brain Tissue Processing

Six or eight weeks post-surgery, animals were deeply sedated and euthanized by transcardial saline perfusion. The brain was removed from the calvarium and placed in a chilled coronal or sagittal block and 4 mm slabs were made. On ice, bilateral tissue punches from the cerebellar cortex, DCN, inferior olive, and thalamus were collected for molecular analyses and immediately frozen to preserve DNA, RNA and protein. Remaining tissue was post-fixed in 4% paraformaldehyde solution for 48 hours then transferred to a 30% sucrose solution. Forty µm coronal slices were sectioned on a microtome, and stored in cryoprotectant solution at −20° C. until processed.

Semi-Quantification of miRNA and Ataxin-1 Messenger RNA Expression

Total RNA was extracted from tissue punches using Trizol® (Life Technologies). RNA was isolated from left and right cerebellar lobules, dentate nuclei, inferior olivary complexes from the medulla oblongata, and ventral lateral thalamic nuclei from each animal from both studies. Punches from uninjected hemispheres served as endogenous controls. microRNA (miRNA)-specific complementary DNA was generated using miRNA stem-loop-specific primers and the High Capacity cDNA Reverse Transcription Kit (Life Technologies). Semi-quantitative PCR detected expression of Si as previously described (Keiser, M. S., J. C. Geoghegan, R. L. Boudreau, K. A. Lennox and B. L. Davidson (2013). "RNAi or overexpression: alternative therapies for Spinocerebellar Ataxia Type 1." Neurobiol Dis 56: 6-13) using the Biolase PCR Kit (Bioline). In addition, complementary DNA libraries were also generated. Endogenous mRNA levels of ataxin-1 and rhesus GFAP were quantified by TaqMan® primer/probe sets (Applied Biosystems). Endogenous rhesus GAPDH was used to normalize expression across samples.

Histopathological Examination

Forty µm thick, free floating brain sections were processed by immunohistochemical visualization of eGFP expression (Living Colors®A.V. Monoclonal Antibody (JL-8), 1:2000; Clontech) and for activated microglia (Iba1, 1:1000; Wako) as previously described (McBride et al. 2011). Sagittal cerebellar sections (2-3 from each animal) were immunostained for eGFP and inspected using a Leica DM600B microscope. eGFP positive PCs were visually scored as a percentage of the total number of Purkinje cells in lobules II-X.

Statistical Analysis

Statistical analyses were conducted using GraphPad Prism 6.0 software. For all analyses, p-values less than 0.05 were considered statistically significant. Quantitative analyses between left and right hemispheres for each animal were performed using paired, two-tailed, t-tests.

Results

Verification of Inhibitory RNA Expression and Ataxin-1 Suppression in NHP

Figures 2A, 2B, 2C, 2D:
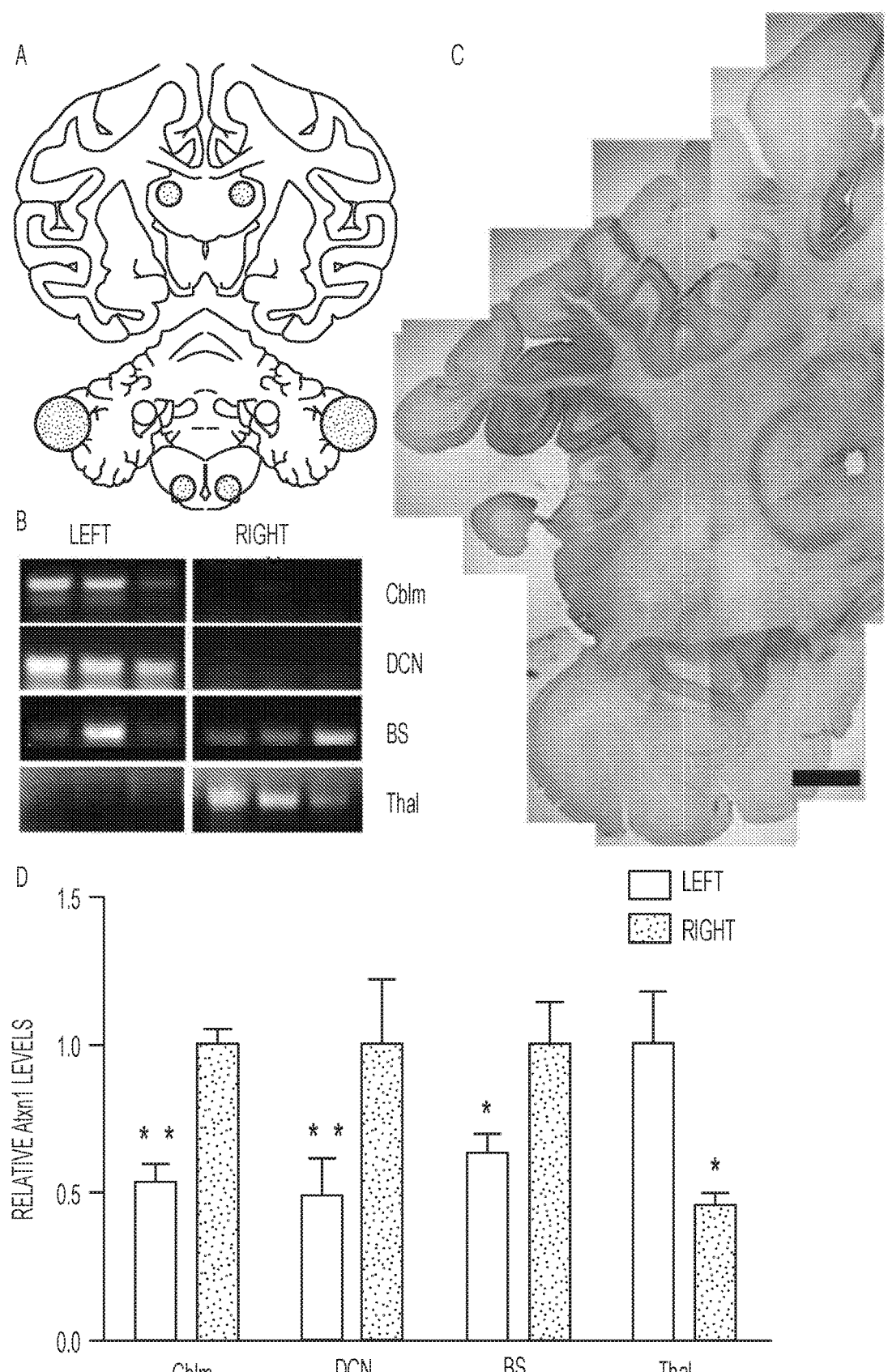
FIGS. 2A-2D. A preliminary study demonstrating transduction of PCs and silencing of ATX7N1. (A) Cartoon showing where tissue punches were taken from the ventral lateral thalamic nuclei (upper) and the DCN, cerebellar cortex, and inferior olivary complex (bottom). (B) Semi-quantitative PCR from three representative animals from the left and right cerebellum (Cblm), dentate nucleus (DCN), inferior olive from the brainstem (BS), and thalamus (Thal). (C) Stitched sagittal photomicrograph of the injected (left) hemisphere immunostained for eGFP (dark brown) Scale bar=1 mm. (D) Expression of ATX1N1 messenger RNA levels from left (white bars) and right (black bars) tissue punches (n=6 per hemisphere/per location) from the cerebellar cortex (Cblm), dentate nucleus (DCN), inferior olive (BS) and thalamus (Thal) as a percentage of the average amount detected in the right hemisphere (Cblm, DCN, BS) or left hemisphere (Thal). *P<0.05; **P<0.01.
Figure 7:
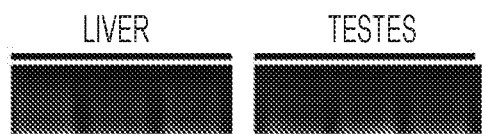
FIG. 7. sqPCR for miS1 expression in the liver and testes of NHP.

The study design is outlined in FIG. 1. First, we tested if rAAV1.miS1 delivered to the DCN of NHPs would transduce Purkinje cells as well as DCN neurons, and that expression of miS1 would reduce endogenous NHP ataxin-1. Tissue punches taken from the site of injection (medial DCN), the cerebellar cortex, inferior olive (medulla), and the ventral lateral thalamic nuclei from both hemispheres for protein and RNA evaluation (FIG. 2A) and subjected to semi-quantitative PCR (sqPCR) confirmed miS1 expression in the left DCN and cerebellar cortex (FIG. 2B). miS1 was expressed in the left and right inferior olivary complexes due to contralateral and ipsilateral projections to the DCN. We also detected miS1 in the contralateral ventral lateral thalamic nuclei in axonal projections from the DCN. The remaining brain tissue was blocked in the coronal plane in 4 mm-thick sections and post-fixed for histological analysis. Immunohistochemical analyses for eGFP of coronal brain sections demonstrated that AAVmiS1 eGFP transduced neuronal cell bodies in the entire left DCN (fastigial, interposed and dentate) and 10-30% of the left cerebellar cortex (FIG. 2C). QRTPCR data showed a significant reduction in rhesus ataxin-1 mRNA levels in the cerebellar cortex, DCN, brainstem and contralateral thalamus (FIG. 2D). Biodistribution studies to assess if rAAV was present in peripheral tissues indicated that vector was not shed systemically. Vector genomes were undetectable in liver and testes as analyzed by sqPCR (FIG. 7). These experiments demonstrate that delivery of rAAV to the DCN can transduce the cerebellar cortex and brainstem nuclei.

Improving Biodistribution with Delivery to the Dentate Nucleus.

Figures 3A, 3B, 3C, 3D:
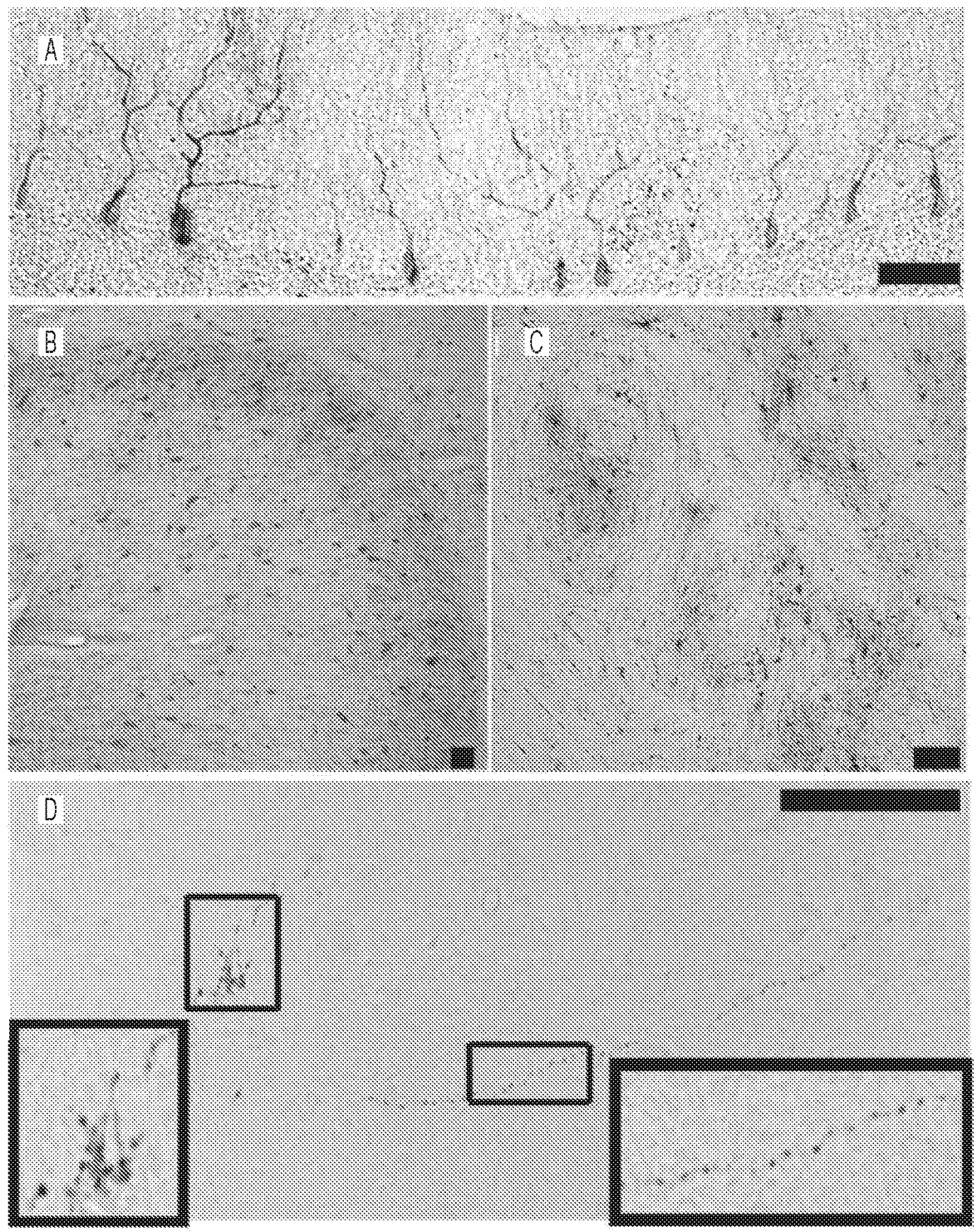
FIGS. 3A-3D. Immunohistochemistry for eGFP protein. (A) Sagittal section of the left hemisphere of an injected cerebellum. eGFP positive immunostaining in Purkinje cell somas and their dendritic arbors. (B) Coronal section of an injected cerebellum showing eGFP positive neurons in the dentate nucleus. (C) eGFP positive neurons within the left inferior olivary complex. (D) eGFP positive axonal projections from the contralateral DCN synapsing onto the ventral lateral nuclei of the right thalamus. Left inset shows eGFP-positive pre-synaptic termini. Right inset shows eGFP-positive magnified axon. Scale Bar=100 µm.

Because the dentate is among the earliest and most affected structures affected in SCA1, we next tested if an additional injection into the dentate was tolerated, and how the approach would impact transduction biodistribution. All animals (N=6) received the same volume and titer of AAVmiS1eGFP as the first cohort, but with a different infusion paradigm (Table 1). As before, animals did not show any overt behavioral abnormalities and were euthanized 8 weeks after injection. The cerebellum was blocked in the sagittal plane in 4 mm thick slabs. Alternating slabs were withheld for RNA extraction or post-fixed intact for immunohistological analysis. GFP-positive Purkinje cells were found in most lobules of the cerebellar cortex (FIG. 3A), and in DCN and inferior olivary complex neurons (FIG. 3B, C). GFP-positive axonal projections and pre-synaptic termini of DCN neurons were also detected in the contralateral thalamus, indicating anterograde (fibers) transport of AAV1 and/or GFP (FIG. 3D).

Figures 4A, 4B, 4C, 4D, 4E, 4F:
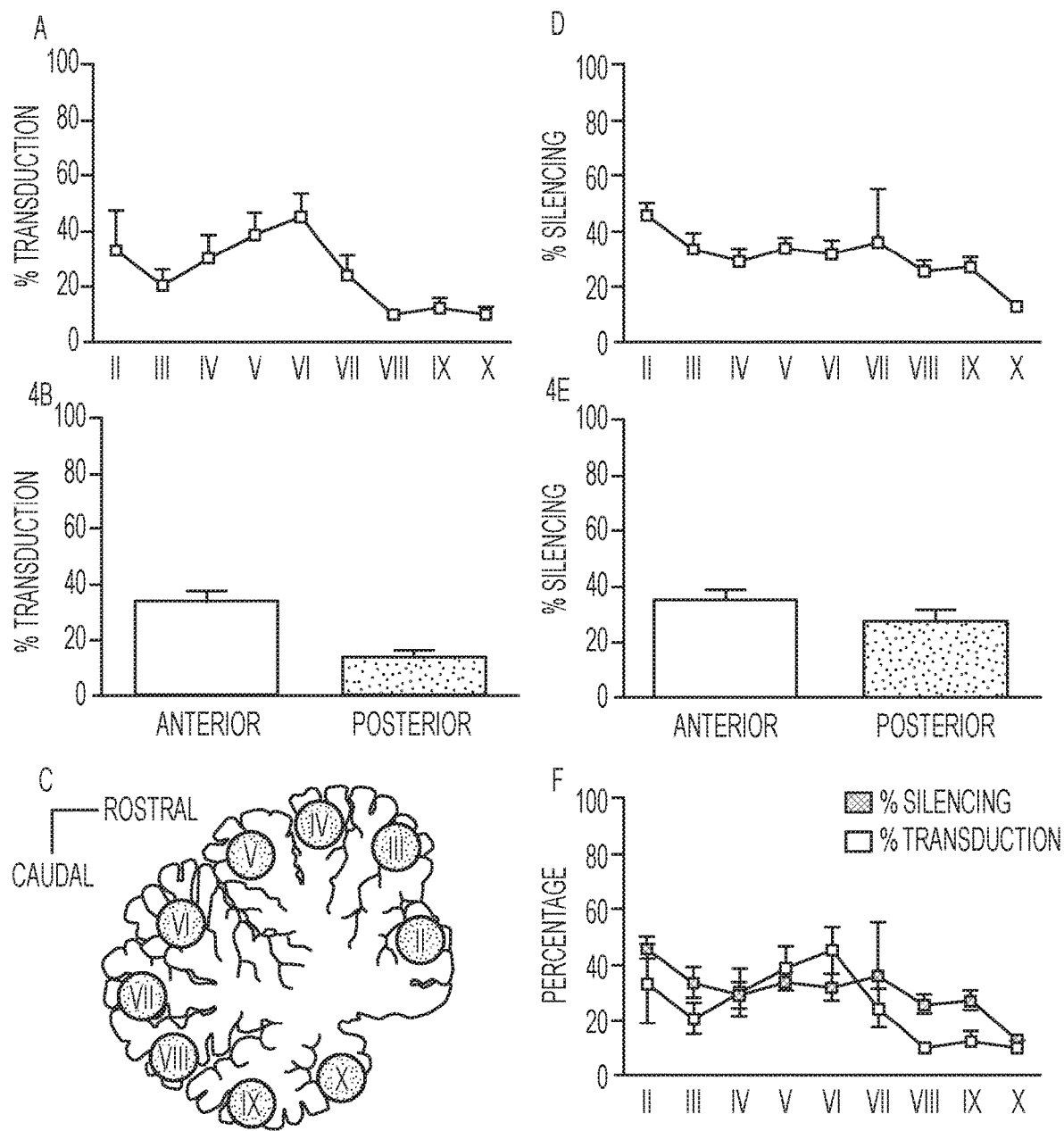
FIGS. 4A-4F. Transduction and knockdown of ATXN1 across cerebellar lobules. (A) Purkinje cells positively expressing eGFP by immunohistochemistry was qualitatively estimated as a percentage of the individual lobule (II-X) from 1-2 equivalent sagittal sections for all 6 animals. (B) Percentage of eGFP-positive Purkinje cells per lobule represented as anterior and posterior lobes of the cerebellum. Lobules II-V averaged for the anterior lobe (black bar); lobules VI-X were averaged for the posterior lobe (grey bar). (C) Cartoon representation of tissue punches taken from the sagittal slab blocked 4-8 mm from median. (D) Percentage of silencing of ATXN1 messenger RNA levels in tissue punches from each lobule from the left (injected) cerebellar hemisphere relative to the uninjected (right) hemisphere. (E) Percent of ATXN1 silencing in the anterior lobe of the cerebellum. Lobules II-V averaged for the anterior lobe (black bar); lobules VI-X averaged for the posterior lobe (grey bar). (F) Overlay of graphs A and D showing both % knockdown (black boxes) and % transduction (white boxes). Results are shown as mean±SEM.
Figures 5A, 5B, 5C, 5D:
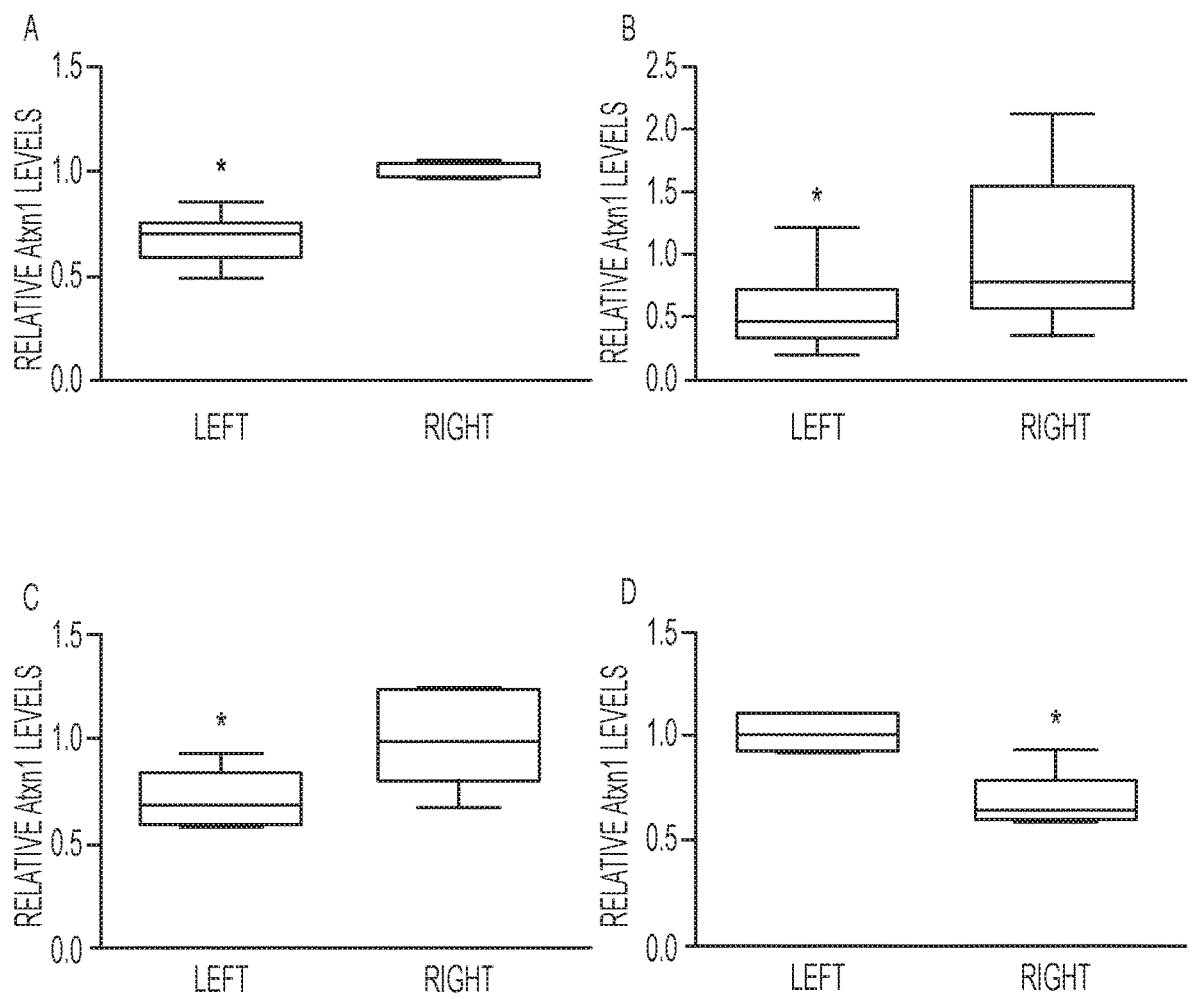
FIGS. 5A-5D. Silencing of ATXN1 messenger RNA levels. (A) Expression of Atxn1 from tissue punches taken from the left cerebellar cortex relative to the right (n=6; *P<0.05). (B) Expression of ATXN1 from tissue punches taken from left dentate nuclei relative to the right (n=6; *P<0.05). (C) Expression of ATXN1 from tissue punches taken from the left inferior olivary complex relative to the right (n=6; *P<0.05). (D) Expression of ATXN1 from tissue punches taken from the right ventral lateral thalamic nuclei relative to the left (n=6; *P<0.05) Results are shown as whisker plots.

Representative sagittal sections from the cerebellum were scored for % Purkinje cells transduced (GFP immunohistochemistry) for each animal (FIG. 4A). We found greater coverage of the anterior lobe (paleocerebellum; 33.5%±3.9; N=49) compared to the posterior lobe (13.7%±2.3; N=51) (FIG. 4B). Tissue punches taken from the cerebellar lobules and subjected to QRTPCR analysis showed significant suppression of endogenous ATXN1 distributed among the anterior (0.3497±0.0397) and posterior lobes (0.28±0.0413)

relative to the uninjected cerebellar hemispheres (FIG. 4C, D, E). Cumulatively, punches taken from the left cerebellar hemisphere showed >30% less AXTN1 (0.68±0.05) relative to the uninjected right hemisphere (1.01±0.001) (*P<0.05; FIG. 5A). Punches from the left DCN (0.54±0.35), left inferior olive (0.71±0.06) and right thalamus (0.69±0.05) also showed significantly lower levels of ATXN1 compared to their uninjected hemisphere (paired t-test *p<0.05; FIG. 5B-D). These data show that this delivery scheme provides for widespread gene silencing in the primate brain.

AAVmiS1eGFP is Well Tolerated in NHP Cerebellum

Inhibitory RNAs can cause toxicity in the brain (McBride, J. L., R. L. Boudreau, S. Q. Harper, P. D. Staber, A. M. Monteys, I. Martins, B. L. Gilmore, H. Burstein, R. W. Peluso, B. Polisky, B. J. Carter and B. L. Davidson (2008). "Artificial miRNAs mitigate shRNA-mediated toxicity in the brain: implications for the therapeutic development of RNAi." *Proc Natl Acad Sci USA* 105(15): 5868-5873) even when expressed in the context of an artificial miRNA (Monteys, A. M., R. M. Spengler, B. D. Dufour, M. S. Wilson, C. K. Oakley, M. J. Sowada, J. L. McBride and B. L. Davidson (2014). "Single nucleotide seed modification restores in vivo tolerability of a toxic artificial miRNA sequence in the mouse brain." *Nucleic Acids Res* 42(21): 13315-13327). Thus, we evaluated astroglial and microglial markers to gauge if there was an inflammatory response after rAAV1.miS1 delivery. Eight weeks post-injection, there were no significant differences in GFAP levels in tissues harvested from the DCN, cerebellar cortex, inferior olive, or thalamus as measured by QRTPCR (FIG. 6A). Microglial activation, assessed by Iba1 immunohistochemistry showed a slight enhancement in immunoreactivity in the left (FIG. 4B) vs. the right (FIG. 4C) cerebellar cortex. There were no notable differences between the left and right hemispheres of the DCN (FIG. 4D, E), brainstem (FIG. 4F, G) or thalamus (FIG. 4H, I).

Discussion

The technical feasibility and safety of injection of vectors expressing inhibitory RNA targeted to Atxn1 into the DCN of primate brain was unknown, as was the biodistribution and extent of silencing that could be achieved. We show that rAAV1.miS1 into the DCN of adult rhesus macaques results in broad distribution of transgene expression and reduction of ATXN1 mRNA in the cerebellum and extracerebellar areas affected in SCA1. rAAV1 was transported retrograde to PCs and the inferior olive. rAAV1 vector is also transported anterograde allowing for expression in the presynaptic axonal projections from the DCN.

We performed injections encompassing the medial, fastigial and dentate nuclei. PC transduction was quantified and 33% of PCs were found to be transduced on average, with anterior lobules transduced more readily than posterior lobules. As the superior medial cerebellum (anterior lobe) is more affected than the lateral cortex in SCA1, these results are encouraging for patient treatment.

Figure 8:
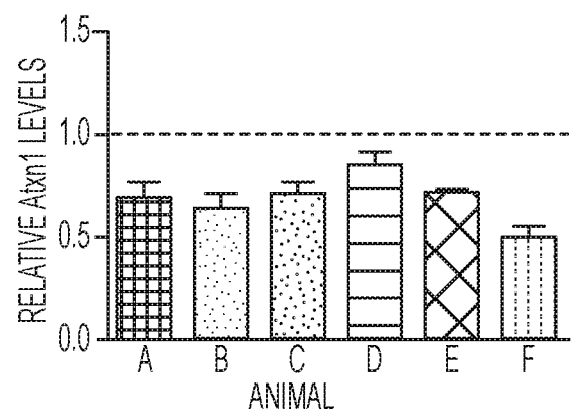
FIG. 8. ATXN1 messenger RNA levels in the cerebellar cortex of each individual animal averaged across all cerebellar lobules relative to their uninjected cerebellar hemisphere. Animal A: 0.69±0.07 (N=8); Animal B: 0.64±0.06 (N=8); Animal C: 0.71±0.07 (N=8); Animal D: 0.71±0.07 (N=8); Animal E: 0.71±0.03 (N=7); Animal F: 0.50±0.05 (N=6).

We found significant benefit from transducing ~10% of PCs after injection of rAAVs expressing a short hairpin RNA targeting human ATXN1 into the cerebellar cortex of a SCA1 transgenic mouse model (Xia, H., Q. Mao, S. L. Eliason, S. Q. Harper, I. H. Martins, H. T. Orr, H. L. Paulson, L. Yang, R. M. Kotin and B. L. Davidson (2004). "RNAi suppresses polyglutamine-induced neurodegeneration in a model of spinocerebellar ataxia." *Nat Med* 10(8): 816-820). In later work in this same model, we found ~30% reduction of mutant Atxn1 from directed delivery to the DCN, again with significant improvements in disease readouts. Finally, using a knock-in model but the same gene delivery approach, we found 27% reduction in murine Atxn1; however the tissue lysates in that work included transduced PCs and non-transduced cells in the granule and molecular layers. Similarly, we find 31% reduction in rhesus ATNX1 mRNA in cerebellar punches that include the molecular layer (including Purkinje cell bodies and their dendrites and other cells within the molecular layer) and cells within the granule cell layer (FIG. 8). These data indicate that infusions of rAAV into these deep cerebellar nuclei will provide sufficient coverage and knockdown of mutant ATXN1 mRNA levels in the cerebellar cortex for clinical benefit in patients.

In addition to the cerebellar cortex, the dentate and inferior olive are among the earliest and most severely affected regions (Robitaille, Y., L. Schut and S. J. Kish (1995). "Structural and immunocytochemical features of olivopontocerebellar atrophy caused by the spinocerebellar ataxia type 1 (SCA-1) mutation define a unique phenotype." *Acta Neuropathol* 90(6): 572-581; Donato, S. D., C. Mariotti and F. Taroni (2012). "Spinocerebellar ataxia type 1." *Handb Clin Neurol* 103: 399-421), as well as the ventral lateral thalamic nuclei (Rub, U., K. Burk, D. Timmann, W. den Dunnen, K. Seidel, K. Farrag, E. Brunt, H. Heinsen, R. Egensperger, A. Bornemann, S. Schwarzacher, H. W. Korf, L. Schols, J. Bohl and T. Deller (2012). "Spinocerebellar ataxia type 1 (SCA1): new pathoanatomical and clinicopathological insights." *Neuropathol Appl Neurobiol* 38(7): 665-680; Rub, U., L. Schols, H. Paulson, G. Auburger, P. Kermer, J. C. Jen, K. Seidel, H. W. Korf and T. Deller (2013). "Clinical features, neurogenetics and neuropathology of the polyglutamine spinocerebellar ataxias type 1, 2, 3, 6 and 7." *Prog Neurobiol* 104: 38-66). In support of SCA1 therapy, we see ~50% silencing in the DCN with transduction of most cells, and 30% silencing in the inferior olive and ventral lateral thalamus. This is similar to the biodistribution seen in our mouse studies; we see miS1 expression in the cerebellum and brainstem. Thus this delivery paradigm affords sufficient coverage of areas affected in SCA1, with reduction of Atxn1 mRNA to levels predicted to be therapeutic. In the present study, ATXN1 was reduced by from 30-50% depending on the region examined, and both quantitative and qualitative observations using inflammatory markers for astroglia and microglia suggests that this reduction in ataxin-1 is well tolerated. In summary, this study demonstrates the efficacy and tolerability of AAVmiS1eGFP administration to the DCN of NHP and the data are supportive of clinical application of this gene therapy in SCA1.

EXAMPLE 2

Modifications to the Injection Paradigm

Nine adult rhesus monkeys were injected at 3 different doses of AAV2/1.miS1 as shown in Table 2.

TABLE 2

Optimization of volumes in NHPs

| Dose | Surgical Target | Titer | Volume | Viral Genomes | Total VG | Total Vol |
|---|---|---|---|---|---|---|
| Low Titer | Fastigial | 6.67E+12 | 20 µl | 1.33E+11 | 6.67E+11 | 100 µl |
| | Interposed | 6.67E+12 | 30 µl | 2.00E+11 | | |
| | Dentate | 6.67E+12 | 50 µl | 3.34E+11 | | |
| High Titer | Fastigial | 1.25E+13 | 20 µl | 2.50E+11 | 1.25E+12 | 100 µl |
| | Interposed | 1.25E+13 | 30 µl | 3.75E+11 | | |
| | Dentate | 1.25E+13 | 50 µl | 6.25E+11 | | |

TABLE 2-continued

Optimization of volumes in NHPs

| Dose | Surgical Target | Titer | Volume | Viral Genomes | Total VG | Total Vol |
|---|---|---|---|---|---|---|
| High Volume | Fastigial | 1.25E+13 | 30 μl | 3.75E+11 | 1.88E+12 | 150 μl |
| | Interposed | 1.25E+13 | 45 μl | 5.63E+11 | | |
| | Dentate | 1.25E+13 | 75 μl | 9.38E+11 | | |

Figure 9:
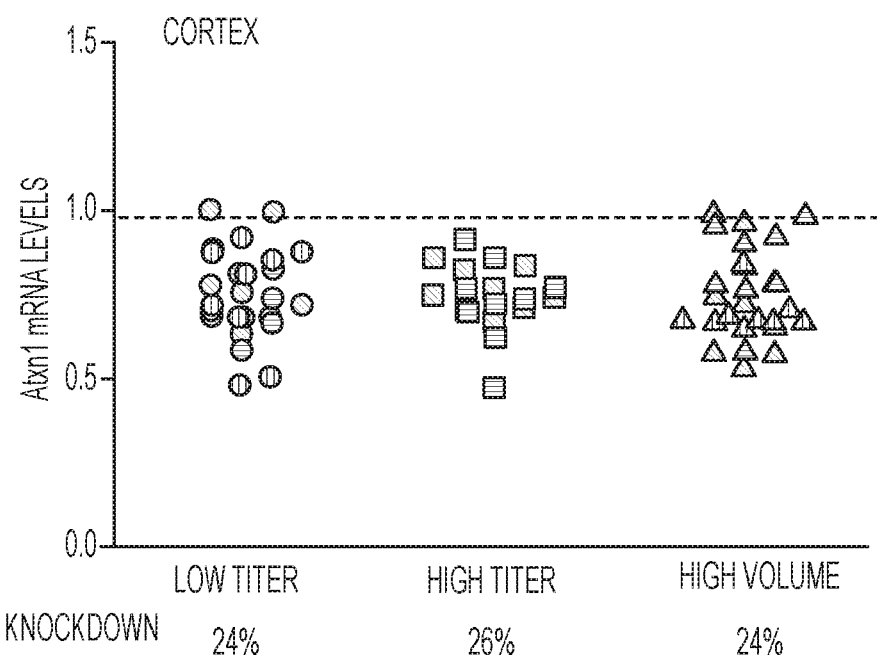
FIG. 9. Atxn1 mRNA levels in the cortex.
Figure 10:
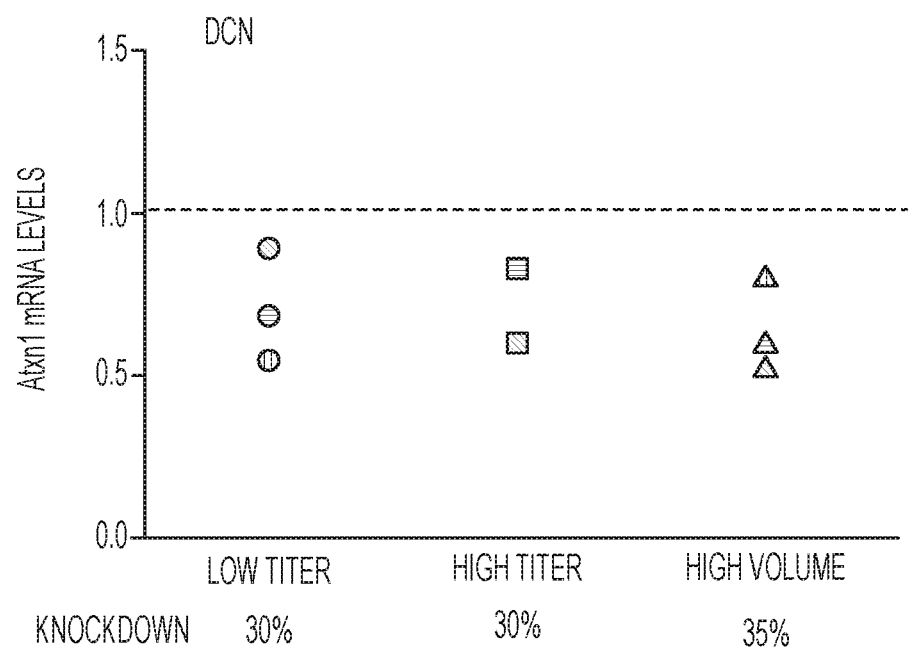
FIG. 10. Atxn1 mRNA levels in the DCN.

Three animals were given each dose and tissues were collected 12 weeks post-injections. Tissue collection was identical to that in Example 1 above. RNA was extracted from tissue punches taken from each of the medial cerebellar hemispheres and analyzed for ataxin-1 silencing by QRTPCR (FIG. 9). Animals receiving the low titer had ataxin-1 mRNA expression levels of 0.76±0.03 relative to the uninjected right cerebellar hemisphere. Animals receiving the high titer had ataxin-1 mRNA expression levels of 0.74±0.02 relative to the uninjected right cerebellar hemisphere. It is important to point out that one of the animals that received the high dose experienced technical complications during the injections which may have negatively affected the overall ataxin-1 silencing and has been left out of the analyses. Animals receiving the high volume had ataxin-1 mRNA expression levels of 0.76±0.03 relative to the uninjected right cerebellar hemisphere. Punches were also taken from the DCN, the site of injection and RNA extracted for QRTPCR analysis (FIG. 10). Animals receiving the low titer had ataxin-1 levels of 0.70±0.10 relative to the uninjected right hemisphere Animals receiving the high titer had ataxin-1 levels of 0.70±0.11 relative to the uninjected right hemisphere. Animals receiving the high volume had ataxin-1 levels of 0.65±0.08 relative to the uninjected right hemisphere.

EXAMPLE 3

Pre-Clinical Dosing Studies for Spinocerebellar Ataxia Type 1

Results

AAV2/1.miS1 Prevents Phenotypic Rotarod Deficits in SCA1 Mice at Two Doses

Figures 11A, 11B, 11C, 11D:
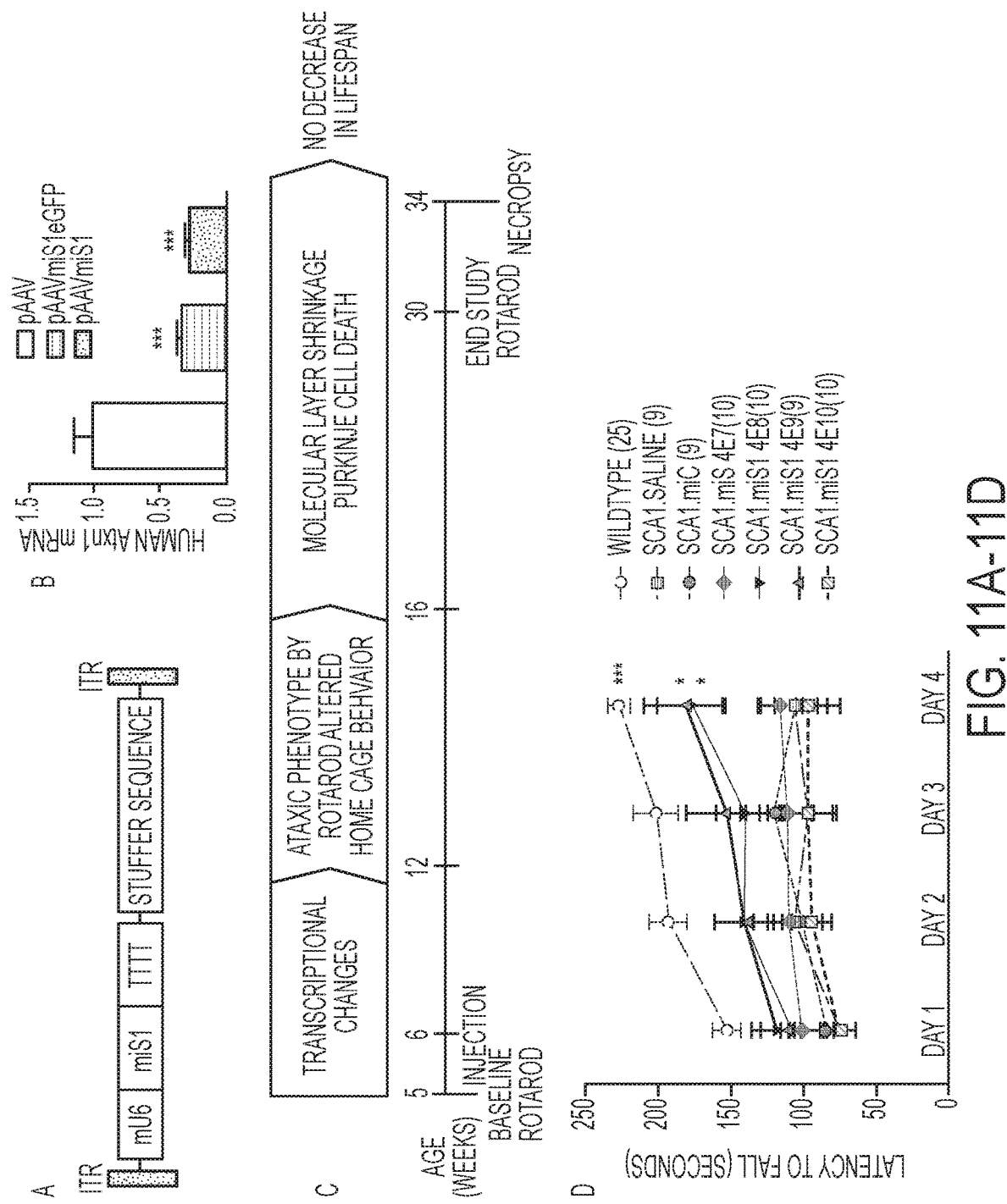
FIGS. 11A-11D. Experimental design and rotarod analysis. A) Cartoon of therapeutic viral construct. Inverted terminal repeats (ITR) surround murine U6 promoter driving artificial miRNA targeting human Ataxin-1 (miS1) with a polyA tail followed by a non-coding "stuffer sequence." B) Comparative silencing efficiency of previously utilized AAV2/1.miS1.eGFP and new construct AAV2/1.miS1 in HEK293 cells (N=4 replicates; * denotes p<0.001). C) Timeline of disease progression in B05 SCAT transgenic mice and timeline of study design. D) Rotarod performance on 4 days at 30 weeks of age (* denotes p<0.001; * denotes p<0.05; difference from AAV2/1.miC and Saline treated SCA1 animals).

Previous work demonstrated the efficacy of AAV2/1.miS1.eGFP in B05 transgenic SCA1 mice [Keiser, M. S., et al., *RNAi or overexpression: alternative therapies for Spinocerebellar Ataxia Type 1*. Neurobiol Dis, 2013. 56: p. 6-13.]. Delivery of AAV2/1.miS1.eGFP at 4E9 vg/hemisphere at 5 weeks of age prevented phenotypic rotarod deficits at 30 weeks of age compared to control treated transgenic littermates [Keiser, M. S., et al., *RNAi or overexpression: alternative therapies for Spinocerebellar Ataxia Type 1*. Neurobiol Dis, 2013. 56: p. 6-13]. In the current study, therapeutic AAV2/1.miS1.eGFP was modified to no longer express eGFP, but rather a safe "stuffer sequence" (SEQ ID NO:13, FIG. 21) making it suitable for clinical application (FIG. 11A). The sequence for AAV2/1.miS1 is SEQ ID NO:14 (FIGS. 22A-22D). To test for potency, HEK293 cells were transfected with AAV2/1.miS1.eGFP, AAV2/1.miS1 or empty AAV2/1 vector. AAV2/1.miS1.eGFP and AAV2/1.miS1 had 0.26±0.04 and 0.33±0.03, respectively, expression of Ataxin-1 24 hours post-transfection (*** p<0.001; FIG. 11B). Using the newly modified virus, AAV2/1.miS1, we repeated and improved upon our previous preventative study by adding three additional doses (Table 3).

TABLE 3

Treatment Groups for Preventative Study

| Genotype | Injection |
|---|---|
| SCA1 | AAV2/1.miS1 4E7 vg/hemisphere |
| SCA1 | AAV2/1.miS1 4E8 vg/hemisphere |
| SCA1 | AAV2/1.miS1 4E9 vg/hemisphere |
| SCA1 | AAV2/1.miS1 4E10 vg/hemisphere |
| SCA1 | AAV2/1.miC 4E8 vg/hemisphere |
| SCA1 | Saline |
| Wildtype | |

AAV2/1.miS1 was delivered bilaterally to the DCN of SCA1 transgenic mice at 6 weeks of age, following a baseline rotarod assessment. Treatment groups received AAV2/1.miS1 at doses of 4E10 vg/hemisphere, 4E9 vg/hemisphere, 4E8 vg/hemisphere, or 4E7 vg/hemisphere. Additional control treatment groups of transgenic mice received AAV2/1.miControl (miC) at 4E8 vg/hemisphere or saline. These animals were allowed to age to 30 weeks of age whereupon they were assayed by rotarod. They were then euthanized and their tissues collected for post-necropsy analysis (FIG. 11C). At 30 weeks of age on the fourth and final day of the assay (FIG. 11D), transgenic mice treated with saline fell off the rotarod apparatus at 98.8±22 seconds; transgenic mice treated with AAV2/1.miC fell at 105.7±12 seconds; transgenic mice treated with AAV2/1.miS1 at 4E7 vg/hemisphere fell at 116.4±15.8 seconds; transgenic mice treated with AAV2/1.miS1 at 4E10 vg/hemisphere fell at 106.1±22.6 seconds. Wildtype animals performed significantly better than most of the other treatment groups, falling at 226.5±7.4 seconds (*** p<0.001). Transgenic mice treated with AAV2/1.miS1 at 4E8 and 4E9 vg/hemisphere also performed significantly better (175.8±20.3 and 180.9±28.4 seconds, respectively) than control treated transgenic animals (* p<0.05) and no differently than wildtype littermates. To compensate for individual performance variances, we calculated the differences of the final rotarod performance minus their original performance at 5 weeks, on a mouse-by-mouse basis. The difference in performance demonstrates that AAV2/1.miS1 treated animals at doses 4E8 and 4E9 vg/hemisphere perform as well as wildtype littermates, and AAV2/1.miS1 treated animals at doses 4E7 and 4E10 vg/hemisphere trend to performance better than control treated transgenic animals. Their fourth day performance, although significantly different from wildtype littermates, were not significantly different from AAV2/1.miS1 treated animals at doses 4E7 and 4E10 vg/hemisphere ( p<0.01; * p<0.001; FIG. 11E).

Figures 12A, 12B, 12C:
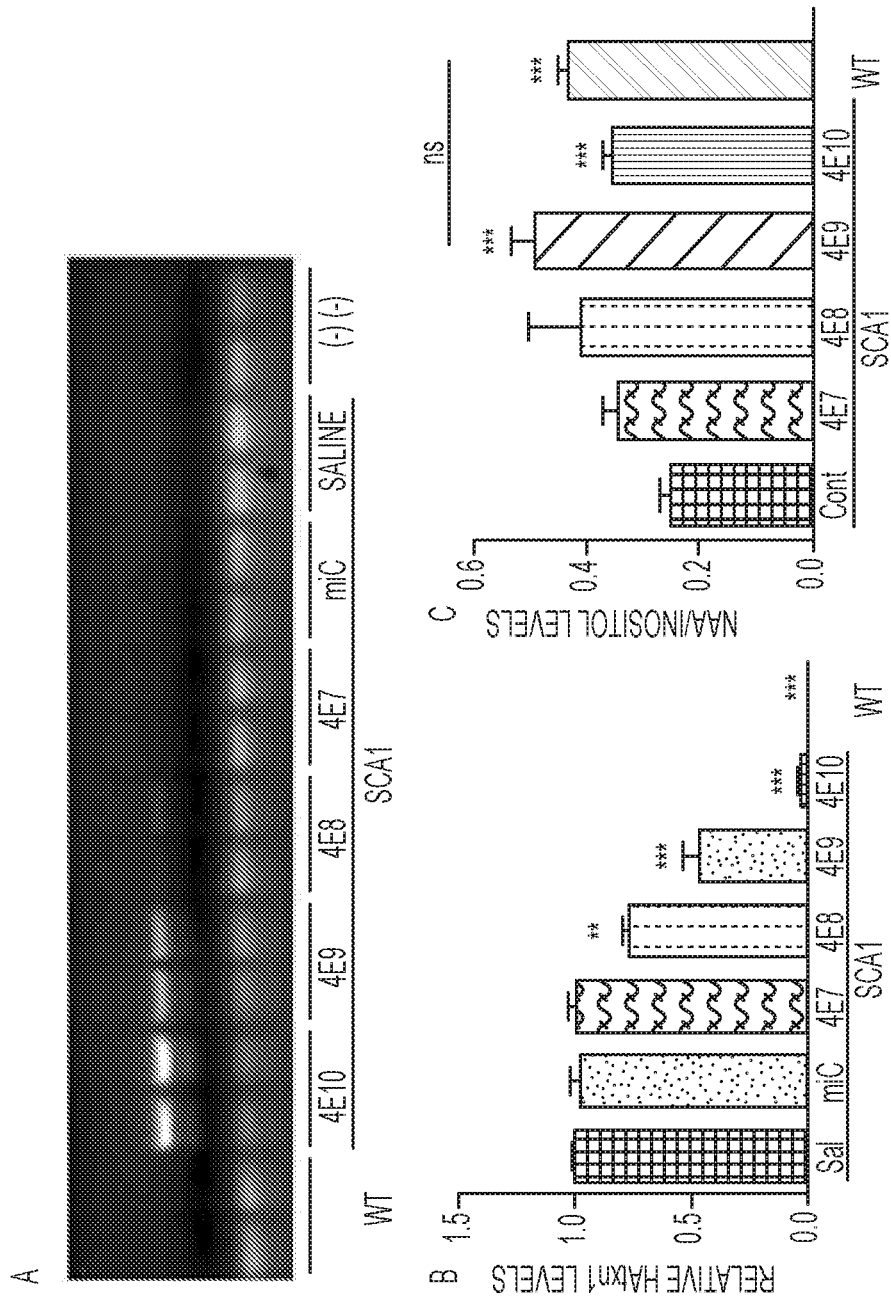
FIGS. 12A-12C. sqPCR, QRTPCR, and NMR analyses of whole cerebellar extracts. A) Semi-quantitative expression of miS1 from whole cerebellar extracts. B) Quantitative expression of human Ataxin-1 mRNA levels from whole cerebellar extracts (N≥3;  denotes p<0.01; * denotes p<0.001; differences from saline injected SCA1 mice). C) Ratio of NAA/Inositol levels from whole cerebellar extracts (N=3; *** denotes p<0.001; differences from control treated SCA1 mice).

AAV2/1.miS1 Significantly Knocks-Down Atxn1 in SCA1 Mouse Cerebella and Prevents Phenotypic Metabolite Differences Semi-quantitative (sq) PCR was performed on whole cerebellar lysates to verify miS1 expression (FIG. 12A). There is a distinct gradient of miS1 expression, the strongest seen in cerebella treated with AAV2/1.miS1 at 4E10 vg/hemisphere and decreasing until there is no visible miS1 expression in cerebella treated with AAV2/1.miS1 at 4E7 vg/hemisphere. QRTPCR analyzed whole cerebellar lysates for mRNA levels of human Ataxin-1 (FIG. 12B). The gradient of Ataxin-1 knockdown inversely correlated to the miS1 expression seen in the sqPCR assay. Levels of Ataxin-1 mRNA are reported relative to Saline treated SCA1 mice (1.00±0.01). Transgenic mice treated with AAV2/1.miC (0.98±0.04) and AAV2/1.miS1 @ 4E7 vg/hemisphere (1.00±0.03) had similarly high levels of Ataxin-1. Transgenic mice treated with AAV2/1.miS1 at 4E8 vg/hemisphere had significantly reduced levels of Ataxin-1 (0.77±0.03;  p<0.01). Transgenic mice treated with AAV2/1.miS1 @ 4E9 vg/hemisphere had greater knockdown (0.47±0.07; * p<0.001), whereas mice treated with AAV2/1.miS1 @ 4E10 vg/hemisphere had almost complete ablation of human Ataxin-1 mRNA levels (0.04±0.01; *** p<0.001) relative to control treated SCA1 mice.

Figures 17A, 17B:
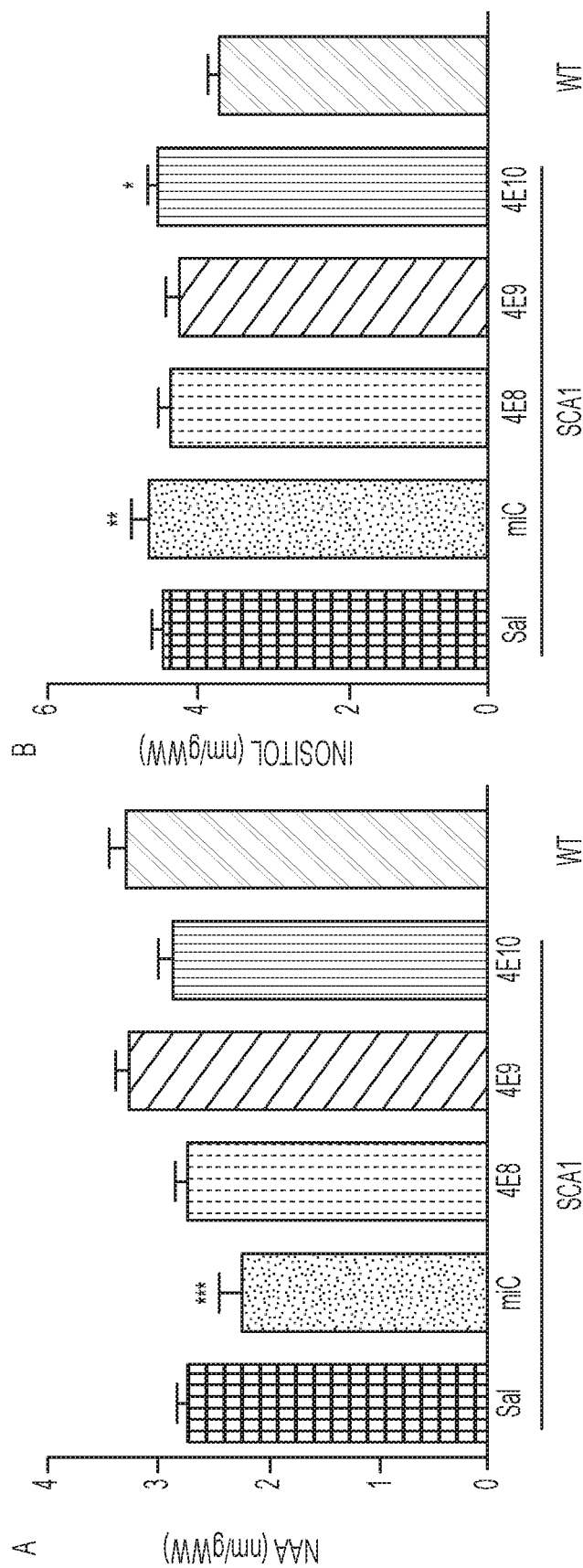
FIGS. 17A-17B. NMR analyses of whole cerebellar extracts. A) N-acetylaspartate levels from whole cerebellar extracts (N=3;  denotes p<0.01; * denotes p<0.001; differences from control treated SCA1 mice). B) Inositol levels from whole cerebellar extracts (N=3; * denotes p<0.05;  denotes p<0.01; * denotes p<0.001; differences from control treated SCA1 mice).

High field proton magnetic resonance spectroscopy ($^1$H MRS) is currently the best technology for non-invasive biomarkers in SCA1 patients. Patients reliably have lower levels of N-acetylaspartate (NAA), with elevated levels of inositol [Oz, G., et al., *Neurochemical alterations in spinocerebellar ataxia type 1 and their correlations with clinical status*. Mov Disord, 2010. 25(9): p. 1253-61]. The same dysregulations have been recapitulated in transgenic SCA1 mice [Oz, G., et al., *Noninvasive detection of presymptomatic and progressive neurodegeneration in a mouse model of spinocerebellar ataxia type 1*. J Neurosci, 2010. 30(10): p. 3831-8]. Whole cerebellum extracts were assayed by nuclear magnetic resonance (NMR) to attain metabolite readouts. As seen in previous studies, control treated transgenic SCA1 mice had significantly reduced levels of NAA (0.92±0.03) compared to wildtype littermates (1.73±0.02, * p<0.001; FIGS. 17A-17B). Transgenic mice treated with AAV2/1.miS1 at 4E9 vg/hemisphere also had significantly increased levels of NAA compared to control treated animals but no significant difference from wildtype littermates (1.48±0.15;  p<0.01). Control treated transgenic mice also had significantly higher levels of inositol (4.46±0.19) compared to wildtype littermates (3.64±0.04) and all other treatment groups (* p<0.05;  p<0.01; * p<0.001; FIGS. 17A-17B). The ratio of NAA to inositol is often used to illustrate metabolite differences. Here, we see the ratio of NAA/inositol is significantly reduced for control treated SCA1 mice (0.21±0.02 compared to wildtype littermates (0.48±0.01; * p<0.001; FIG. 12C**). Transgenic mice receiving AAV2/1.miS1 at 4E9 vg/hemisphere and 4E10 vg/hemisphere had levels also significantly higher than control treated mice (0.53±0.03 and 0.39±0.02, respectively) and were not significantly different from wildtype littermates.

Figures 13A, 13B, 13C, 13D, 13E, 13F:
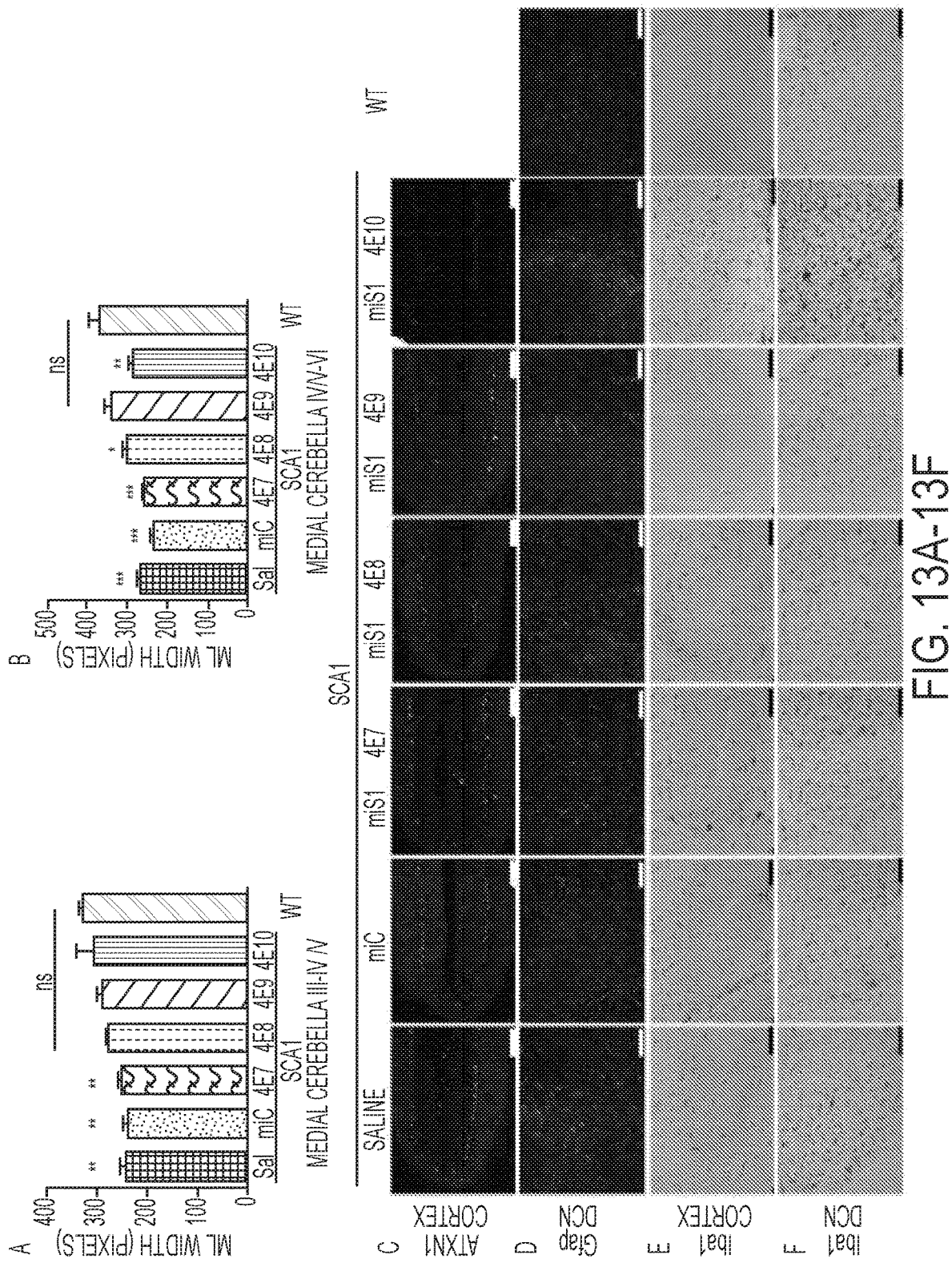
FIGS. 13A-13F. Immunohistochemistry and quantification of cerebellar molecular layer widths. A) Quantification of molecule layer width between Purkinje cell layers of lobule III and IV/V from sagittal cerebellar sections 0.5 mm from midline (N≥3; ** denotes p<0.01; differences from wildtype). B) Quantification of molecule layer width between Purkinje cell layers of lobule IV/V and VI from sagittal cerebellar sections 0.5 mm from midline (N≥3; * denotes p<0.05;  denotes p<0.01; * denotes p<0.001; differences from wildtype). C) Representative sagittal cerebellar sections stained with α-Ataxin-1. Scale Bar=100 μm. D) Representative sagittal DCN stained with α-Gfap. Scale Bar=100 μm. E) Representative sagittal cerebellar cortex stained with α-Iba1. Scale Bar=100 μm. F) Representative sagittal cerebellar DCN stained with α-Iba1. Scale Bar=100 μm.
Figure 18:
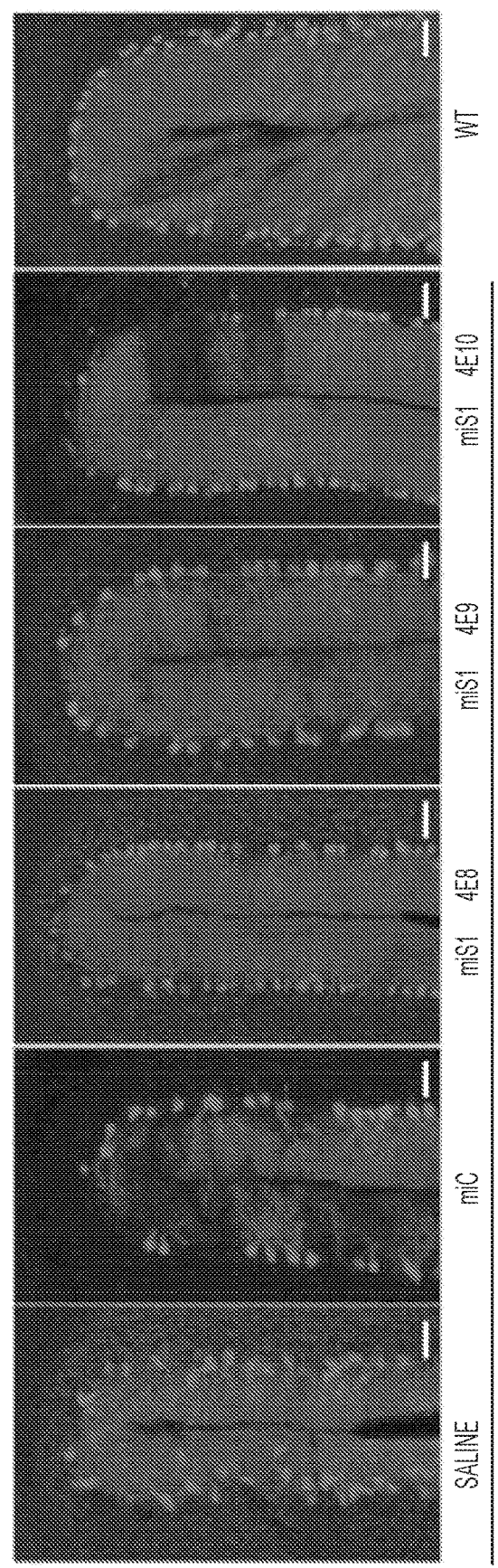
FIG. 18. Immunohistochemistry of cerebellum in presymptomatic dosing study. Cerebellar lobule IV/V-VI stained for α-Calbindin. Scale Bar=150 μm.

AAV2/1.miS1 at 4E9 vg/Hemisphere Prevents Cerebellar Pathology without Increased Glial Response During disease progression, there is a retraction of the PC dendrites resulting in a thinning of the cerebellar molecular layer (ML) before the death of cerebellar Purkinje cells. PC soma and dendrites are visualized using α-Calbindin. Representative sagittal sections of the molecular layer between PC lobules IV/V and VI are displayed in FIG. 18. Quantification of the ML widths from medial cerebellar sections between lobules III-IV/V show a marked thinning in Saline, AAV2/1.miC, and AAV2/1.miS1 at 4E7 vg/hemisphere treated SCA1 mice (239±17.0; 237±8.6; 250±6.6, respectively) compared to wildtype littermates (328±8.6;  p<0.01; FIG. 13A**). However, there was no significant difference between wildtype littermates and SCA1 mice treated with AAV2/1.miS1 at 4E8, 4E9, and 4E10 vg/hemisphere (278±2.8; 289±13; 305±25.0, respectively). Similar ML thinning was seen in adjacent lobules IV/V-VI. SCA1 mice treated with Saline (266±9.0), AAV2/1.miC (234±9.0), AAV2/1.miS1 at 4E7 (257±5.4), AAV2/1.miS1 at 4E8 (299±12.8), and AAV2/1.miS1 at 4E10 (284±12.8) were all significantly smaller than wildtype littermates (369±26.7; * p<0.05;  p<0.01; * p<0.001; FIG. 13B). Still, the ML widths of SCA1 mice treated with AAV2/1.miS1 at 4E9 vg/hemisphere (340±18.0) were not significantly reduced compared to wildtype littermates.

Immunohistochemistry was performed to visualize human Ataxin-1 in the PCs of SCA1 mice (FIG. 13C). SCA1 mice treated with Saline and AAV2/1.miC have strong ataxin-1 signal is most of their PCs. SCA1 mice treated with AAV2/1.miS1 have decreasing levels of ataxin-1 positive PCs that correlate inversely to the dose. Most of the PCs are positive for ataxin-1 in mice treated with AAV2/1.miS1 at 4E7 vg/hemisphere, whereas there are no visible PCs with positive ataxin-1 expression in SCA1 mice treated with AAV2/1.miS1 at 4E10 vg/hemisphere. Histological staining for Glial fibrillary acidic protein (Gfap), an astrocytic marker, revealed uniform staining of Bergmann glia in wildtype cerebellar cortex (FIG. 13D), whereas the Gfap positive staining is patchy and irregular in SCA1 mice treated with saline or AAV2/1.miC. The staining becomes more uniform in SCA1 mice treated with AAV2/1.miS1 at 4E8 and 4E9 vg/hemisphere. In the DCN, the site of injection, there is similar amounts of Gfap positive cells in all of the samples, with the exception of SCA1 mice treated with AAV2/1.miS1 at 4E10 vg/hemisphere, which shows an increase of Gfap staining (FIG. 13E). Iba1 is a marker for microglia. All of the treatment groups shows staining similar to wildtype littermates, again, with the exception of SCA1 mice treated with AAV2/1.miS1 at 4E10 vg/hemisphere in both the cortex and the DCN (FIG. 13F-G).

AAV2/1.miS1 Reverses Rotarod Deficits Seen at 11 Weeks of Age

Figures 14A, 14B:
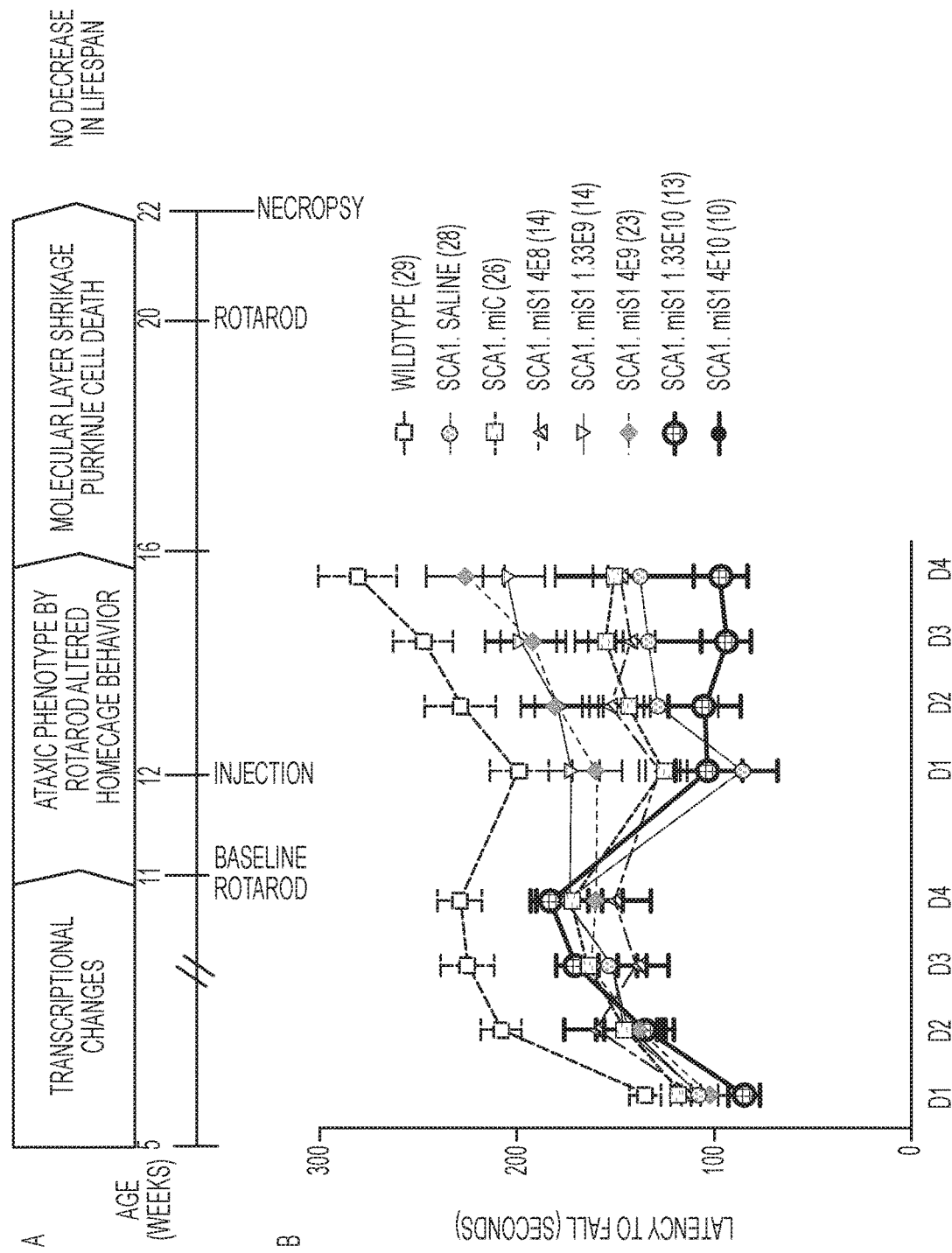
FIGS. 14A-14B. Experimental design and rotarod. A) Timeline of disease progression in B05 SCA1 transgenic mice and timeline of study design. B) Rotarod performance on 4 days at 20 weeks of age (* denotes p<0.05; *** denotes p<0.001; difference from AAV2/1.miC and Saline treated SCA1 animals).

Our second study administered our therapeutic AAV2/1.miS1 to post-symptomatic mice at 12 weeks of age. 11 week of mice were assayed by rotarod and then injected at 12 weeks of age (FIG. 14A and Table 4).

Table 4: Treatment Groups for Reversal Study

TABLE 4

Treatment Groups for Reversal Study

| Genotype | Injection | | |
|---|---|---|---|
| SCA1 | AAV2/1.miS1 | 4E8 | vg/hemisphere |
| SCA1 | AAV2/1.miS1 | 1.3E9 | vg/hemisphere |
| SCA1 | AAV2/1.miS1 | 4E9 | vg/hemisphere |
| SCA1 | AAV2/1.miS1 | 1.3E10 | vg/hemisphere |
| SCA1 | AAV2/1.miS1 | 4E10 | vg/hemisphere |
| SCA1 | AAV2/1.miC | 4E8/4E9 | vg/hemisphere |
| SCA1 | Saline | | |
| Wildtype | | | |

End-study rotarod was conducted at 20 weeks of age and tissue collected for post-necropsy analysis. At 11 weeks of age on the final day of testing, SCA1 mice presented with a significant rotarod deficit, falling off the rod at 168±4.9 seconds, whereas wildtype littermates stayed on the rod for 216±12.5 seconds (* p<0.001; FIG. 14B left). At 20 weeks of age on the final day of testing, wildtype littermates (280±20) continued to perform significantly better than SCA1 treated with Saline (143±10) of AAV2/1.miC (151±10; * p<0.001; FIG. 14B right). SCA1 mice treated with AAV2/1.miS1 at 4E8 (148±14), 1.33E10 (97±15) and 4E10 vg/hemisphere (138±43) also continued to perform poorly. However, SCA1 mice treated with AAV2/1.miS1 at 4E9 vg/hemisphere (226±20) and 1.3E9 (204±19) performed significantly better than they did at 11 weeks of age and also significantly better than their other SCA1 littermates. This supports our hypothesis that AAV2/1.miS1 can reverse SCA1 symptoms in ataxic mice.

Figures 15A, 15B, 15C, 15D, 15E:
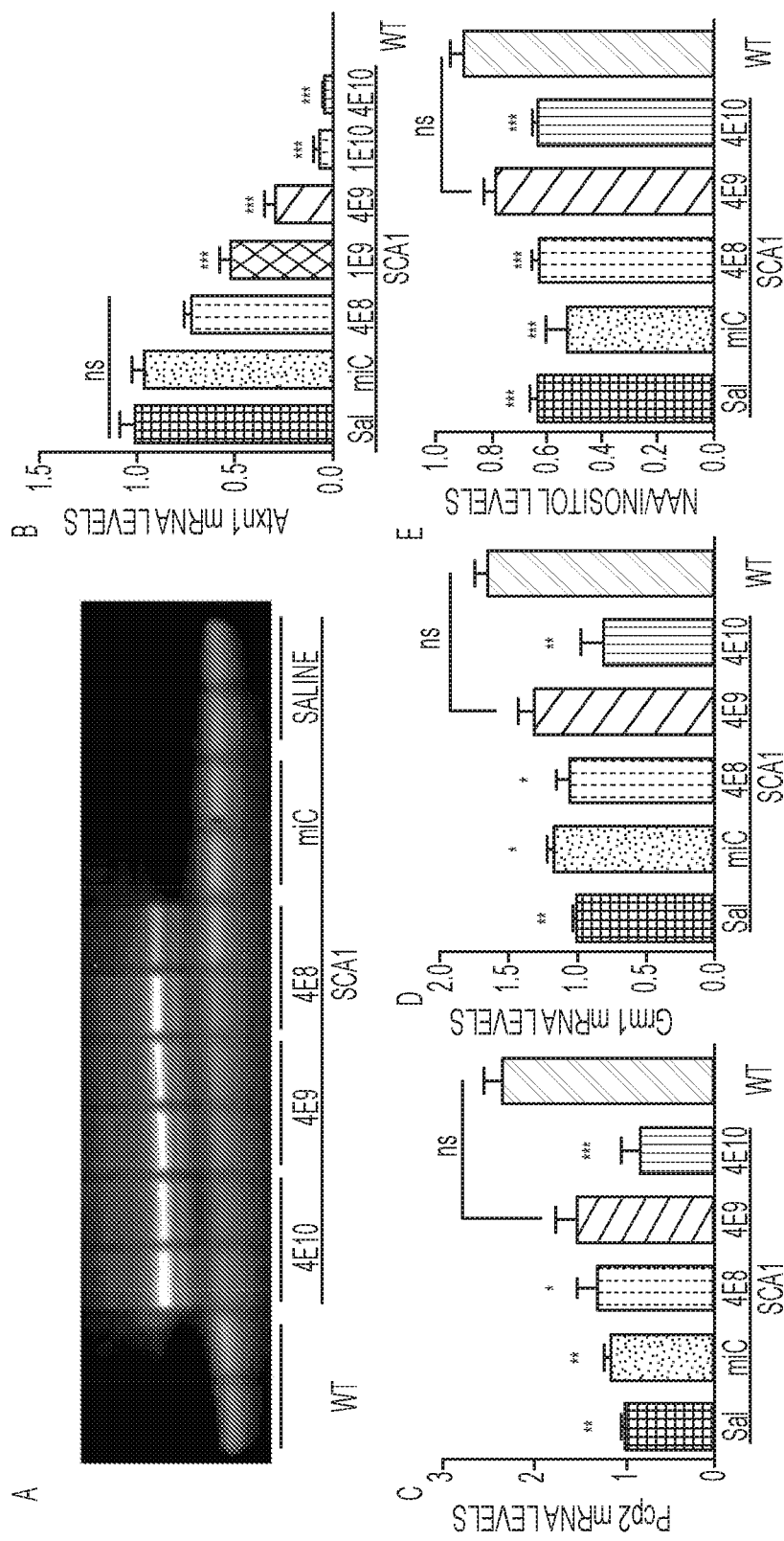
FIGS. 15A-15E. sqPCR, QRTPCR, and NMR analysis of whole cerebellar extracts. A) Semi-quantitative expression of miS1 from whole cerebellar extracts. B) Quantitative expression of human Ataxin-1 mRNA levels from whole cerebellar extracts (N=3-4;  denotes p<0.01; * denotes p<0.001; differences from Saline injected SCA1 mice). C) Quantitative expression of mouse Pcp2 mRNA levels from whole cerebellar extracts (N=3-4; * denotes p<0.05;  denotes p<0.01; * denotes p<0.001; differences from wildtype mice). D) Quantitative expression of mouse Grm1 mRNA levels from whole cerebellar extracts (N=3-4; * denotes p<0.05; ** denotes p<0.01; differences from wildtype mice). E) Ratio of NAA/Inositol levels from whole cerebellar extracts.

AAV2/1 Reduces Ataxin-1 in Post-Symptomatic Mouse Cerebella and Improves Molecular Readouts sqPCR was performed on whole cerebellar lysates to verify miS1 expression (FIG. 15A). Strong miS1 expression was confirmed in all three doses administered to post-symptomatic SCA1 mice. QRTPCR analyzed whole cerebellar lysates in all doses for mRNA levels of human Ataxin-1 (FIG. 15B). SCA1 mice treated with Saline (1.00±0.08), AAV2/1.miC (0.95±0.06), and AAV2/1.miS1 at 4E8 vg/hemisphere had similar levels of Ataxin-1 (0.72±0.03) that were not statistically different from each other. SCA1 mice treated with AAV2/1.miS1 at 1.3E9 vg/hemisphere had significantly greater knockdown (0.52±0.06; * $p<0.0001$), and 4E9 vg/hemisphere continued with higher knockdown (0.329±0.05; * $p<0.0001$), whereas mice treated with AAV2/1.miS1 at 1.3E10 and 4E10 vg/hemisphere had almost complete ablation of human Ataxin-1 mRNA levels (0.07±0.03 and 0.03±0.02, respectively; *** $p<0.0001$) relative to Saline treated SCA1 mice.

QRTPCR was also done for genes known to be dysregulated in SCA1 mouse models. Pcp2 is also known to be downregulated in SCA1 mice. Transgenic SCA1 mice treated with Saline (1.00±0.04) or AAV2/1miC (1.15±0.07) had significantly lower levels than wildtype littermates (2.35±0.20; ** $p<0.01$; FIG. 15C). Although transgenic mice treated with AAV2/1miS1 at 4E8 vg/hemisphere (1.30±0.23) and 4E10 vg/hemisphere (0.83±0.20) also had significantly lower levels of Pcp2 relative to wildtype littermates (* $p<0.05$ and ***$p<0.001$), SCA1 mice treated with AAV2/1.miS1 at 4E9 vg/hemisphere had Pcp2 levels (1.52±0.25) that were not significantly different wildtype littermates. Metabotropic glutamate receptor type 1 (Grm1) is also known to be downregulated in SCA1 mice. There were significantly reduced Grm1 levels in SCA1 mice treated with Saline (1.00±0.04), AAV2/1.miC (1.17±0.05), AAV2/1.miS1 at 4E8 (1.05±0.10) and 4E10 vg/hemisphere (0.81±0.17) relative to wildtype littermates (1.65±0.09; * $p<0.05$; ** $p<0.01$; FIG. 15D). Of note, SCA1 mice treated with AAV2/1.miS1 at 4E9 vg/hemisphere (1.31±0.12) expressed Grm1 at levels not significantly different from wildtype littermates.

Figures 19A, 19B:
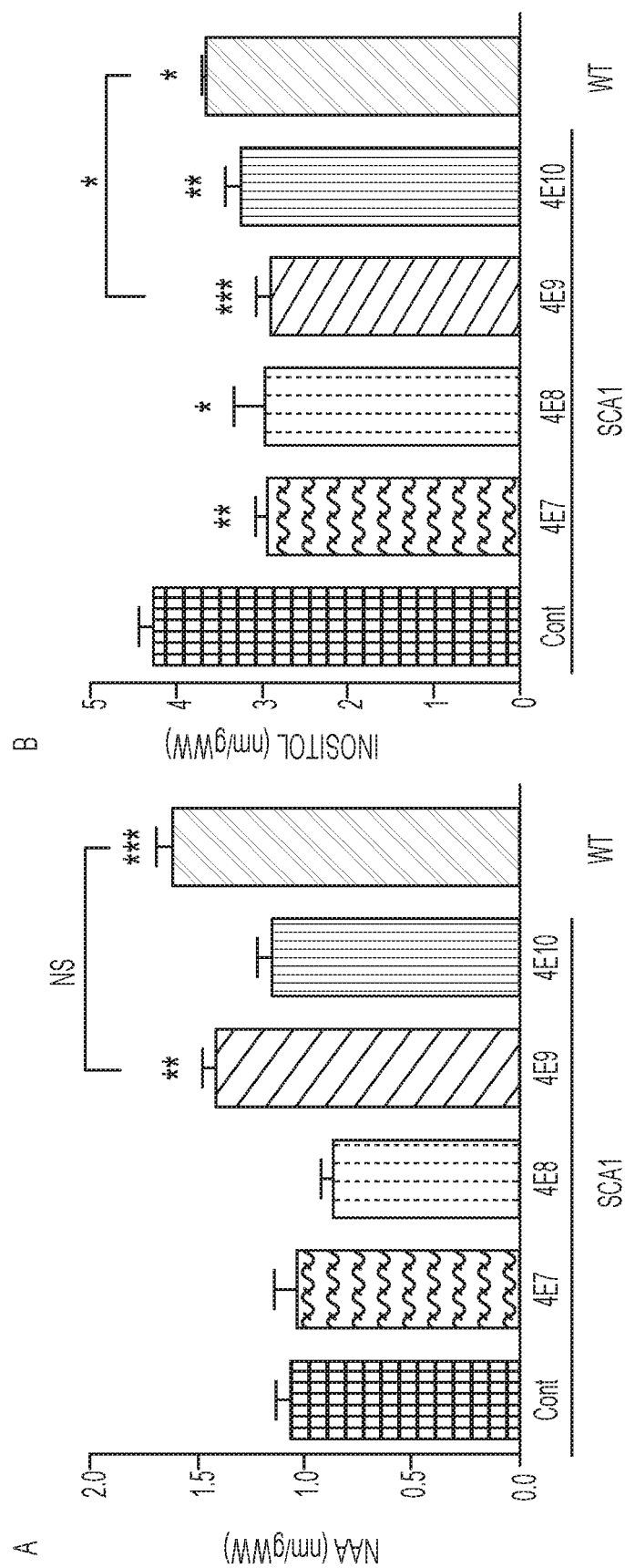
FIGS. 19A-19B. NMR analyses of whole cerebellar extracts. A) N-acetylaspartate levels from whole cerebellar extracts (N=6; *** denotes p<0.001). B) Inositol levels from whole cerebellar extracts (N=6; * denotes p<0.05; ** denotes p<0.01).

[1]H-magnetic resonance spectroscopy was performed on whole cerebellar lysates to analyze metabolite levels post-necropsy. Transgenic SCA1 mice treated AAV2/1.miC had significantly reduced levels of NAA (2.23±0.22) compared to wildtype littermates (3.30±0.13, * $p<0.001$; FIG. 19). Whereas SCA1 mice treated with saline (2.73±0.11), AAV2/1.miS1 at 4E8 vg/hemisphere (2.74±0.11) and 4E10 vg/hemisphere (2.86±0.14) had lower levels than wildtype littermates, there was no significant difference. Although SCA1 mice treated with AAV2/1.miS1 at 4E9 (3.27±0.11) had notably similar levels to that of wildtype mice. SCA1 mice treated with AAV2/1.miC and AAV2/1.miS1 at 4E10 vg/hemisphere also had significantly increased levels (4.65±0.19 and 4.52±0.12) of inositol compared to wildtype littermates (3.7±0.13;  $p<0.01$, * $p<0.05$; FIG. 19). SCA1 mice treated with saline (4.40±0.26), AAV2/1.miS1 at 4E8 (4.34±0.12) and 4E9 vg/hemisphere (4.22±0.17) had levels of inositol that were not statistically different from wildtype littermates. However, when we look at the ratio of NAA to inositol we see the ratio of NAA/inositol is significantly reduced in SCA1 mice treated with saline (0.63±0.03), AAV2/1.miC (0.52±0.08), AAV2/1.miS1 at 4E8 (0.63±0.04) and 4E10 vg/hemisphere (0.63±0.02) compared to wildtype littermates (0.90±0.05; *** $p<0.001$; FIG. 15E). Transgenic mice receiving AAV2/1.miS1 at 4E9 vg/hemisphere (0.78±0.04) had an NAA/inositol ratio that was not significantly different from wildtype littermates.

Figures 16A, 16B, 16C, 16D, 16E, 16F:
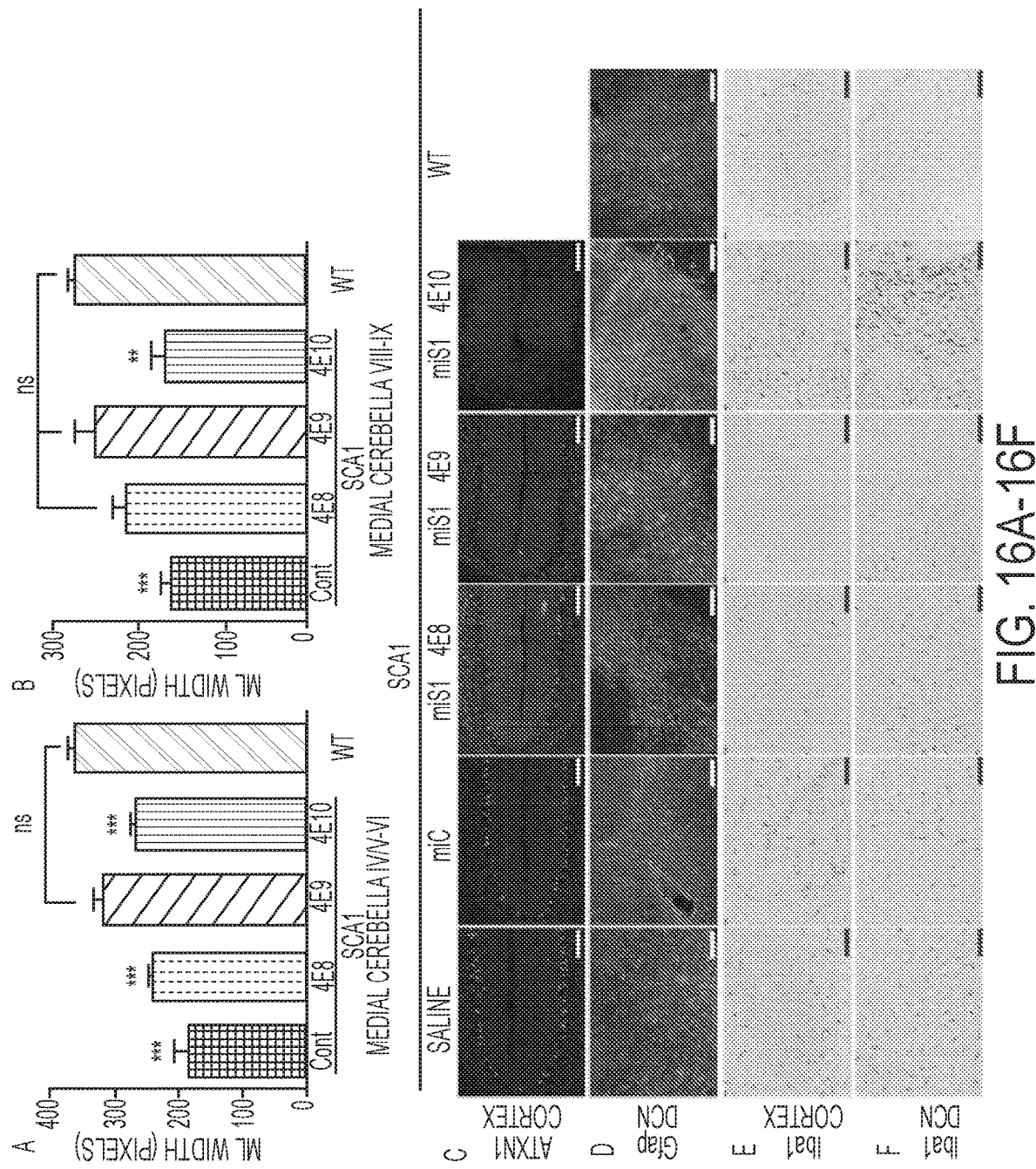
FIGS. 16A-16F Immunohistochemistry and quantification of cerebellar molecular layer widths. A) Quantification of molecule layer width between Purkinje cell layers of lobule IV/V and VI from sagittal cerebellar sections 0.5 mm from midline (N≥3; * denotes p<0.001 differences from wildtype). B) Quantification of molecule layer width between Purkinje cell layers of lobule VIII and IX from sagittal cerebellar sections 0.5 mm from midline (N≥3;  denotes p<0.01; *** denotes p<0.001; differences from wildtype). C) Representative sagittal cerebellar sections stained with α-Ataxin-1. Scale Bar=100 μm. D) Representative sagittal DCN stained with α-Gfap. Scale Bar=100 μm. E) Representative sagittal cerebellar cortex stained with α-Iba1. Scale Bar=100 μm. F) Representative sagittal cerebellar DCN stained with α-Iba1. Scale Bar=100 μm.
Figure 20:
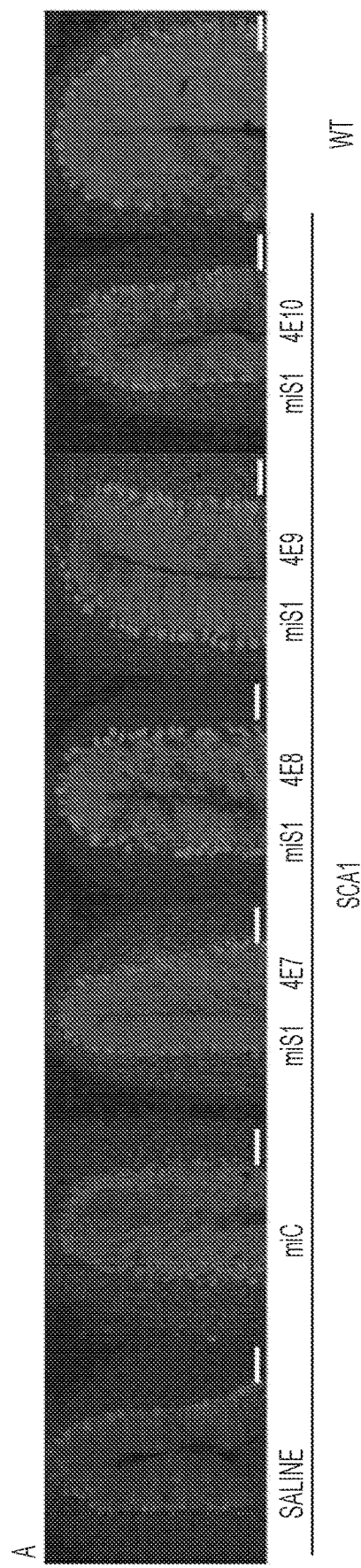
FIG. 20. Immunohistochemistry of cerebellum in post-symptomatic dosing study. Cerebellar lobule IV/V-VI stained for α-Calbindin. Scale Bar=150 μm.

AAV2/1.miS1 at 4E9 vg/Hemisphere Prevents Cerebellar Pathology without Increased Glial Response Representative sagittal sections of the molecular layer between PC lobules IV/V and VI are displayed in FIG. 20. Quantification of the ML widths from medial cerebellar sections between lobules IV/V and VI show a marked thinning in Control (Saline and AAV2/1.miC) treated SCA1 mice (183±23) compared to wildtype littermates (362±11; * $p<0.001$; FIG. 16A). SCA1 animals treated with AAV2/1.miS1 at 4E8 (240±6) and 4E10 vg/hemisphere (268±9) also had significantly reduced ML widths (* $p<0.001$). However, there was no significant difference between wildtype littermates and SCA1 mice treated with AAV2/1.miS1 4E9 vg/hemisphere (316±19). Quantification a rostral medial cerebellar section between VIII and IX also reveal significant thinning of the ML widths of control treated SCA1 mice (161±13) compared to wildtype littermates (270±13; * $p<0.001$; FIG. 16B). SCA1 mice treated with AAV2/1.miS1 at 4E10 vg/hemisphere (169±16) also showed significantly reduced ML widths relative to wildtype littermates ( $p<0.01$), although SCA1 mice treated with AAV2/1.miS1 at 4E8 (215±15) as well as 4E9 vg/hemisphere (249±25) had ML widths that were not significantly different from wildtype littermates.

Immunohistochemistry was performed to visualize human Ataxin-1 in the PCs of SCA1 mice (FIG. 16C). Similar to the results seen in the pre-symptomatic dosing study, SCA1 mice treated with Saline and AAV2/1.miC have strong ataxin-1 signal is most of their PCs. SCA1 mice treated with AAV2/1.miS1 have decreasing levels of ataxin-1 positive PCs that correlate inversely to the dose. Mice treated with AAV2/1.miS1 at 4E8 vg/hemisphere had less positive ataxin-1 PCs than control treated SCA1 mice, whereas mice treated with AAV2/1miS1 at 4E9 and 4E10 have few to no visible PCs with positive ataxin-1. Gfap staining revealed uniform staining of Bergmann glia in wildtype cerebellar cortex (FIG. 16D). Gfap positive staining is patchy and irregular in SCA1 mice treated with salin, AAV2/1.miC and AAV2/1.miS1 at 4E8 vg/hemisphere. The staining becomes more uniform in SCA1 mice treated with AAV2/1.miS1 at 4E9 vg/hemisphere and there are extremely high and sporadic patterns of Gfap-positive cells in mice treated with AAV2/1.miS1 at 4E10 vg/hemisphere. In the DCN, the site of injection, there is similar amounts of Gfap positive cells in all of the samples, with the exception of SCA1 mice treated with AAV2/1.miS1 at 4E10 vg/hemisphere, which shows an increase of Gfap staining (FIG. 16E). Iba1 is a marker for microglia. SCA1 mice treated with saline and AAV2/1.miC showed slightly higher levels of staining than wildtype mice and SCA1 mice treated with AAV2/1.miS1 at 4E8 and 4E9 vg/hemisphere in the cortex and DCN. Again, higher levels of Iba1-positive cells were seen in SCA1 mice treated with AAV2/1.miS1 at 4E10 vg/hemisphere in both the cortex and the DCN (FIG. 16F-G).

The following patents and patent publications are incorporated by reference herein: U.S. Pat. Nos. 8,329,890; 8,779,116; 8,481,710; 8,524,879; 8,487,088; 8,258,286; 8,524,881; 8,299,215; 8,691,948; WO 2012/109667; and WO 2013/172964.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of delivering a therapeutic agent to a central nervous system (CNS) cell of a mammal, wherein the mammal exhibits Spinocerebellar Ataxia Type 1 (SCA1) disease, comprising directly injecting to the mammal's deep cerebella nuclei a recombinant adeno-associated virus (rAAV) particle comprising a nucleic acid encoding an AAV1 capsid protein and a nucleic acid encoding miRNA ataxin type 1 (Atxn1) inserted between a pair of AAV2 inverted terminal repeats in a manner effective to infect the CNS cell of the mammal such that the CNS cell expresses the therapeutic agent in the mammal, and wherein the therapeutic agent is the nucleic acid encoding the miRNA Atxn1, and wherein the rAAV particle comprises the nucleotide sequence as set forth in SEQ ID NO: 14 and the CNS cell is a cerebellar Purkinje cell or deep cerebella nuclei.

2. A method of treating Spinocerebellar Ataxia Type 1 (SCA1) disease in a mammal, wherein the mammal exhibits Spinocerebellar Ataxia Type 1 (SCA1) disease, comprising directly injecting to the mammal's deep cerebella nuclei a recombinant adeno-associated virus (rAAV) particle comprising a nucleic acid encoding an AAV1 capsid protein and a nucleic acid encoding miRNA ataxin type 1 (Atxn1) inserted between a pair of AAV2 inverted terminal repeats in a manner effective to infect a central nervous system (CNS) cell of the mammal such that the CNS cell expresses the miRNA in the mammal, to treat Spinocerebellar Ataxia Type 1 (SCA1) disease, and wherein the miRNA reduces Atxn1 mRNA level, and wherein the rAAV particle comprises the nucleotide sequence as set forth in SEQ ID NO: 14, and the CNS cell is a cerebellar Purkinje cell or deep cerebella nuclei.

3. The method of claim 1, wherein the mammal is a non-rodent mammal.

4. The method of claim 1, wherein the non rodent mammal is a primate, horse, sheep, goat, pig, or dog.

5. The method of claim 4, wherein the primate is human.

6. The method of claim 1, wherein the method comprises directly injecting a plurality of the rAAV particles in a single dose to the mammal's deep cerebella nuclei.

7. The method of claim 6, wherein the plurality of rAAV particles are directly injected at a dose of about 1-5 ml of $1\times10^5$-$1\times10^{16}$ vg/ml.

8. The method of claim 2, wherein the mammal is a non-rodent mammal.

9. The method of claim 8, wherein the non-rodent mammal is a primate, horse, sheep, goat, pig, or dog.

10. The method of claim 2, wherein the rAAV particle is directly injected in a single dose to the mammal's deep cerebella nuclei.

11. The method of claim 2, wherein the rAAV particle is directly injected at a dose of about 1-5 ml of $1\times10^5$-$1\times10^{16}$ vg/ml.

12. The method of claim 2, wherein the Atxn1 mRNA level is reduced by at least 10% in the cerebellum, deep cerebella nuclei, brain stem (BS), and for thalamus.

* * * * *

UNITED STATES PATENT AND TRADEMARK OFFICE
CERTIFICATE OF CORRECTION

Page 1 of 1

PATENT NO.        : 11,027,024 B2
APPLICATION NO.   : 15/578170
DATED             : June 8, 2021
INVENTOR(S)       : Beverly L. Davidson and Megan S. Keiser It is certified that error appears in the above-identified patent and that said Letters Patent is hereby corrected as shown below:

In the Claims

Column 66, Lines 19 and 20, Claim 4, please delete "the non rodent mammal" and insert -- the mammal -- therefore.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

```
                            SEQUENCE LISTING

<160> NUMBER OF SEQ ID NOS: 14

<210> SEQ ID NO 1
<211> LENGTH: 77
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gugagcgagg acacaaggcu gagcagcagc ugugaagcca cagaugggcu gcugcucagc      60
cuuguguccc ugccuac                                                    77

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cggcgaacug aaguuccag aa                                               22

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
uucuggaaac uucaguucgc ca                                              22

<210> SEQ ID NO 4
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 4
ugagcgcggc gaacugaagu uuccagaacu guaaagccac agaugggouc uggaaacuuc    60 aguucgccac gccu                                                     74

<210> SEQ ID NO 5
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cgaccgugug aaucauuguu uaccggccag cagcaagcaa ucau                     44

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gugauugcuu gcugcuggcc ga                                             22

<210> SEQ ID NO 7
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ugagcgccgg ccagcagcaa gcaaucaucc guaaagccac agauggggug auugcuugcu    60
gcuggccgac gccu                                                     74

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ugauugcuug cugcuggccg a                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aagcaacgac ctgaagatcg a                                              21

<210> SEQ ID NO 10
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 10
tcgatcttca ggtcgttgct t                                              21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ucgaucuuca ggucguugcu u                                              21

<210> SEQ ID NO 12
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gucgaucuuc aggucguugc uu                                             22

<210> SEQ ID NO 13
<211> LENGTH: 3766
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gctatcccag gttgccttgg ttcttggcaa ttgggaaatt aagagggcag agagaatttg     60
aacagaaact gttctaatat tggtctttta ttgtgtaagt attgttcttt ggtaaacctc    120
cttcttttgg tttccaggaa ttgctggaca cagtggcttg gtgtgtgtct gaggactgta    180
ggccttggcc ctaggttgtg gttttaggtc tcaggtgctc ttcctggctg tctccttgct    240
tctttccctt gtcctcttct ttgtttccag ccttttctcc cttttgctta agttggtgc     300 agcagggttt ggctgctctc agattcctgc ttcctcagtt gctgtagttg tcaggcccag    360
aaggctggca gaaggatcag gatctggcta ggtttgctct cactgtggca gagtaggggg    420
aggaggagag caaaagtgac cccaggccag ctgtagggag cttaggcttg gtcaaccagc    480
cttcaggtcc tagactttgt cttctcttga gtttggctgt gtgtgtttgg tgggaactag    540
gttctactta gcccaagaaa ttgggcactt tttgcttgtg gtttctgtag agaattgcac    600
tgggtatctg acttagcctg gcagcttgcc tccctcaggt aggttagtct caggaagtga    660
agcaaagtcc agcaagaact tcttttgtgg cttaaagtct caattctgtg aggtgctggc    720
aaatcaccac cacaatcaag aggctgaagt gattttttgtc tagggaggca ggaaaggctt    780
cctggagtca gcagccagta ggtgaaagag tagattggag accttcttaa tcttcacaac    840
ctcttgtctc aagggtgcc aggaagctgt ggaggctgaa cccttctttt gctgccagag    900
agtgggacac cttgagggtc aggtcaaggg gttgtacctt gtttggtaga gaattagggg    960
ctcttgaaga ctttggttgt ggtcagggga gtgtatcttt taggaagagt gaccaagtga   1020
```

```
ggaagggtag aggaggacag gtgggaggga gtccaggtgg gagtgagtag acccagcagg      1080
agtgcagggc ctaaagccag gttggtggca gggctgtgag gagaggcagc cacctgtgtg      1140
tctgaagaag caggggcaag agggaagagg ccagcagact gccttcaccc agaaactgga      1200
atagattgtg agagaccttt ccctgctctt aggaggggct gagttccagt cctctcttgt      1260
tatacaaggg gcttggtatt tgtttacaaa agggtgtaa agctagggca aggtttgata       1320
aggcttctag gggtatttaa gaagtattgt tggggtaatt gtttgtccaa ttaactttgc      1380
tcttggaagg actttcagta caaactgcaa caacaggatt aggaagggaa aatttctgag      1440
ttggggttac tcctcagaat ttcccagatt gtgatctggt tttgattttc aagcttgctg      1500
acccaatagg ttaacccaca gttttaacc agaccttctc agtccactta cttcaactgc       1560
ccttgccaaa gtccaagaga tcttaaactg ttgtttggca cagcttcctc cctcttgggt      1620
gggcaagctt ttggaagaga aggctccttt gggtgagagt ggggcaccaa agtcttccct     1680
gtcccttccc ctagcttgag aagcccttct ctattgtgga ctttgtgcaa ttagcttaat      1740
tactagcttg aagttgacct tctggaaata ctttctggtt tagcctcaca agtgagcaag     1800
gagggttgag agttgtgctg tgaggattgt ggggccccag ctggcagcag gctctgggtc     1860 agggggggcag ggaccaaagg cttacctgac agtgaggagg gtctagtag gggatcagtt     1920 cccctgttgt tctttagaac cttctggata ttcttcttcc ctgattgggg gttgtgaaca     1980
atagaatcaa cttctacttg tagattgatt tagggagaac ttatacctca gttgttaagt     2040
caccctgtcc agattgtggg ttgctttcct atttgttcag aactttccca attacctcag     2100
aagcacttga aatttaaagg attttaaccc caacttaggg attatttcac ttagctcttg     2160
cacttttctt gataattgaa tcctcaggta ttcctctgtt tgggttacta atagttactt     2220
cttttggggg ggttttcccc tgaaaatctt ttatccccaa tttgtggctt accctctgaa     2280
ggttgtttga taattttgga agatttgaaa gtcttcttat tttacaaggt ttggggtctc     2340
tttaagctgc ttggttctct tgtcagctcc caaagcagaa gaaagctagc tgaaaattgc     2400
aatagagaag atacttcttt tccacctgtt ttcaactctt atcttcttga atttcagggc     2460 accttttcctt gctcctagtg cttgctatct gtttattatt ttccttcctg aatacccctga  2520 actccagctt gttctgctgt aattctggcc tccctggctt cttggactcc tgtttccttt    2580
gctctgtctt cccccaagtc agctcctgct gaacagcttc tcagctgaag tgaacctgga    2640
gtgcctggat cttgctggat cttttgagtat tgcctctggg gtccttggtt ccttctgctg   2700
agttgctcag aatctccact ccccccaacct tgtgtggccc ttcctgcact cctctgattc   2760
cccttgtctt ccctggtttc ttgctttggt ttaaagtctc cacagaactt ttgcagctct    2820
tctgaagacc tggaagcttt ttcttcttaa ttctcttctc ttgacctctt ttcccttctt    2880
tgagagctag aacttccctt ggtgaacttc tctttccaga attacttgcc ttcttttccc    2940
tcccacttac ctgttgtcca ggagaggtca gattgctgtg cttattggag gagaacccctt  3000 tcttccctgg gctcttcttc tcacttgact tcaccacttc acctaattcc ttggaccctc    3060
agtggtgtca ctgctggatt tttctttcct ttggctggcc ttagggcaca cccaggttga    3120
ctagaatagt cttggtattt agatccactc acttttttcag tttctgtgtc tgtctcttgc   3180
ctgcttctga cttaacccag agaaagcttc tctttcacaa gggttcttag attttttgttc  3240 actgagcacc ttcttttctg aggcagtgtt ttaccaatag gggttttcct agtcagtcta    3300
accttacctt tcttgttggg cttgtctttg gtcctgaccc tttctctgag tctgtaaccc    3360
agaattgctg tataacccaa ttacttgaaa tcctttagaa tcttaacact tcttacacct    3420
```

```
gatttccect tttattgtat ccaaattgaa ccaacccttt gtgaatttga cagtgatttc      3480
tcccagggat cctagtgtat aaggaatagg acttagtatt ttctattggg ggatatacca      3540
cttaccagat actgattttg ttggactttt aaccctttt tctctttttg aaagaaagtt      3600
aggaattatt tcttccagta gaaccagtgt aacctgaaag cctttgaaag agtagtttgg      3660
gtatagctat ctgaaaggaa tttctttcca agggatttcc ccagtgctga caacaaacaa      3720
acagacacac cctgcaaggt gagtgtaaag aacactagag caaggc                    3766
```

<210> SEQ ID NO 14
<211> LENGTH: 11591
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
gacgcgccct gtagcggcgc attaagcgcg gcgggtgtgg tggttacgcg cagcgtgacc       60
gctacacttg ccagcgccct agcgcccgct cctttcgctt tcttcccttc ctttctcgcc      120
acgttcgccg gctttccccg tcaagctcta atcggggggc tccctttagg gttccgattt      180
agtgctttac ggcacctcga cccaaaaaa cttgattagg gtgatggttc acgtagtggg      240
ccatcgccct gatagacggt ttttcgccct ttgacgttgg agtccacgtt cttaatagtg      300
gactcttgtt ccaaactgga acaacactca accctatctc ggtctattct tttgatttat      360
aagggatttt gccgatttcg gcctattggt taaaaaatga gctgatttaa caaaaattta      420
acgcgaattt taacaaaata ttaacgctta caatttaggt ggcacttttc ggggaaatgt      480
gcgcggaacc cctatttgtt tatttttcta aatacattca aatatgtatc cgctcatgag      540
acaataaccc tgataaatgc ttcaataata ttgaaaaagg aagagtatga gccatattca      600
acgggaaacg tcttgctcga agccgcgatt aaattccaac atggatgctg atttatatgg      660
gtataaatgg gctcgcgata atgtcgggca atcaggtgcg acaatctatc gattgtatgg      720
gaagcccgat gcgccagagt tgtttctgaa acatggcaaa ggtagcgttg ccaatgatgt      780
tacagatgag atggtcagac taaactggct gacggaattt atgcctcttc cgaccatcaa      840
gcattttatc cgtactcctg atgatgcatg gttactcacc actgcgatcc ccgggaaaac      900
agcattccag gtattagaag aatatcctga ttcaggtgaa aatattgttg atgcgctggc      960
agtgttcctg cgccggttgc attcgattcc tgtttgtaat tgtcctttta acagcgatcg     1020
cgtatttcgt ctcgctcagg cgcaatcacg aatgaataac ggtttggttg atgcgagtga     1080
ttttgatgac gagcgtaatg gctggcctgt tgaacaagtc tggaaagaaa tgcataagct     1140
tttgccattc tcaccggatt cagtcgtcac tcatggtgat ttctcacttg ataaccttat     1200
ttttgacgag gggaaattaa taggttgtat tgatgttgga cgagtcggaa tcgcagaccg     1260
ataccaggat cttgccatcc tatggaactg cctcggtgag ttttctcctt cattacagaa     1320
acggcttttt caaaaatatg gtattgataa tcctgatatg aataaattgc agtttcattt     1380
gatgctcgat gagttttctt aactgtcaga ccaagtttac tcatatatac tttagattga     1440
tttaaaactt cattttttaat ttaaaaggat ctaggtgaag atcctttttg ataatctcat     1500
gaccaaaatc ccttaacgtg agttttcgtt ccactgagcg tcagaccccg tagaaaagat     1560
caaaggatct tcttgagatc ctttttttct gcgcgtaatc tgctgcttgc aaacaaaaaa     1620
accaccgcta ccagcggtgg tttgtttgcc ggatcaagag ctaccaactc tttttccgaa     1680
```

```
ggtaactggc ttcagcagag cgcagatacc aaatactgtt cttctagtgt agccgtagtt   1740
aggccaccac ttcaagaact ctgtagcacc gcctacatac ctcgctctgc taatcctgtt   1800
accagtggct gctgccagtg gcgataagtc gtgtcttacc gggttggact caagacgata   1860
gttaccggat aaggcgcagc ggtcgggctg aacgggggt tcgtgcacac agcccagctt    1920
ggagcgaacg acctacaccg aactgagata cctacagcgt gagctatgag aaagcgccac   1980
gcttcccgaa gggagaaagg cggacaggta tccggtaagc ggcagggtcg aacaggaga    2040
gcgcacgagg gagcttccag ggggaaacgc ctggtatctt tatagtcctg tcgggtttcg   2100
ccacctctga cttgagcgtc gattttgtg atgctcgtca gggggcgga gcctatggaa     2160
aaacgccagc aacgcggcct ttttacggtt cctggccttt gctggccttt tgctcacat    2220
gttctttcct gcgttatccc ctgattctgt ggataaccgt attaccgcct ttgagtgagc   2280
tgataccgct cgccgcagcc gaacgaccga gcgcagcgag tcagtgagcg aggaagcgga   2340
agagcgcctg atgcggtatt ttctccttac gcatctgtgc ggtatttcac accgcataga   2400
ccagccgcgt aacctggcaa atcggttac ggttgagtaa taaatggatg ccctgcgtaa    2460
gcgggtgtgg gcggacaata aagtcttaaa ctgaacaaaa tagatctaaa ctatgacaat   2520
aaagtcttaa actagacaga atagttgtaa actgaaatca gtccagttat gctgtgaaaa   2580
agcatactgg acttttgtta tggctaaagc aaactcttca ttttctgaag tgcaaattgc   2640
ccgtcgtatt aaagaggggc gtggccaagg gcatggtaaa gactatattc gcggcgttgt   2700
gacaatttac cgaacaactc cgcggccggg aagccgatct cggcttgaac gaattgttag   2760
gtggcggtac ttgggtcgat atcaaagtgc atcacttctt cccgtatgcc aactttgta    2820
tagagagcca ctgcgggatc gtcaccgtaa tctgcttgca cgtagatcac ataagcacca   2880
agcgcgttgg cctcatgctt gaggagattg atgagcgcgg tggcaatgcc ctgcctccgg   2940
tgctcgccgg agactgcgag atcatagata tagatctcac tacgcggctg ctcaaacttg   3000
ggcagaacgt aagccgcgag agcgccaaca accgcttctt ggtcgaaggc agcaagcgcg   3060
atgaatgtct tactacggag caagttcccg aggtaatcgg agtccggctg atgttgggag   3120
taggtggcta cgtctccgaa ctcacgaccg aaaagatcaa gagcagcccg catggatttg   3180
acttggtcag ggccgagcct acatgtgcga atgatgccca tacttgagcc acctaacttt   3240
gttttagggc gactgccctg ctgcgtaaca tcgttgctgc tgcgtaacat cgttgctgct   3300
ccataacatc aaacatcgac ccacggcgta acgcgcttgc tgcttggatg cccgaggcat   3360
agactgtaca aaaaaacagt cataacaagc catgaaaacc gccactgcgc cgttaccacc   3420
gctgcgttcg gtcaaggttc tggaccagtt gcgtgagcgc atacgctact tgcattacag   3480
tttacgaacc gaacaggctt atgtcaactg ggttcgtgcc ttcatccgtt tccacggtgt   3540
gcgtcacccg gcaaccttgg gcagcagcga agtcgaggca tttctgtcct ggctggcgaa   3600
cgagcgcaag gtttcggtct ccacgcatcg tcaggcattg gcggccttgc tgttcttcta   3660
cggcaaggtg ctgtgcacgg atctgccctg gcttcaggag atcggaagac ctcggccgtc   3720
gcggcgcttg ccggtggtgc tgaccccgga tgaagtggtt cgcatcctcg gttttctgga   3780
aggcgagcat cgtttgttcg cccaggactc tagctatagt tctagtggtt ggctacagct   3840
tgcatgcctg caggcagctg cgcgctcgct cgctcactga ggccgcccgg gcgtcgggcg   3900
acctttggtc gcccggcctc agtgagcgag cgagcgcgca gagagggagt ggccaactcc   3960
atcactaggg gttccttgta gttaatgatt aacccgccat gctacttatc tacgtagcca   4020
tgctctagtg aattcgacgc cgccatctct aggcccgcgc cggccccctc gcacagactt   4080
```

```
gtgggagaag ctcggctact cccctgcccc ggttaatttg catataatat ttcctagtaa    4140
ctatagaggc ttaatgtgcg ataaaagaca gataatctgt tcttttaat actagctaca     4200 ttttacatga taggcttgga tttctataag agatacaaat actaaattat tattttaaaa   4260
aacagcacaa aaggaaactc accctaactg taaagtaatt gtgtgttttg agactataaa   4320
tatcccttgg agaaaagcct tgtttgcgtt tagtgaaccg tcagatggta ccgtttaaac   4380
tcgagtgagc gcagcaacga cctgaagatc gatccgtaaa gccacagatg gggtcgatct   4440
tcaggtcgtt gcttcgccta ctagagcggc cgccacagcg gggagatcca gacatgataa   4500
gatacatttt ttgaattcag ctatcccag gttgccttgg ttcttggcaa ttgggaaatt     4560
aagagggcag agagaatttg aacagaaact gttctaatat tggtctttta ttgtgtaagt   4620
attgttcttt ggtaaacctc cttcttttgg tttccaggaa ttgctggaca cagtggcttg   4680
gtgtgtgtct gaggactgta ggccttggcc ctaggttgtg gttttaggtc tcaggtgctc   4740
ttcctggctg tctccttgct tctttcctt gtcctcttct ttgtttccag ccttttctcc     4800
cttttgctta agtttggtgc agcagggttt ggctgctctc agattcctgc ttcctcagtt   4860
gctgtagttg tcaggcccag aaggctggca gaaggatcag gatctggcta ggtttgctct   4920
cactgtggca gagtaggggg aggaggagag caaaagtgac cccaggccag ctgtagggag   4980
cttaggcttg gtcaaccagc cttcaggtcc tagactttgt cttctcttga gtttggctgt   5040
gtgtgtttgg tgggaactag gttctactta gcccaagaaa ttgggcactt tttgcttgtg   5100
gtttctgtag agaattgcac tgggtatctg acttagcctg gcagcttgcc tccctcaggt   5160
aggttagtct caggaagtga agcaaagtcc agcaagaact tcttttgtgg cttaaagtct   5220
caattctgtg aggtgctggc aaatcaccac cacaatcaag aggctgaagt gattttttgtc   5280 tagggaggca ggaaaggctt cctggagtca gcagccagta ggtgaaagag tagattggag   5340
accttcttaa tcttcacaac ctcttgtctc aaggggtgcc aggaagctgt ggaggctgaa   5400
cccttctttt gctgccagag agtgggacac cttgagggtc aggtcaaggg gttgtaccct   5460
gtttggtaga gaattagggg ctcttgaaga ctttggttgt ggtcagggga gtgtatcttt   5520
taggaagagt gaccaagtga ggaagggtag aggaggacag gtgggaggga gtccaggtgg   5580
gagtgagtag acccagcagg agtgcagggc ctaaagccag gttggtggca gggctgtgag   5640
gagaggcagc cacctgtgtg tctgaagaag caggggcaag agggaagagg ccagcagact   5700
gccttcaccc agaaactgga atagattgtg agagaccttt ccctgctctt aggaggggct   5760
gagttccagt cctctcttgt tatacaaggg gcttggtatt tgtttacaaa aggggtgtaa   5820
agctagggca aggtttgata aggcttctag gggtatttaa gaagtattgt tggggtaatt   5880
gtttgtccaa ttaactttgc tcttggaagg actttcagta caaactgcaa caacaggatt   5940
aggaagggaa aatttctgag ttggggttac tcctcagaat ttcccagatt gtgatctggt   6000
tttgattttc aagcttgctg acccaatagg ttaaccaca agttttaacc agaccttctc     6060
agtccactta cttcaactgc ccttgccaaa gtccaagaga tcttaaactg ttgtttggca   6120
cagcttcctc cctcttgggt gggcaagctt ttggaagaga aggctccttt gggtgagagt   6180
ggggcaccaa agtcttccct gtcccttccc ctagcttgag aagcccttct ctattgtgga   6240 cttgtgcaa ttagcttaat tactagcttg aagttgacct tctggaaata ctttctggtt     6300
tagcctcaca agtgagcaag gagggttgag agttgtgctg tgaggattgt ggggccccag   6360
ctggcagcag gctctgggtc agggggggcag ggaccaaagg cttacctgac agtgaggagg   6420
ggtctagtag gggatcagtt cccctgttgt tctttagaac cttctggata ttcttcttcc   6480
```

```
ctgattgggg gttgtgaaca atagaatcaa cttctacttg tagattgatt tagggagaac    6540 ttataccctca gttgttaagt caccctgtcc agattgtggg ttgctttcct atttgttcag    6600
aactttccca attacctcag aagcacttga aatttaaagg attttaaccc caacttaggg    6660
attatttcac ttagctcttg cacttttctt gataattgaa tcctcaggta ttcctctgtt    6720
tgggttacta atagttactt cttttggggg ggttttcccc tgaaaatctt ttatccccaa    6780
tttgtggctt accctctgaa ggttgtttga taattttgga agatttgaaa gtcttcttat    6840
tttacaaggt ttggggtctc tttaagctgc ttggttctct tgtcagctcc caaagcagaa    6900
gaaagctagc tgaaaattgc aatagagaag atacttcttt tccacctgtt ttcaactctt    6960
atcttcttga atttcagggc acctttcctt gctcctagtg cttgctatct gtttattatt    7020
ttccttcctg aataccctga actccagctt gttctgctgt aattctggcc tccctggctt    7080
cttggactcc tgtttccttt gctctgtctt cccccaagtc agctcctgct gaacagcttc    7140
tcagctgaag tgaacctgga gtgcctggat cttgctggat cttttgagtat tgcctctggg    7200 gtccttggtt ccttctgctg agttgctcag aatctccact cccccaacct tgtgtggccc    7260
ttcctgcact cctctgattc cccttgtctt ccctggtttc ttgctttggt ttaaagtctc    7320
cacagaactt ttgcagctct tctgaagacc tggaagcttt tcttcttaa ttctcttctc    7380 ttgacctctt ttcccttctt tgagagctag aacttccctt ggtgaacttc tcttccaga    7440 attacttgcc ttcttttccc tcccacttac ctgttgtcca ggagaggtca gattgctgtg    7500
cttattggag gagaacccctt tcttccctgg gctcttcttc tcacttgact tcaccacttc    7560
acctaattcc ttggaccctc agtggtgtca ctgctggatt tttctttcct ttggctggcc    7620
ttagggcaca cccaggttga ctagaatagt cttggtattt agatccactc acttttcag    7680 tttctgtgtc tgtctcttgc ctgcttctga cttaacccag agaaagcttc tctttcacaa    7740
gggttcttag attttttgttc actgagcacc ttcttttctg aggcagtgtt ttaccaatag    7800
gggttttcct agtcagtcta accttacctt tcttgttggg cttgtctttg gtcctgaccc    7860
tttctctgag tctgtaaccc agaattgctg tataacccaa ttacttgaaa tcctttagaa    7920
tcttaacact tcttacacct gatttcccct tttattgtat ccaaattgaa ccaacccttt    7980
gtgaatttga cagtgatttc tcccagggat cctagtgtat aaggaatagg acttagtatt    8040
ttctattggg ggatatacca cttaccagat actgattttg ttggactttt aacccttttt    8100 tctcttttg aaagaaagtt aggaattatt cttccagta gaaccagtgt aacctgaaag    8160
cctttgaaag agtagtttgg gtatagctat ctgaaaggaa tttctttcca agggatttcc    8220
ccagtgctga caacaaacaa acagacacac cctgcaaggt gagtgtaaag aacactagag    8280
caaggctacg tagataagta gcatggcggg ttaatcatta actacaagga acccctagtg    8340
atggagttgg ccactccctc tctgcgcgct cgctcgctca ctgaggccgg gcgaccaaag    8400
gtcgcccgac gcccgggctt tgcccggggcg gcctcagtga gcgagcgagc gcgcagctgc    8460
ctgcaggtct gagacaataa ccctgataaa tgcttcaata atgtaagctt gtcgagaagt    8520
actagaggat cataatcagc cataccacat ttgtagaggt tttacttgct ttaaaaaacc    8580
tcccacacct ccccctgaac ctgaaacata aaatgaatgc aattgaggcc ttaattctag    8640
ccataaaagg tcttgagcag gccgttgaaa acctcagccg tatcagcaaa acggcggtgc    8700
ctggtgccgc cgcaatgacc attaaccgcg ttgcttcatc cgcgatagcg cagtcggcgt    8760
cacaggttgc ccgtgagaca aaggtacgcc ggaaactggt aaaggaaagg gccaggctga    8820
aaagggccac ggtcaaaaat ccgcaggcca gaatcaaagt tagccggggg gatttgcccg    8880
```

```
taatcaagct gggtaatgcg cggggttgtcc tttcgcgccg caggcgtcgt aaaaaggggc    8940
agcgttcatc cctgaaaggt ggcggcagcg tgcttgtggt gggtaaccgt cgtattcccg    9000
gcgcgtttat tcagcaactg aaaaatggcc ggtggcatgt catgcagcgt gtggctggga    9060
aaaaccgtta ccccattgat gtggtgaaaa tcccgatggc ggtgccgctg accacggcgt    9120
tgaaacaaaa tagtgagcgg atacggcgtg aacgtcttcc gaaagagctg ggctatgcgc    9180
tgaagcatca actcacactg gtaataaagc gtagaaacat actgaacctc cgtgcagccg    9240
tactggatgc actggagaag catgacaccg gggcgacgtt ttttgatggt cgccccgctg    9300
tttttgatga gcggattttt ccggcagttg ccgtttatct caccggcgct gaatacacgg    9360
gcgaagagct ggacagcgat acctggcagg cggagctgca tatcgaagtt ttcctgcctg    9420
ctcaggtgcc ggattcagag ctggatgcgt ggatggagtc ccggatttat ccggtgatga    9480
gcgatagccc ggcactgtca gatttgatca ccagtatggt gaccagcggc tatgactacc    9540
ggcgcgacga tgatgcgggc ttgtggagtt cagccgatct gacttatgtc attacctatg    9600
aaatgtctcc acgcttatga gcagcagact caacaggaca aaaatccgca gcagcagagc    9660
gataccgaag cgtcacggct gaaatatacc gaagaggcgc agaaggctta cgaacggctg    9720
aagacgccgc tggagaaata taccgcccgt caggaagaac tgaacaaggc actgaaagac    9780
gggaaaatcc tgaaggcgga ttacaacacg ctgatggcgg cggcgaaaaa ggattatgaa    9840
gcgacgctga aaaagccgaa acagtccagc gtgaaggtgt ctgcgggcga tagtcaggaa    9900
gacagtgctc atgctgccct gctgacgctt caggcagaac tcctgacgct ggagaagcaa    9960 gccgagcaa atgagaaaat cagccagcag cgccgggatt tgtggaaggc ggagagtcag    10020
ttcgcggtac tggaggaggc ggcgcaacgt cgccaggtgt ctgcacagga gaaatccctg    10080
ctggcgcata aagatgagac gctggagtac aaacgccagg tggctgcact tggcgacaag    10140
gttaggtatc aggagcgcct gaacgcgctg gcgcagcagg cggataaatt cgcacagcag    10200
caacgggcaa aacgggccgc cattgatgcg aaaagccggg ggctgactga ccggcaggca    10260
gaacgggaag ccacggaaca gcgcctgaag gaacagtatg gcgataatcc gctggcgctg    10320
aataacgtca tgtcagagca gaaaagacc tgggcggctg aagaccagct tcgcgggaac    10380
tggatggcag acctgaagtc cggctggagt gagtgggaag agagcgccac ggacagtatg    10440
tcgcaggtaa aaagtgcagc cacgcagacc tttgatggta ttgcacagaa tatgcggcg    10500 atgctgaccg gcagtgagca gaactggcgc agcttcaccc gttccgtgct gtccatgatg    10560
acagaaattc tgctttagca ggcaatggtg gggattgtcg ggagtatcgg cagcgccatt    10620
ggcggggctg ttggtggcgg cgcatccgcg tcaggcggta cagccattca ggccgctgcg    10680
gcgaaattcc attttgcaac cggaggattt acgggaaccg cgcaaata tgagccagcg    10740 gggattgttc accgtggtga gtttgtcttc acgaaggagg caaccagccg gattggcgtg    10800
gggaatcttt accggctgat gcgcggctat gccaccggcg gttatgtcgg tacaccgggc    10860
agcatggcag acagccggtc gcaggcgtcc gggacgtttg agcagaataa ccatgtggtg    10920
attaacaacg acggcacgaa cgggcagata ggtccggctg ctctgaaggc ggtgtatgac    10980
atggcccgca agggtgcccg tgatgaaatt cagacacaga tgcgtgatgg tggcctgttc    11040
tcctgacctc cacgatgagg cgcgcccaat tgttgttgtt aacttgttta ttgcagctta    11100
taatggttac aaataaagca atagcatcac aaatttcaca ataaagcat ttttttcact    11160 gcattctagt tgtggtttgt ccaaactcat caatgtatct tatcatgtct ggatctgatc    11220
actgatatcg cctaggagat ccgaaccaga taagtgaaat ctagttccaa actattttgt    11280
```

```
cattttttaat tttcgtatta gcttacgacg ctacacccag ttcccatcta ttttgtcact  11340
cttccctaaa taatccttaa aaactccatt tccaccccct ccagttccca actattttgt  11400
ccgcccacag cggggcattt ttcttcctgt tatgttttta atcaaacatc ctgccaactc  11460
catgtgacaa accgtcatct tcggctactt tttctctgtc acagaatgaa aatttttctg  11520
tcatctcttc gttattaatg tttgtaattg actgaatatc aacgcttatt tgcagcctga  11580
atggcgaatg g                                                      11591
```